United States Patent [19]
Smith et al.

[11] Patent Number: 5,858,368
[45] Date of Patent: Jan. 12, 1999

US005858368A

[54] VACCINE COMPRISING A BACULOVIRUS PRODUCED INFLUENZA HEMAGGLUTININ PROTEIN FUSED TO A SECOND PROTEIN

[75] Inventors: Gale E. Smith, Middlefield; Franklin Volvovitz, New Haven; Bethanie E. Wilkinson, Middletown; Andrei I. Voznesensky, West Hartford; Craig S. Hackett, Wallingford, all of Conn.

[73] Assignee: Protein Sciences Corporation, Meriden, Conn.

[21] Appl. No.: 453,848

[22] Filed: May 30, 1995

Related U.S. Application Data

[63] Continuation-in-part of Ser. No. 120,607, Sep. 13, 1993, Pat. No. 5,762,939.

[51] Int. Cl.$^6$ .................. A61K 39/145; A61K 39/295; C07K 14/11; C12N 15/44
[52] U.S. Cl. .................. 424/192.1; 424/196.11; 424/199.1; 424/210.1; 424/278.1; 424/280.1; 424/816; 530/396; 530/402; 530/412; 530/416; 530/417; 435/69.3
[58] Field of Search .................. 424/210.1, 278.1, 424/280.1, 816, 192.1, 199.1, 196.11; 530/396, 402, 412, 416, 417; 435/69.3

[56] References Cited

U.S. PATENT DOCUMENTS

| | | |
|---|---|---|
| 4,029,763 | 6/1977 | Kilbourne . |
| 4,289,690 | 9/1981 | Pestka et al. . |
| 4,659,669 | 4/1987 | Kleid et al. . |
| 4,752,473 | 6/1988 | Nayak et al. . |
| 4,920,213 | 4/1990 | Dale et al. . |
| 5,591,823 | 1/1997 | Hung et al. . |

OTHER PUBLICATIONS

Smith et al. Mol. Cell Biology 3(12):2156–65, 1983.
Pennock et al. Mol. Cell Biology 4(3):399–406, 1984.
Kreuter, "Microcapsules and Nanoparticles in Medicine and Pharmacy," Ed. M. Dunbrow (1991).
Luckow et al., Bio/Technology, 6:47–55 (1988).
Stanley et al., Virology, 56:640–645 (1973).
Kuroda et al., EMBO Journal, 5(6): 1359–1365 (1986).

*Primary Examiner*—Anthony C. Caputa
*Attorney, Agent, or Firm*—Frommer Lawrence & Haug LLP; Thomas J. Kowalski

[57] ABSTRACT

A method of preparing a recombinant influenza vaccine using DNA technology is provided. The resulting vaccine is a multivalent, preferably trivalent, influenza vaccine based on a mixture of recombinant hemagglutinin antigens cloned from influenza viruses having epidemic potential. The recombinant hemagglutinin antigens are full length, uncleaved (HAO), glycoproteins produced from baculovirus expression vectors in cultured insect cells and purified under non-denaturing conditions. The recombinant vaccine can be developed from primary sources of influenza, for example, nasal secretions from infected individuals, rather than from virus adapted to and cultured in chicken eggs. The process for cloning influenza hemagglutinin genes from influenza A and B viruses uses specially designed oligonucleotide probes and PCR. In the preferred embodiment, the cloned HA genes are then modified by deletion of the natural hydrophobic signal peptide sequences and replacing them with a new baculovirus signal peptide.

22 Claims, 4 Drawing Sheets

```
                    ┌─────────────────────┐
                    │  INFLUENZA VIRUS    │
                    │  STOCK FROM FDA     │
                    └─────────────────────┘
                              │
                              ▼
              VIRUS TITER (HEMAGGLUTINATION ASSAY)
                   ↙                    ↘
    INJECT 10 DAY OLD EGGS       OPTIMIZE  1. TPCK TRYPSIN
             │                             2. FBS
             ▼                         INFECT MDCK CELLS
    FREEZE STOCK OF                           │
    ALLANTOIC FLUID                           ▼
             │                          HARVEST VIRUS
             ▼                                │
    ┌──────────────────────────┐              ▼
    │ 1. HEMAGGLUTINATION ASSAY│◄─ ─ ─  ISOLATE RNA:
    │ 2. HA-INHIBITION ASSAY   │         A STRAINS-VIRAL RNA
    │ 3. VIRUS NEUTRALIZATION  │         B STRAINS-mRNA
    │    ASSAY                 │              │
    └──────────────────────────┘              ▼
                 ▲                      SYNTHESIZE cDNA:
                  \                     A STRAINS-UNIVERSAL
                   \                       PRIMER/VIRAL RNA
                    \                   B STRAINS-RANDOM
                     \                     PRIMERS/mRNA
                      \                       │
                       \                      ▼
                        \              PCR TO AMPLIFY TOTAL
                         \                   HA GENE
                          \                   │
                           \                  ▼
                            \        CLONE INTO E. coli PLASMID
                             \                │
        FIG. 1                \               ▼
                               \     SEQUENCE 5' END TO IDENTIFY
                                \    SIGNAL PEPTIDE SEQUENCE
                                 \            │
                                  \           ▼
                                   \  PCR TO AMPLIFY HA GENE MINUS
                                    \          SIGNAL
                                     \        │
                                      \       ▼
                                       \ CLONE INTO BACULOVIRUS
                                        \   RECOMBINATION VECTOR
                                         \    │
                                          \   ▼
                                           TRANSFECT INSECT CELLS;
                                           SELECT BACULOVIRUS
                                            EXPRESSION VECTOR
                                                │
                                                ▼
                                          PRODUCE rHA IN INSECT
                                              CELLS;
                                          PURIFY HA ANTIGEN
                                                │
                                                ▼
                              ┌─────────────────────────────────┐
                              │ ANIMAL AND HUMAN VACCINE STUDIES│
                              └─────────────────────────────────┘
```

VACCINE COMPRISING A BACULOVIRUS PRODUCED INFLUENZA HEMAGGLUTININ PROTEIN FUSED TO A SECOND PROTEIN

This is a continuation-in-part of U.S. Ser. No. 08/120,607 filed Sep. 13, 1993 by Gale E. Smith, Franklin Volvovitz, Bethanie E. Wilkinson, and Craig S. Hackett entitled "A Method for Producing Influenza Hemagglutinin Multivalent Vaccines" now U.S. Pat No. 5,769,939, issued Jun. 9, 1998.

BACKGROUND OF THE INVENTION

The present invention is generally in the area of recombinant influenza vaccines.

Epidemic influenza occurs annually and is a cause of significant morbidity and mortality worldwide. Children have the highest attack rate, and are largely responsible for transmission of influenza viruses in the community. The elderly and persons with underlying health problems are at increased risk for complications and hospitalization from influenza infection. In the United States alone, more than 10,000 deaths occurred during each of seven influenza seasons between 1956 and 1988 due to pneumonia and influenza, and greater than 40,000 deaths were reported for each of two seasons (Update: Influenza Activity—United States and Worldwide, and Composition of the 1992–1993 Influenza Vaccine, *Morbidity and Mortality Weekly Report.* U.S. Department of Health and Human Services, Public Health Service, 41/No. 18:315–323, 1992.) Influenza viruses are highly pleomorphic particles composed of two surface glycoproteins, hemagglutinin (HA) and neuraminidase (NA). The HA mediates attachment of the virus to the host cell and viral-cell membrane fusion during penetration of the virus into the cell. The influenza virus genome consists of eight single-stranded negative-sense RNA segments of which the fourth largest segment encodes the HA gene. The influenza viruses are divided into types A, B and C based on antigenic differences. Influenza A viruses are described by a nomenclature which includes the sub-type or type, geographic origin, strain number, and year of isolation, for example, A/Beijing/353/89. There are at least 13 subtypes of HA (H1–H13) and nine subtypes of NA (N1–N9). All subtypes are found in birds, but only H1–H3 and N1–N2 are found in humans, swine and horses (Murphy and Webster, "Orthomyxoviruses", in *Viroloqy*, ed. Fields, B. N., Knipe, D. M., Chanock, R. M., 1091–1152 (Raven Press, New York, (1990)).

Antibodies to HA neutralize the virus and form the basis for natural immunity to infection by influenza (Clements, "Influenza Vaccines", in Vaccines: New Approaches to Immunological Problems, ed. Ronald W. Ellis, pp. 129–150 (Butterworth-Heinemann, Stoneham, MA 1992)). Antigenic variation in the HA molecule is responsible for frequent outbreaks to influenza and for limited control of infection by immunization.

The three-dimensional structure of HA and the interaction with its cellular receptor, sialic acid, has been extensively studied (Wilson, et al, "Structure of the hemagglutinin membrane glycoprotein of influenza virus at 3A° resolution" *Nature* 289:366–378 (1981); Weis, et al, "Structure of the influenza virus hemagglutinin complexed with its receptor, sialic acid" *Nature,* 333:426–431 (1988); Murphy and Webster, 1990). The HA molecule is present in the virion as a trimer. Each monomer exists as two chains, HA1 and HA2, linked by a single disulfide bond. Infected host cells produce a precursor glycosylated polypeptide (HA0) with a molecular weight of about 85,000, which is subsequently cleaved into HA1 and HA2.

The presence of influenza HA-specific neutralizing IgG and IgA antibody is associated with resistance to infection and illness (Clements, 1992). Inactivated whole virus or partially purified (split subunit) influenza vaccines are standardized to the quantity of HA from each strain. Influenza vaccines usually include 7 to 25 micrograms HA from each of three strains of influenza.

The role of the other major surface glycoprotein, NA, in protective immunity of antibody or T-cell responses against influenza has not been defined. Neuraminidase is very labile to the process of purification and storage (Murphy and Webster, 1990) and the quantity of NA in the current influenza vaccines is not standardized. Purified HA but not NA vaccine prevents disease in animals challenged with influenza (Johansson, et al, "Purified influenza virus hemagglutinin and neuraminidase are equivalent in stimulation of antibody response but induce contrasting types of immunity to infection" *J. Virology,* 63:1239–1246 (1989)). An experimental vaccine based on neuraminidase antigen was not found to be protective in a human trial (Orga et al, *J. Infect. Dis.* 135:499–506 (1977)).

Licensed influenza vaccines consist of formalin-inactivated whole or chemically split subunit preparations from two influenza A subtype (H1N1 and H3N2) and one influenza B subtype viruses. Prior to each influenza season, the U.S. Food and Drug Administration's Vaccines and Related Biologicals Advisory Committee recommends the composition of a trivalent influenza vaccine for the upcoming season. The 1992–93 vaccine contained A/Texas/36/91-like(H1N1), A/Beijing/353/89-like(H3N2), and B/Panama/45/90 viruses. The FDA has advised that the 1993–94 influenza vaccine should contain the same Texas and Panama strains and a new influenza A Beijing strain (A/Beijing/32/92).

Vaccination of high-risk persons each year before the influenza season is the most effective measure for reducing the impact of influenza. Limitations of the currently available vaccines include low use rates; poor efficacy in the elderly and in young children; production in eggs; antigenic variation; and adverse reactions.

The Center for Disease Control (CDC) estimates that less than 30% of the individuals at high-risk for influenza are vaccinated each year (MMWR, 1992). The current inactivated vaccines achieve a high rate of protection against disease among normal healthy adults when the antigens of the vaccine and those of the circulating influenza viruses are closely related. Among the elderly, the rate of protection against illness is much lower, especially for those who are institutionalized (Clements, 1992). In a recent study by Powers and Belshe, *J. Inf. Dis.* 167:584–592 (1993), significant antibody responses to a trivalent subvirion influenza vaccine were observed in less than 30 percent of subjects 65 years old or older.

Seed viruses for influenza A and B vaccines are naturally occurring strains that replicate to high titers in the allantoic cavity of chicken eggs. Alternatively, the strain for the influenza A component is a reassortant virus with the correct surface antigen genes. A reassortant virus is one that, due to segmentation of the viral genome, has characteristics of each parental strain. When more than one influenza viral strains infect a cell, these viral segments mix to create progeny virion containing various assortments of genes from both parents.

Protection with current whole or split influenza vaccines is short-lived and wanes as antigenic drift occurs in epidemic strains of influenza. Influenza viruses undergo antigenic drift as a result of immune selection of viruses with amino acid sequence changes in the hemagglutinin molecule. Ideally, the vaccine strains match the influenza virus strains causing disease. The current manufacturing process for influenza vaccines, however, is limited by propagation of the virus in embryonated chicken eggs. Not all influenza virus strains replicate well in eggs; thus the viruses must be adapted or viral reassortants constructed. Extensive heterogeneity occurs in the hemagglutinin of egg-grown influenza viruses as compared to primary isolates from infected individuals grown in mammalian cells (Wang, et al, Virol. 171:275–279 (1989); Rajakumar, et al, Proc. Natl. Acad. Sci. USA 87:4154–4158 (1990)). The changes in HA during the selection and manufacture of influenza vaccines can result in a mixture of antigenically distinct subpopulations of virus. The viruses in the vaccine may therefore differ from the variants within the epidemic strains, resulting in suboptimal levels of protection.

Immediate hypersensitivity reactions can occur in persons with severe egg allergy due to residual egg protein in the vaccine. The 1976 swine influenza vaccine was associated with an increased frequency of Guillain-Barré syndrome. Subsequent vaccines prepared from other influenza strains have, thus far, not been observed to increase the occurrence of this rare disease.

A method of producing an influenza vaccine that does not require propagation in eggs would result in a purer product that would be less likely to cause an adverse immune reaction. In addition, a purer vaccine preparation would not require virus inactivation or organic extraction of viral membrane components, thereby avoiding denaturation of antigenic epitopes and safety concerns due to residual chemicals in the vaccine.

In addition, an influenza vaccine produced in the absence of egg propagation would avoid the genetic heterogeneity that occurs during adaptation and passage through eggs. This would result in a vaccine that is better matched with influenza epidemic strains, resulting in improved efficacy.

It is therefore an object of the present invention to provide a method of producing an influenza vaccine that does not require replication in eggs.

It is a further object of the present invention to provide a method of producing an influenza vaccine that is rapid and cost-efficient, highly purified and allows production of vaccines from primary sources of influenza.

SUMMARY OF THE INVENTION

A method of preparing a recombinant influenza hemagglutinin protein by expression in insect cells using a baculovirus expression system is provided. The resulting protein is useful in making a multivalent influenza vaccine based on a mixture of recombinant hemagglutinin antigens cloned from influenza viruses having epidemic potential. The recombinant hemagglutinin proteins are full length, uncleaved (HA0) glycoproteins including both the HA1 and HA2 subunits (HAO) purified under non-denaturing conditions to 95% or greater purity, preferably 99% purity.

A process for cloning influenza hemagglutinin genes from influenza A and B viruses using specially designed oligonucleotide probes and polymerase chain reaction (PCR) methodology is also disclosed. In the preferred embodiment, the cloned HA genes are modified by deletion of the nucleotides encoding the natural hydrophobic signal peptide sequences and replacement with a new baculovirus signal peptide, to yield a sequence encoding the signal peptide immediately abutting the hemagglutinin. These chimeric genes are introduced into baculovirus expression vectors so that the baculovirus polyhedrin promoter directs the expression of recombinant HA proteins in infected insect cells. The 18 amino acid baculovirus signal peptide directs the translation of rHA into the insect cell glycosylation pathway and is not present on the mature rHA glycoprotein. In the preferred embodiment, a vector is designed that does not encode any intervening amino acids between the signal peptide and hemagglutinin protein.

This methodology can be extended to all types of influenza viruses, including but not limited to the prevalent A (H1N1) sub-type, the A(H3N2) sub-type, and the B type that infect humans, as well as the influenza viruses which infect other mammalian and avian species.

A general approach for the efficient extraction and purification of recombinant HA protein produced in insect cells is disclosed for the purification of rHA proteins from A sub-types and B type influenza viruses. The recombinant vaccine can be developed from primary sources of influenza, for example, nasal secretions from infected individuals, rather than from virus adapted to and cultured in chicken eggs. This allows rapid development of vaccine directly from epidemic strains of influenza and avoids the problems arising from adaptation of the virus for culture in eggs, as well as patient reaction to egg contamination in the resulting vaccine.

Examples demonstrate the formulation and clinical efficacy of vaccine in an immunizing dosage form including purified rHA antigens from three strains of influenza virus recommended by the FDA for the 1993/1994 and 1994/1995 influenza epidemic seasons. Functional immunity was measured using assays that quantitate antibodies that bind to influenza hemagglutinin, that block the ability of influenza virus to agglutinate red blood cells, or that neutralize the influenza virus. Protective immune responses with rHA vaccines were measured in animals that are susceptible to influenza infection or in human challenge studies.

BRIEF DESCRIPTION OF THE DRAWINGS

FIG. 1 is a schematic of the cloning of HA genes from influenza A strains from purified viral RNA preparations, purification of expressed rHA, and biological characterization of rHA. Abbreviations: FDA, Food and Drug Administration; MDCK, Madin Darby Canine Kidney; TPCK, tosylphenylalanyl chloromethylketone; RNA, ribonucleic acid; cDNA, complementary deoxyribonucleic acid; HA, hemagglutinin; FBS, Fetal Bovine Serum; PCR, Polymerase Chain Reaction; and BV, Baculovirus.

DETAILED DESCRIPTION OF THE INVENTION

Figure 2:
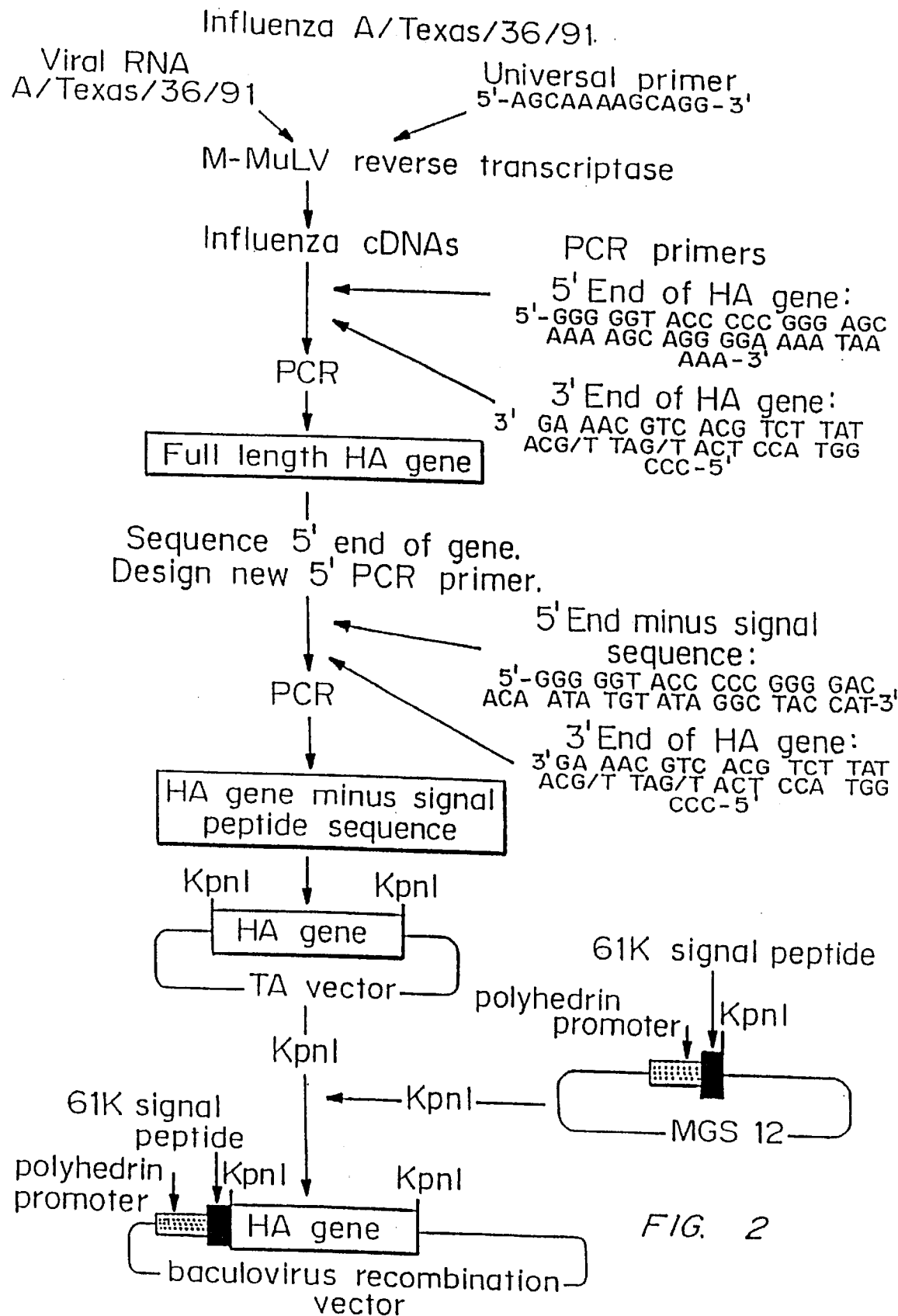
FIG. 2 is a more detailed schematic of the method of FIG. 1 applied to the cloning and expression of the HA gene of the Influenza A/Texas/36/91 strain. Influenza HA gene was obtained from RNA purified from MDCK cells infected with influenza A/Texas/36/91 using reverse transcriptase followed by two rounds of PCR amplification and cloning. The universal primer shown is set forth in SEQ ID NO. 1. The 5' and 3' primers shown in the first round of amplification are set forth respectively in SEQ ID NO. 2 and SEQ ID NO. 3. The 5' and 3' primers shown in the second round of amplification are set forth respectively in SEQ ID NO. 4 and SEQ ID NO. 3. A baculovirus recombination vector was constructed containing the polyhedrin promoter and a signal peptide sequence from the baculovirus 61 K gene (a baculovirus gene that encodes a signal peptide having a molecular weight of approximately 61,000), followed by the complete coding sequences for the mature HA protein. This recombination vector was then used to make a baculovirus expression vector that produces HA from this strain of the virus.

A method of preparing a recombinant influenza vaccine is described. A full length, uncleaved (HA0), hemagglutinin antigen from an influenza virus is produced with baculovirus expression vectors in cultured insect cells and purified under non-denaturing conditions. Two or more purified hemagglutinin antigens from influenza A and/or influenza B strains are mixed together to produce a multivalent influenza vaccine. The recombinant antigens may be combined with an adjuvant carrier for increased efficacy.

The use of recombinant DNA technology to produce influenza vaccines offers several advantages: a recombinant DNA influenza vaccine can be produced under safer and more stringently controlled conditions; propagation with infectious influenza in eggs is not required; recombinant HA protein can be more highly purified, virtually eliminating side effects due to contaminating proteins; purification procedures for recombinant HA do not have to include virus inactivation or organic extraction of viral membrane components, therefore avoiding denaturation of antigens and additional safety concerns due to residual chemicals in the vaccine; production of HA via recombinant DNA technology provides an opportunity to avoid the genetic heterogeneity which occurs during adaptation and passage through eggs, which should make it possible to better match vaccine stains with influenza epidemic stains, resulting in improved efficacy; and a recombinant approach may also allow for strain selection later in the year, thereby allowing time for selections based on more reliable epidemiological data.

Baculovirus Expression System.

Baculoviruses are DNA viruses in the family Baculoviridae. These viruses are known to have a narrow host-range that is limited primarily to Lepidopteran species of insects (butterflies and moths). The baculovirus Autographa californica Nuclear Polyhedrosis Virus (AcNPV), which has become the prototype baculovirus, replicates efficiently in susceptible cultured insect cells. AcNPV has a double-stranded closed circular DNA genome of about 130,000 base-pairs and is well characterized with regard to host range, molecular biology, and genetics.

Many baculoviruses, including AcNPV, form large protein crystalline occlusions within the nucleus of infected cells. A single polypeptide, referred to as a polyhedrin, accounts for approximately 95% of the protein mass of these occlusion bodies. The gene for polyhedrin is present as a single copy in the AcNPV viral genome. Because the polyhedrin gene is not essential for virus replication in cultured cells, it can be readily modified to express foreign genes. The foreign gene sequence is inserted into the AcNPV gene just 3' to the polyhedrin promoter sequence such that it is under the transcriptional control of the polyhedrin promoter.

Recombinant baculoviruses that express foreign genes are constructed by way of homologous recombination between baculovirus DNA and chimeric plasmids containing the gene sequence of interest. Recombinant viruses can be detected by virtue of their distinct plaque morphology and plaque-purified to homogeneity.

Baculoviruses are particularly well-suited for use as eukaryotic cloning and expression vectors. They are generally safe by virtue of their narrow host range which is restricted to arthropods. The U.S. Environmental Protection Agency (EPA) has approved the use of three baculovirus species for the control of insect pests. AcNPV has been applied to crops for many years under EPA Experimental Use Permits.

AcNPV wild type and recombinant viruses replicate in a variety of insect cells, including continuous cell lines derived from the fall armyworm, Spodoptera frugiperda (Lepidoptera; Noctuidae). S. frugiperda cells have a population doubling time of 18 to 24 hours and can be propagated in monolayer or in free suspension cultures.

Recombinant HA proteins can be produced in, but not limited to, cells derived from the Lepidopteran species Spodoptera frugiperda. Other insect cells that can be infected by baculovirus, such as those from the species Bombix mori, Galleria mellanoma, Trichplusia ni, or Lamanthria dispar, could also be used as a suitable substrate to produce recombinant HA proteins.

The most preferred host cell line for protein production from recombinant baculoviruses is Sf900+. Another preferred host cell line for protein production from recombinant baculoviruses is Sf9. Sf900+ and Sf9 are non-transformed, non-tumorigenic continuous cell lines derived from the fall armyworm, Spodoptera frugiperda (Lepidoptera; Noctuidae). Sf900+ and Sf9 cells are propagated at 28±2° C. without carbon dioxide supplementation. The culture medium used for Sf9 cells is TNMFH, a simple mixture of salts, vitamins, sugars and amino acids, supplemented with 10% fetal bovine serum. Aside from fetal bovine serum, no other animal derived products (i.e, trypsin, etc.) are used in cell propagation. Serum free culture medium (available as Sf900 culture media, Gibco BRL, Gaithersburg, Md.) can also be used to grow Sf9 cells and is preferred for propagation of Sf900+ cells.

Sf9 cells have a population doubling time of 18–24 hours and can be propagated in monolayer or in free suspension cultures. S. frugiperda cells have not been reported to support the replication of any known mammalian viruses.

It will be understood by those skilled in the art that the expression vector is not limited to a baculovirus expression system. The recombinant HA proteins can also be expressed in other expression vectors such as Entomopox viruses (the poxviruses of insects), cytoplasmic polyhedrosis viruses (CPV), and transformation of insect cells with the recombinant HA gene or genes constitutive expression.

Isolation of Influenza strains.

One or more influenza strains are isolated from individuals infected with the disease. Preferably, the influenza strains are those identified by the Food and Drug Administration (FDA) or CDC to have epidemic potential for the subsequent influenza season. An advantage of the method described herein is that clinical samples, such as nasal secretions, from patients infected with influenza can be used as a direct source of virus. Alternatively, they can be obtained from the FDA or CDC.

Propagation of Influenza strains.

The strains are then propagated in cells producing high viral titers, such as Madin Darby Canine Kidney (MDCK)

cells (available from the American Type Culture Collection under accession number ATCC CCL34). For example, MDCK cells are infected in the presence of tosylphenylalanyl chloromethylketone (TPCK) partially inactivated trypsin and fetal bovine serum concentrations optimized to produce the highest titers of first passage virus. The MDCK cells are infected with the influenza strains at a low multiplicity of infection (0.1 to 0.5) as determined by a standard HA assay (Rosen, "Hemagglutination with Animal Viruses" in *Fundamental Techniques in Virology*, ed. K. Habel and N. P. Salzman, pp. 276–28 (Academic Press, New York 1969), the teachings of which are incorporated herein). The infected cells are incubated at 33° C. for 48 hours, and the media assayed for virus production using the hemagglutination activity assay. The conditions yielding the highest HA activity are then used to prepare large stocks of influenza virus.

Purification of Virus.

Viral particles produced from the first passage are purified from the media using a known purification method such as sucrose density gradient centrifugation. For example, virus is harvested 24–48 hours post infection by centrifuging media of influenza infected MDCK cells. The resulting viral pellet is resuspended in buffer and centrifuged through a buffered sucrose gradient. The influenza virus band is harvested from the 40–45% sucrose region of the gradient, diluted with buffer and pelleted by centrifugation at 100,000×g. The purified virus pellet is resuspended in buffer and stored at −70° C.

Cloning of Influenza Hemagglutinin Genes.

An overview of the methods for cloning HA genes is provided in FIG. 1. Basically, cells are infected with the influenza strain to be cloned. Virus is harvested from the cell media and either viral RNA, for Influenza A strains, or mRNA, for Influenza B strains, is isolated. Viral RNA (-RNA) is extracted from purified virions and analyzed on formaldehyde agarose gels using standard procedures. cDNA is synthesized, using either an universal primer system for the viral RNA from the Influenza A strains or random primers for the mRNA from Influenza B strains. Plus-standard complimentary DNA (cDNA) is made using a universal oligonucleotide primer (5'-AGCAAAAGCAGG-3' (SEQ ID NO. 1)) which is homologous to all hemagglutinin RNA segments in influenza A and B viruses (Davis et al, "Construction and characterization of a bacterial clone containing the hemagglutinin gene of the WSN strain (H0N1) of influenza virus" *Gene*, 10:205–218 (1980)). Primers are designed that are homologous to conserved regions at the 5' and 3' end of influenza hemagglutinin genes. Both 5' and 3' primers also have restriction enzyme sites at the ends that are not found within the hemagglutinin genes.

The appropriate influenza A or B primers and influenza cDNA are mixed and the hemagglutinin gene segments amplified using standard PCR procedures. The resulting double-stranded DNA fragments contain entire mature hemagglutinin coding sequences. The polymerase chain reaction ("PCR") is used to amplify the total HA gene, which is then cloned into a suitable bacterial host such as *E. coli*. The 5' ends are sequenced to identify the signal peptide of the HA genes, then PCR is used to amplify the HA genes minus the signal peptide. This is then subcloned into a plasmid transfer vector containing the AcNPV polyhedrin promoter. The resulting transfer vectors contain the following 5'→3' sequences: Polyhedrin promoter from the baculovirus A. californica NPV, an ATG translational start codon, a 61 K baculovirus signal peptide, the coding sequences for mature hemagglutinin, the natural hemagglutinin translational termination codon, the polyhedrin RNA polyadenylation signal, and flanking baculovirus DNA.

A purified chimeric transfer plasmid DNA containing a cloned hemagglutinin gene is then mixed with AcNPV wild type DNA, co-precipitated with calcium and transfected into *S. frugiperda* cells. Recombinant baculoviruses are selected on the basis of plaque morphology and further purified by additional rounds of plaque-purification. Cloned recombinant baculoviruses are screened for hemagglutinin expression and a single baculovirus expression vector is selected to produce a Master Virus Bank.

Influenza A Strains:

HA genes from influenza A strains are cloned from purified viral RNA preparations. Viral RNA is extracted from 100–200 microliters of purified influenza A virions containing 1,000–2,000 hemagglutination units (HAU) of influenza. One HAU is the amount of virus that will agglutinate 50% of the red blood cells in the standard agglutination assay (Rosen, 1969). The virions are treated with proteinase K to digest protein, then the viral RNA is extracted with equal volumes of phenol and chloroform, and precipitated with ethanol in the presence of tRNA carrier. The viral RNA is resuspended in buffer and digested with RNAse-free DNAse to remove any contaminating DNA, then the extraction and precipitation steps repeated. Viral RNA (vRNA) is then analyzed using formaldehyde agarose gels as described by Maniatis, et al. Molecular Cloning: A Laboratory Manual. pp. 86–96 and 366–367 (Cold Spring Harbor Lab., Cold Spring, N.Y. 1982).

Influenza B Strains:

HA genes from influenza B strains are cloned from total messenger RNA (mRNA) extracted from cells infected with the influenza B-strain. Total RNA is then extracted from the infected cells. The harvested cells are lysed in the presence of guanidinium thiocyanate and total cell RNA is purified, using, for example, the RNA Extraction Kit from Pharmacia Biotech Inc. (Piscataway, N.J.) Total mRNA is extracted from cellular RNA using Oligo-(dT)-cellulose spun columns, using, for example, the mRNA Purification Kit from Pharmacia Biotech Inc.

Expression and Processing of Recombinant Hemagglutinin in Insect Cells.

Recombinant hemagglutinin antigens are expressed at high levels in *S. frugiperda* cells infected with AcNPV-hemagglutinin vectors. The primary gene product is unprocessed, full length hemagglutinin (rHA0) and is not secreted but remains associated with peripheral membranes of infected cells. This recombinant HA0 is a 68,000 molecular weight protein which is glycosylated with N-linked, high-mannose type glycans distinct from the glycans produced by expression of the viral proteins in mammalian or avian cells. There is evidence that rHA0 forms trimers post-translationally which accumulate in cytoplasmic membranes.

Vectors for Expression of HAO and other Proteins

HAO is a better vaccine due to its superior stability as compared to the HA1/HA2 complex, and maintains correct folding during purification and storage. The superior stability is particularly apparent with the B strains, resulting in titers that are about five fold greater than obtained with commercially available attenuated B strains.

As described below in the examples, when the HA genes were cloned in pMGS12 via restriction sites, the HA mature signal peptide was removed and replaced with the baculovirus chitinase signal peptide, referred to as the 61 kD signal peptide. Since the HA gene is connected to the chitinase signal peptide through a cleavage site, there are between three and five amino acids, depending on the restriction site selected, between the mature HAO protein and the 61 kD signal peptide. Although not a problem with the A strains of influenza, the B strain HAO expressed with the additional amino acids did not fold properly.

Two ways to overcome this problem were developed. The first is to use a new vector, pMGS3, which does not encode the 61 kD signal peptide. HAO with its native signal peptide is cloned into the vector and expressed. When characterized by SDS-PAGE, B strain HAO expressed in this vector shows better glycosylation and processing than when expressed in pMGS12. The HAO folded so well that it can be quantitatively converted to HA1/HA2. Unfortunately, as determined by Western blotting, the yield is not as high. The second method increases the yield by using the 61 kD signal peptide in pMGS12 to guide expression where the HAO gene was inserted without the use of restriction enzymes. The new vector, including the 61 kD signal peptide and HAO gene, without sequence encoding extraneous intervening amino acids, is referred to as pMGS27.

pMGS27 can be used for cloning and expression of any gene in a baculovirus expression system. The target gene, instead of being cloned into the vector by restriction and ligation, is cloned into the vector by annealing. Reagents are available from Clontech in their PCR-direct Cloning System. pMGS27 was designed so that it can be linearized at the end of the chitinase signal peptide coding region, and two long single-stranded tails created by treating the linearized pMGS27 with T4 DNA polymerase plus DATP.

The target gene is amplified using polymerase chain reaction ("PCR") or reverse transcriptase-PCR ("RT-PCR") with a pair of oligonucleotides designed to create single-stranded tails that are complementary to the tails of the treated pMGS27, after the PCR fragment has been treated with T4 DNA polymerase and dTTP. A simple annealing can then combine the two molecules into a circular plasmid which is ready to transform the host. Besides being quicker and simpler than the traditional restriction-ligation method of cloning a HA gene into pMGS12, the pMGS27 has the important advantage that it does not yield extra amino acids encoded by the restriction sites created between the chitinase signal peptide and the mature HA protein. These extra amino acids can sometimes create difficulties such that signal peptidase cannot cleave the signal or that the encoded protein does not fold correctly, as in the case of the B strain HA.

Purification of Recombinant HA0.

Several days post infection, rHA0 can be selectively extracted from the peripheral membranes of AcNPV-hemagglutinin infected cells with a non-denaturing, non-ionic detergent or other methods known to those skilled in the art for purification of recombinant proteins from insect cells, including, but not limited to affinity or gel chromatography, and antibody binding. The detergent soluble rHA0 can be further purified using DEAE ion exchange and lentil lectin affinity chromatography, or other equivalent methods known to those skilled in the art.

In a preferred embodiment, the rHAO is purified using a procedure that is more gentle and results in higher yield of the rHAO from B strains of influenza. This procedure is generally as follows:

The HAO protein which forms an integral part of the membrane of the insect cells is separated from the soluble proteins, the peripheral membrane proteins and the majority of the DNA and RNA by extraction of the cells in a relatively viscous alkaline solution, where an alkaline pH is defined as between about 9.5 and 10.5. Viscosity is increased through the inclusion of sucrose in a concentration of approximately 250 mM. A disulfide-reducing agent, for example, β-mercaptoethanol, is included in a concentration effective to prevent disulfide linking of proteins in the mixture. The cells are suspended in the extraction buffer, homogenized, and then centrifuged. The pellet is washed by homogenization in a low ionic strength buffer containing a disulfide-reducing agent at an alkaline pH (conductivity is generally less than 1 mS, pH 10.5) and the pellet centrifuged. The HAO is then extracted from the pellet in a buffer containing between 0.3 and 1.5% detergent such as Triton, an amount of disaggregating agent effect to prevent complex formation due to charge interactions, such as between 0.3 and 1.0M betaine or paurine, at an alkaline pH (9.5 is preferred). The HAO in the supernatant is then purified by anion exchange chromatography followed by cation exchange chromatography. The HAO is applied to the anion exchange column, for example, DEAE or Q-Sepharose® (an agarose bead column with quaternary amine groups), in the same buffer as extracted but diluted at least 1:2 with additional buffer, after equilibration of the column in buffer containing approximately ¹⁄₁₀th the concentration of detergent and disulfide-reducing agent. The HAO is then eluted by lowering the pH to approximately 8.5. The eluted HAO is applied to a cation exchange column in essentially the same buffer. Contaminants are eluted by lowering the pH to approximately 7.4, then eluting the HAO by increasing the salt concentration to 0.15M NaCl.

This preferred method of purification is described in detail as follows.

Preparation of the Recombinant HA-Containing Membrane Fraction.

Recombinant HA expressing cells (6.2 g of cells from 0.34 L of culture) are suspended at 100 mg/mL in ice-cold 100 mM sodium pyrophosphate, 100 mM sodium chloride, 250 mM sucrose, 0.1% β-mercaptoethanol, pH 10.5. The cells are disrupted using a Polytron® homogenizer (Brinkman Instruments Inc., Westbury, N.Y.) at a setting of 4 for 2 min. Alkaline pH of the homogenization medium is needed to increase the solubility of the contaminating proteins and to increase the purity of the membrane preparation. The homogenate is centrifuged for 30 min. at 9,200 g. The supernatant is discarded and the pellet collected. Preparation of the membrane fraction is followed by a low-ionic strength wash step. The pellet is resuspended to the original volume in the ice-cold 0.1% β-mercaptoethanol, 10.5, and homogenized using a Polytron® homogenizer at a setting of 4 for 2 min. The homogenate is centrifuged for 30 min. at 9,200 g. The supernatant is discarded and the pellet collected. This low-ionic strength wash removes additional portion of the peripheral membrane proteins. The preparation of the membrane fraction results in the considerable enrichment in the recombinant HA and in the removal of contaminating nucleic acids.

Extraction of the Recombinant HA.

The recombinant HA is then selectively extracted from the membrane pellet under conditions that do not denature the antigen. The membrane pellet is homogenized in 41 mL of ice-cold 10 mM ethanolamine pH 9.5, 1% Triton N101, 0.1% β-mercaptoethanol, 25 mM NaCl, 400 mM betaine using a Polytron homogenizer at a setting of 4 for 2 min. After incubation for 40 min. at 23° C., the mixture is centrifuged for 30 min. at 9,200 g. The supernatant containing recombinant HA is decanted and diluted two-fold with the same buffer.

Proteins are analyzed by SDS polyacrylamide gel electrophoresis. Samples are disrupted in a boiling water bath for 10 minutes in the presence of 2% sodium dodecyl sulfate (SDS) and 5% β-mercaptoethanol, then electrophoresed on an 11% polyacrylamide gel in the presence of 0.1% SDS, then stained with Coomassie blue.

Chromatographic Purification.

Chromatographic purification of the recombinant HA was simplified and expensive affinity chromatography on Lentil Lectin Sepharose was eliminated from the process by substitution with a two-step chromatographic purification process which results in a highly purified recombinant HA antigen that is non-denatured and suitable as a component of an influenza vaccine for human use. The chromatography gel matrices used are Pharmacia Q-Sepharose® Fast Flow and CM-Sepharose Fast Flow®.

Anion-Exchange Chromatography.

All chromatography is performed at room temperature. The recombinant HA-containing extract prepared as described above is applied at 1 mL/min to Pharmacia Q-Sepharose Fast Flow® (5 mL in a C10/10 Pharmacia column) equilibrated with 10 mM ethanolamine pH 9.5, 0.1% Triton® N101, 0.01% β-mercaptoethanol, 25 mM NaCl, 400 mM betaine. The column is then washed with the equilibration buffer until the UV absorbance of the effluent returns to the baseline. Under these conditions recombinant HA binds to the column while part of the contaminants flow through. Partially purified recombinant HA is then eluted with 30 mM diethanolamine pH 8.5, 0.1% Triton® N101, 0.01% β-mercaptoethanol, 25 mM NaCl, 400 mM betaine.

Cation Exchange Chromatography.

The Q-Sepharose eluate (23 mL) is diluted two-fold with 30 mM diethanolamine pH 8.5, 0.1% Triton® N101, 0.01% β-mercaptoethanol, 10 mM NaCl, 400 mM betaine. The column is then washed with 35 mL of 10 mM sodium phosphate pH 7.4, 0.1% Triton® N101, 0.01% β-mercaptoethanol, 10 mM NaCl, 400 mM betaine. This treatment elutes the contaminants from the column while recombinant HA remains bound to the CM Sepharose. The detergent is then removed by washing the column with 10 mM sodium phosphate pH 7.4, 10 mM NaCl until the UV absorbance of the effluent returned to the baseline. Purified recombinant HA is eluted with phosphate buffer saline, pH 7.5 (PBS).

Purified rHA0 is resuspended in an isotonic, buffered solution. Following the removal of the detergent, purified rHA0 will efficiently agglutinate red blood cells.

Structural and Biological Properties of Recombinant HA0.

rHA0 is purified to at least 95% purity, more preferably 99% purity. This migrates predominantly as a single major polypeptide of 68,000 molecular weight on an SDS-polyacrylamide gel. The quaternary structure of purified recombinant HA0 antigen was examined by electron microscopy, trypsin resistance, density sedimentation analysis, and ability to agglutinate red blood cells. These data show that recombinant HA0 forms trimers, which assemble into rosettes.

Purified rHA0 does not agglutinate cells prior to removal of detergent, suggesting that the antigen must form complexes (rosettes) in order to cross-link chicken red blood cells. The quantitative ability of purified rHA0 to agglutinate cells is used as a measure of lot-to-lot consistency of the antigen. One hemagglutinin unit is defined as the quantity of antigen required to achieve 50% agglutination in a standard hemagglutinin assay with chicken red blood cells. Comparative data shows that purified rHA0 antigens agglutinate red blood cells with an efficiency comparable to that observed with whole influenza virions.

The recombinant HA0 can be cleaved at the disulfide bond, causing a conformation change that results in the formation of two chains, HA1 and HA2 as described by Carr, C. M. and Kim, P. S., "A Spring-loaded Mechanism for the Conformational Change of Influenza Hemagglutin", Cell 73:823–832 (1993), which is incorporated by reference herein. Cleavage of recombinant HA0 is described in more detail below in Example 6. It is believed that, upon cleavage of natural HA0 into HA1 and HA2, the chains become infectious by acquiring the ability to fuse with a cell, thereby creating an improved immune response. The processing of antigens such as influenza hemagglutin occurs by the binding of antigenic peptides to major histocompatibility (MHC) molecules. The antigen/MHC complex is recognized by T cells to initiate an immune response as described in the review by Harding and Geuze, Current Opinion in Cell Biology 5:596–605 (1993), which is incorporated by reference herein. The rHA0 produced in a baculovirus, however, is highly stable and immunogenic as the intact molecule. Comparison of the sugar molecules on the HA0 expressed in insect cells shows that the glycans are different from those when the HA0 is expressed in mammalian or avian cells.

Production of Fusion Proteins

Fusion proteins consisting of the HA0 fused to a second antigenic protein can be made where the antigenicity of the second protein is low or there are advantages to eliciting an immunogenic response to multiple antigens. An example of a preferred second antigen is the neuraminidase produced by influenza. The antigen can consist of a cellular, viral, or bacterial protein, or antigenic portion thereof including at least five to eight amino acids. Other antigens include hepatitis B antigen, HIV antigens, and carcinoembryonic antigen. An "immune response", as used herein, refers to either a humoral response, measured by the production of antibody to the antigen, or a cellular response, measured by the elicitation of a T cell mediated response to the antigen. In some cases a "linker" of non-antigenic amino acids may be inserted between the HA and the antigen, to further enhance antigenicity of the antigen as compared to the HA. The process involves constructing a DNA plasmid for fusing target antigen genes to full-length or fragments of the influenza virus HA gene, using oligonucleotide probes and polymerase chain reaction (PCR) methodology.

The HA-target antigen fusion genes are modified for proper expression in insect cells by deletion of the natural hydrophobic signal peptide sequences and replacement with a new baculovirus signal peptide. The fusion gene is introduced into a baculovirus expression vector so that the baculovirus polyhedron promoter directs the transcription of the fusion proteins in infected insect cells. The 18 amino acid baculovirus signal peptide directs the translation of the HA-target antigen fusion polypeptide into the insect cell glycosylation pathway and is not present on the mature fusion protein.

For example, Plasmid pA9440, which contains the A/Beijing/32/92 strain HA gene in the pMGS12 baculovirus transfer plasmid described below, was used as a template for the amplification of the HA gene by polymerase chain reaction (PCR) using the protocol recommended by the supplier (Gene Amp PCR cloning kit, Perkin Elmer Cetus). The PCR reaction mixture (100 µl) contained 20 pmol of primers designed to anneal to portions of the HA gene. The 5' and 3' primers were designed with restriction endonuclease sites at the ends that are not found within the HA gene. The 5' PCR primer (0–567) for the HA0 and HA1 fragments begins 52 base pairs downstream from the 5' end of the natural HA gene coding sequences, deleting the natural signal peptide sequence, and adds a SmaI site immediately 5' to the HA coding sequences. The 5' PCR primer (0–651) for the HA2 fragment begins at nucleotide 1108 of the natural HA gene, immediately following the codon encoding the arginine residue that is removed during cleavage of HA1 to HA1 and HA2. The 3' PCR primer (0–680) for the HA0 and HA2 fragments was designed to add a KpnI site immediately following the HA coding sequences, removing the natural stop codon. The 3' PCR primer for HA1 (0–679) truncates the gene immediately prior to the arginine residue removed during HA0 cleavage. Amplification of the HA gene fragment was carried out for 30 cycles each consisting of 1 min. at 94° C. for denaturation, 2 min. at 55° C. for annealing of the primers, and 2 min. at 72° C. for extension. The resulting amplified HA gene fragments were electrophoresed on agarose gels, purified from the gel using a GeneClean kit (Bio 101, Inc.), and ligated into a plasmid designed to accept PCR-generated fragments (pCRII; Invitrogen). Thus, plasmids pB142, pB144, and pB330, which contain the HA0, HA1, or HA2 gene fragments, respectively, were obtained.

The HA gene fragments were removed from plasmids pB142, pB144, and pB330 with SmaI and KpnI restriction enzymes and then subcloned by standard recombinant DNA techniques (Sambrook et al., 1989) into the AcNPV transfer plasmid pMGS12. The pMGS12 plasmid contains, from 5' to 3', the AcNPV polyhedron promoter, an ATG initiation codon, the sequence for a cleavable signal peptide from a 61,000 molecular weight baculovirus glycoprotein (61 K), SmaI and KpnI restriction enzyme cloning sites, and a TAA universal stop codon sequence. Flanking these regulatory regions is DNA from the EcoRI I fragment from the AcNPV genome (Summers and Smith, "A manual of methods for baculovirus vectors and insect cell culture procedures". Texas Agricultural Experimental Station Bulletin No. 1555 (1987). The cloned HA PCR fragments were excised from the pCRII cloning vector with SmaI and KpnI, purified with agarose gel electrophoresis and the GeneClean kit, and ligated into pMGS12 that had also been digested with SmaI and KpnI. The resulting AcNPV transfer plasmids, pB879, pB1201, and pB1205, contained the coding regions for HA0, HA1, or HA2, respectively, linked in frame with the cleavable baculovirus signal peptide from the 61 K gene and the polyhedron promoter. The pB879, pB1201, and pB1205 AcNPV transfer plasmids may be used to fuse HA0, HA1, or HA2 to any gene of interest.

The second step in the construction of HA-CEA fusion gene transfer plasmids was to insert the CEA coding sequences into the HA-encoding constructs. Restriction endonuclease recognition/cleavage sites for SmaI and KpnI were placed at both ends of the CEA gene through PCR amplification of plasmid pA9080. The 5' PCR primer, 0–649, begins 82 base pairs from the 5' end of the gene, deleting the natural CEA signal peptide sequence. The 3' PCR primer, 0–650, was designed to delete the last 72 basepairs at the 3' end of the gene which codes for the hydrophobic C-terminal region sequence. Amplification of the CEA gene fragment was carried out for 30 cycles, each consisting of 1 min. at 94° C. for denaturation, 2 min. at 55° C. for reannealing, and 2 min. at 72° C. for extension. The resulting amplified CEA gene fragment was electrophoresed on an agarose gel, purified with the GeneClean procedure, and ligated into pCRII (Invitrogen) according to the manufacturers' instructions. The resulting plasmid, pB806, contains the CEA gene without its natural signal peptide, C-terminal hydrophobic domain, or stop codon, but with both SmaI and KpnI sites at both ends of the gene.

A large-scale plasmid prep was performed with the pB806 plasmid, and the DNA was digested either with Sma I or Kpn I. The CEA-encoding fragments were purified with agarose gel electrophoresis and the GeneClean kit, and the purified fragments were ligated into each of the three HA-encoding constructs (pB879, pB1201, or pB1205) digested with the same restriction enzyme. For example, CEA-encoding fragments with SmaI-cut ends were ligated into the HA0-, HA1-, and HA2-encoding constructs (pB879, pB1201, and pB1205, respectively) cut with SmaI to create plasmids pB1250, pB1555, and pB1584, respectively. CEA-encoding fragments with KpnI-cut ends were ligated into the HA0-, HA1-, and HA2-encoding constructs cut with KpnI to create pB1264, pB1564, and pB1593. Insertion of the CEA gene at the SmaI site placed the CEA coding sequences downstream of the HA coding sequences. For all constructs, the PCR primer were designed such that the EA gene was inserted in-frame with HA, and the fusion gene translation would be terminated at the universal translation termination signal (TAATTAATTAA) (Sequence ID No. 4) in the pMGS12 vector sequences downstream of the KpnI site.

This construct may be improved by deletion of intervening amino acids, either between the signal peptide and HAO, as described below, or between the HAO and the fusion gene, to enhance folding and immunogenicity.

Formulation and Packaging of Vaccines

The rHA can be formulated and packaged, alone or in combination with other influenza antigens, using methods and materials known to those skilled in the art for influenza vaccines. In a preferred embodiment, HA proteins from two A strains and one B strain are combined to form a multivalent vaccine.

In a particularly preferred embodiment, the HAs are combined with an adjuvant, in an amount effective to enhance the immunogenic response against the HA proteins. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, new chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the protein within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N. H.) should also be useful.

In the preferred embodiment, the vaccine is packaged in a single dosage for immunization by parenteral (i.e., intramuscular, intradermal or subcutaneous) administration or nasopharyngeal (i.e., intranasal) administration. The effective dosage is determined as described in the following examples. The carrier is usually water or a buffered saline, with or without a preservative. The antigen may be lyophilized for resuspension at the time of administration or in solution.

The carrier may also be a polymeric delayed release system. Synthetic polymers are particularly useful in the formulation of a vaccine to effect the controlled release of antigens. An early example of this was the polymerization of methyl methacrylate into spheres having diameters less than one micron to form so-called nano particles, reported by Kreuter, J., *Microcapsules and Nanoparticles in Medicine and Pharmacology*, M. Donbrow (Ed). CRC Press, p. 125–148. The antibody response as well as the protection against infection with influenza virus was significantly better than when antigen was administered in combination with aluminum hydroxide. Experiments with other particles have demonstrated that the adjuvant effect of these polymers depends on particle size and hydrophobicity.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d,l-lactide-co-glycolide) (PLGA). This is a biodegradable polyester that has a long history of medical use in erodible sutures, bone plates and other temporary prostheses, where it has not exhibited any toxicity. A wide variety of pharmaceuticals including peptides and antigens have been formulated into PLGA microcapsules. A body of data has accumulated on the adaptation of PLGA for the controlled release of antigen, for example, as reviewed by Eldridge, J. H., et al. *Current Topics in Microbiology and Immunology.* 1989, 146: 59–66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

The present invention will be further understood by reference to the following non-limiting examples.

EXAMPLE 1

Propagation and Purification of Influenza Viruses

The following influenza vaccine strains were obtained from the FDA in chicken egg allantoic fluid:
A/Beijing/353/89-like(H3N2)
A/Beijing/32/92-like(H3N2)
A/Texas/36/91-like(H1N1)
B/Panama/45/90

To propagate the original stock of influenza virus obtained from the FDA, MDCK cells were infected in the presence of TPCK-treated trypsin (Sigma Chemical Co., St. Louis, Mo.) and fetal bovine serum concentrations optimized to produce the highest titers of first passage virus. The MDCK cells were infected with the influenza strains at a low multiplicity of infection (0.1 to 0.5) as determined by a standard HA assay (Rosen, "Hemagglutination with Animal Viruses" in *Fundamental Techniques in Virology*, ed. K. Habel and N. P. Salzman, pp. 276–28 (Academic Press, New York 1969)). The infected cells were incubated at 33° C. for 48 h. and media was assayed for virus production using the hemagglutination activity assay. The conditions yielding the highest HA activity were used to prepare large stocks of influenza virus. The optimum concentrations of TPCK trypsin and fetal bovine serum for the above influenza viruses are listed in Table 1.

TABLE 1

Optimum Concentration of TPCK Trypsin and Fetal Bovine Serum.

|  | A/Beijing/ 353/89 | A/Beijing/ 32/92 | A/Texas/ 36/91 | B/Panama/ 45/90 |
|---|---|---|---|---|
| % Fetal Bovine Serum | 0.25% | 0.25% | 0.25% | 5.0% |
| Amount TPCK Treated Trypsin | 45 µ/ml | 45 µg/ml | 45 µ/ml | 3 µ/ml |

Purification of Influenza Virus:

Virus was harvested 24–48 hours post infection from 10 T175 tissue culture flasks by clarifying media (1,000×g for 10 minutes) of influenza infected MDCK cells. The virus was pelleted from the media at 100,000×g for 1 hour. The resulting viral pellet was resuspended in 1 ml phosphate buffered saline (PBS) pH 7.4 and centrifuged through a 20 ml 20–60% (w/v) sucrose gradient in PBS. The influenza virus band was harvested from the 40–45% sucrose region of the gradient, diluted with PBS and pelleted at 100,000×g. The purified virus pellet was resuspended in 0.5 ml PBS stored at −70° C.

EXAMPLE 2

Cloning of Influenza A/Texas/36/91 HA Gene

A specific example of the cloning step for one of the influenza HA genes is shown in FIG. 2. Viral RNA was extracted as described above from Influenza A/Texas/36/91, obtained from the CDC. The universal primer complementary to the 3' end of influenza RNA segments 5'-AGCAAAAGCAGG-3' (SEQ ID NO. 1) was used with murine Maloney Leukemia Virus (M-MuLV) reverse transcriptase to produced influenza cDNAs. Purified viral RNA or mRNA (5 µg) was used as a template to make cDNA utilizing M-MuLV reverse transcriptase supplied in the First-Strand cDNA Synthesis Kit by Pharmacia Inc. The primer used for cDNA of viral RNA from influenza A strains was a synthetic oligonucleotide primer (5'-AGCAAAAGCAGG-3') (SEQ ID NO. 1), which is homologous to the 3' end of all HA gene virion segments.

Amplification of HA genes from cDNA was done by polymerase chain reaction (PCR) using standard reaction conditions (Gene Amp kits; Cetus/Perkin Elmer, Norwalk, Conn.). The PCR reaction mixture (100 µl) contained 20 pmol of primers specific for 5' and 3' ends of the HA gene of influenza A (H3) or A (H1) or influenza B strains as determined by consensus sequences found in GenBank DNA data files, as shown in Table 2. Amplification was carried out for 30 cycles with each cycle consisting of 1 minute of denaturation at 94° C., 2 minutes at 55° C. for reanealing and 3 minutes at 72° C. for extension. The PCR products were analyzed on 0.8% agarose gels for correct size before cloning.

PCR primers from the 5' end of the HA gene: 5'-GGG GGT ACC CCC GGG AGC AAA AGC AGG GGA AAA TAA AAA-3' (SEQ ID NO. 2) and 3' end of the HA gene: 3'-GA AAC GTC ACG TCT TAT ACG/T TAG/T ACT CCA TGG CCC-5' (SEQ ID NO. 3) were used in the PCR to yield the full length HA gene.

A new 5' PCR primer was designed from the 5' end of the gene: 5' end minus signal sequence: 5'-GGG GGT ACC CCC GGG GAC ACA ATA TGT ATA GGC TAC CAT-3' (SEQ ID NO. 4) and the 3' end of the gene: 3'-GA AAC GTC ACG TCT TAT ACG/T TAG/T ACT CCA TGG CCC-5' (SEQ ID NO. 3). These were used in PCR to yield the HA gene minus the signal peptide sequence. This was then inserted into the TA vector cleaved with KpnI. The 61 K signal peptide for baculovirus expression and the polyhedrin promoter were then inserted into the TA vector containing the HA gene minus influenza signal peptide sequence. The resulting baculovirus recombination vector contains the polyhedrin promoter, 61 K baculovirus signal peptide, and HA gene for Influenza A/Texas/36/91.

HA genes from influenza B strains were cloned from total messenger RNA (mRNA) extracted from MDCK cells infected with the influenza B-strain B/Panama/45/90. Total RNA was prepared from 5 T175 flasks of infected cells. The harvested cells were lysed in the presence of guanidinium thiocyanate and total cell RNA was purified as described above. Total mRNA was extracted from cellular RNA using Oligo-(dT)-cellulose spun columns as described above.

The primer used for mRNA from influenza B strains was a random oligonucleotide DNA primer (Pharmacia, Inc.).

combined in the reaction mixture with the universal single stranded DNA primer 5'-AGCAAAAGCAGG-3' (SEQ ID NO. 1). This primer is complementary to the 3' end of influenza virion segments, as described above. The reaction also contained the addition of [$\alpha$-$^{32}$P]dCTP to visualize the cDNA products which were separated on 1.5% alkaline hydrolysis gel (Maniatis, et al, 1982) and exposed to X-OMAT-AR film.

EXAMPLE 3

Cloning HA Genes Into Bacterial Plasmids

The PCR amplified rHA genes were cloned into a pUC-like plasmid vector using the TA Cloning System (Invitrogen, Inc.). The presence of HA genes were verified by restriction enzyme digest analysis of plasmid DNA purified by standard procedures (Maniatis, et al, 1982). The 5' end of the rHA genes were then analyzed by DNA sequencing and new primers were designed to remove the sequences coding for the hydrophobic signal peptides at the N-terminus HA proteins. The specific 5' and 3' oligonucleotide primers listed in Table 2 were then used to amplify cDNA products by PCR and cloned into E. coli TA plasmid vectors (Invitrogen, Inc.) using standard cloning methods. The resulting DNA clones contained coding sequences for the mature HAs.

The rHA genes from A/Texas/36/91, A/Beijing/353/89, A/Beijing/32/92, and B/Panama/45/90 were subcloned by standard procedures (Maniatis et al, 1982) into baculovirus expression vectors. The HA genes were removed from the TA cloning plasmids with the appropriate restriction enzymes and the purified HA DNA fragment inserted into a baculovirus recombination plasmid. The resulting bacterial clones were screened for ampicillin resistance and then cut

TABLE 2

Primers Used for PCR Amplification.

A/Beijing/32/93

| | | | | | | | | | | | | | |
|---|---|---|---|---|---|---|---|---|---|---|---|---|---|
| 5' end gene, SEQ ID NO: 5 | 5' GGG | GGA TCC BamH1 | GGT ACC Kpn1 | AGC | AAA | AGC | AGG | GGA | TAA | TTC | TAT 3' | | |
| 5' end minus HA signal peptide, SEQ ID NO: 27 | GGG | GGT ACC Kpn1 | CCC GGG Sma1 | GAC | TTT | CCA | GGA | AAT | GAC | AAC | AG 3' | | |
| 3' end, SEQ ID NO: 28 | 3' TAA | TTA | ATT | TTT | GTG | GGA | ACA | AAG | ATC | CTA | CTA | AGC | CAT GGC Kpn1 | CC 5' |

A/Texas/36/91

| | | | | | | | | | | | | |
|---|---|---|---|---|---|---|---|---|---|---|---|---|
| 5' end gene, SEQ ID NO: 2 | 5' GGG | GGT ACC Kpn1 | CCC GGG Sma1 | AGC | AAA | AGC | AGG | GGA | AAA | TAA | AAA 3' | |
| 5' end minus HA signal peptide, SEQ ID NO: 4 | 5' GGG | GGT ACC Kpn1 | CCC GGG Sma1 | GAC | ACA | ATA | TGT | ATA | GGC | TAC | CAT 3' | |
| 3' end, SEQ ID NO: 3 | 3' GA | AAC | GTC | ACG | TCT | TAT | ACG/T | TAG/T | ACT | CCA TGG Kpn1 | CCC 5' | |

B/Panama/45/90

| | | | | | | | | | | | | | | |
|---|---|---|---|---|---|---|---|---|---|---|---|---|---|---|
| 5' end gene, SEQ ID NO: 29 | 5' GGG | GAA TTC EcoR1 | GGT ACC Kpn1 | CCC GGG Sma1 | AAG | GCA | ATA | ATT | GTA | CTA | CTC | ATG | GT 3' | |
| 5' end minus HA signal peptide, SEQ ID NO: 30 | 5' GGT ACC Kpn1 | CCC Sma1 | GGG | GAT | CGA | ATC | TGC | ACT | GGG | ATA | ACA 3' | | | |
| 3' end, SEQ ID NO: 31 | 3' TG | TTA | CAA | AGA | ACA/G | AGG | TAG | ACA | GAC | ACT | CCA TGG Kpn1 | CCT AGG BamH1 | CTT AAG EcoRI | GGG 5' |

An example of cDNA synthesis products used influenza virus A/Texas/36/91 viral RNA as a template. The location of the cDNA segments that code for the influenza proteins could be determined as follows. Purified viral RNA was with restriction enzymes to release the inserted HA gene to confirm is presence. The recombination plasmids containing HA genes were purified on cesium chloride-ethidium bromide gradients (Maniatis, et al, 1982). The 5' end of the plasmids were sequenced to determine the presence of the correct baculovirus signals (AcNPV polyhedrin promoter, ATG translational start signal and baculovirus signal peptide sequence) and proper HA coding sequence in the correct reading frame. The DNA sequences at the 5' end of the HA genes and flanking AcNPV polyhedrin promoter and baculovirus signal peptide (first 18 amino acids of each amino acid sequence) are shown as SEQUENCE LISTINGS.

SEQ ID NO. 6 encodes the 5' end sequence of the HA gene for A/Beijing/32/92 (sequence range 1–481). SEQ ID NO. 7 is the corresponding amino acid sequence (beginning at the start codon "ATG" [nucleotide 21] of SEQ ID NO. 6). The amino acid sequence of the 61 K signal peptide is set forth in SEQ ID NO. 7 as amino acids 1–18.

SEQ ID NO. 8 encodes the 5' end sequence of the HA gene for A/Texas/36/91 (sequence range 1–481). SEQ ID NO. 9 is the corresponding amino acid sequence (beginning at the start codon "ATG" [nucleotide 21] of SEQ ID NO. 8). The amino acid sequence of the 61 K signal peptide is set forth in SEQ ID NO. 9 as amino acids 1–18.

SEQ ID NO. 10 encodes the 5' end sequence of the HA gene for B/Panama/45/90 (sequence range 1–434). SEQ ID NO. 11 is the corresponding amino acid sequence (beginning at the start codon "ATG" [nucleotide 21] of SEQ ID NO. 10). The amino acid sequence of the 61 K signal peptide is set forth in SEQ ID NO. 11 as amino acids 1–18.

In SEQ ID NOs 6, 8, and 10, nucleotides 1–20 are the 3' end of the polyhedrin promoter, nucleotides 21–74 encode the 61 K signal peptide, and nucleotides 75 to the end encode the 5' end of the HA gene.

EXAMPLE 4

Expression of Recombinant HA in Insect Cells

The chimeric recombination plasmids containing cloned HA genes were purified and 2 μg was mixed with 1 μg AcNPV wild type DNA. The DNAs were co-precipitated with calcium and transfected into S. frugiperda cells using standard procedures (Smith, Summers, and Fraser, Mol. and Cell. Biol. 3:2156–2165 (1983)). Recombinant baculoviruses were identified on the basis of plaque morphology then further purified by additional rounds of plaque-purification. Plaque-purified recombinant baculoviruses are screened for expression of rHA and a single baculovirus expression vector was selected for further development.

S. frugiperda cells were infected with a baculovirus vector containing the HA gene from the Influenza strain: B/Panama/45/90. At 24, 48, and 72 hours post infection, $1\times10^6$ cells were pulsed with 25 μCi [$^{35}$S]methionine for 15 minutes to label proteins being synthesized. The cells were collected and the proteins separated on an 11% polyacrylamide gel in the presence of 0.1% SDS. The radiolabeled proteins were detected by exposure to X-OMAT-AR film. The location of protein standards and their size in kilodaltons (kd) indicated that the 85 kd recombinant HA protein is one of the major proteins being synthesized in the cells at 48 hours and 72 hours post infection.

EXAMPLE 5

Production and Purification of Recombinant HA

The baculovirus expression vector A8611, which contains the gene for influenza A/Beijing/353/89, produced essentially as described above for A/Beijing/32/92 hemagglutinin under the control of the polyhedrin promoter, was used to infect S. frugiperda cells. Cells were grown at 27° C. to a density of $1\times10^6$ cells/mL in TNMFH media (Gibco BRL, Gaithersburg, Md.) supplemented with 10% fetal bovine serum, and infected at a multiplicity of infection (MOI) of 1 with the A8611 recombinant baculovirus. During infection the influenza A/Beijing/353/89 hemagglutinin is produced under the transcriptional control of the baculovirus polyhedrin promoter. Cells are harvested 72 hours post-infection by centrifugation for 15 minutes at 3,400×g, and washed by resuspension in serum-free TNMFH media followed by centrifugation for 30 minutes at 10,400×g. The supernatant is decanted, and infected cell pellets are stored at −70° C.

A process was developed in which the recombinant HA is selectively extracted from the infected cells under conditions that do not denature the antigen. Unless noted, all extraction steps are performed at 4° C. The cell pellet from 0.5 L of culture (approximately $5\times10^8$ cells) was disrupted for 2 minutes in 40 mL of ice-cold 30 mM Tris-HCl, pH 8.4, 25 mM LiCl, 1% (v/v) TWEEN-20™ detergent (polyethylene (20) sorbitan monolaurate detergent), 1 mg/mL leupeptin, using a Polytron™ homogenizer (Brinkmann Instruments Inc. Westbury, N.Y.). The homogenate was centrifuged for 30 minutes at 9,200×g. The supernatant was discarded, and the pellet collected. This step removes soluble and peripheral membrane proteins from the insect cells without extraction of integral membrane proteins like rHA. To extract the rHA the pellet was homogenized for 2 minutes at a setting of 4 in 40 mL of ice-cold 30 mM Tris, 10 mM ethanolamine, pH 11, 25 mM LiCl, 2% Tween-20. After a 60 minute incubation on ice, the pH of the homogenate was adjusted to 8.4 with 1N HCl, and insoluble material was removed by centrifugation for 30 minutes at 9,200×g. The supernatant containing the soluble rHA was decanted, and the pH was checked and, if necessary, adjusted to 8.4 at room temperature. The insoluble material was resuspended in 40 mL of water for analysis. The HA integral membrane protein was solubilized under the high pH, Tween-20 detergent conditions and remains in solution after the pH is dropped.

Proteins were analyzed by SDS polyacrylamide gel electrophoresis. Samples were disrupted in a boiling water bath for 10 minutes in the presence of 2% sodium dodecyl sulfate (SDS) and 5% beta-mercaptoethanol, then electrophoresed on an 11% polyacrylamide gel in the presence of 0.1% SDS, then stained with Coomassie blue.

A chromatography purification process was developed to purify recombinant HA which results in a highly purified recombinant HA antigen that is non-denatured and suitable as a component of an influenza vaccine for human use. The following procedure was used to purify the A/Beijing/353/89 HA from S. frugiperda cells infected with the recombinant virus A8611.

The chromatography gel matrices used to purify HA from 0.5 L of infected S. frugiperda cells were 30 mL Pharmacia DEAE Sepharose Fast Flow (in a Pharmacia C16/20 column) and a 4 mL Pharmacia Lentil Lectin Sepharose 4B (in a Pharmacia C10/10 column). The outlet of the DEAE column is connected to the inlet of the lentil lectin column, and the S/N 2 cell extract prepared as described above was applied to the coupled columns at a flow rate of 1 mL/minute. The columns were washed with 30 mM Tris-HCl, pH 8.4, 25 mM LiCl, 0.5% Tween-20 until the UV absorption at 280 nm of the lentil lectin effluent returns to baseline. Under these conditions most of the contaminating proteins bind to DEAE but recombinant HA flows through the column. The remaining contaminants pass through the lectin column and glycosylated rHA binds to the lentil lectin affinity matrix. The DEAE column is disconnected, and the lectin column is washed with another 40 mL of 30 mM Tris-HCl, pH 8.4, 25 mM LiCl, 0.5% Tween-20. Next, the lectin column is washed with 40 mL of 30 mM Tris-HCl, pH 8.4, 25 mM LiCl, 0.4% (v/v) sodium deoxycholate (DOC). This step replaces the Tween-20 detergent with a detergent, like DOC, that can be removed from the protein by dialysis. Recombinant HA is then eluted from the lectin column with approximately 20 mL of 40 mL of 30 mM Tris-HCl, pH 8.4, 25 mM LiCl, 0.4% (v/v) sodium deoxycholate containing 0.3M a-D-methyl mannoside. Results are analyzed by 11% PAGE.

Due to the genetic variability of influenza HA proteins, the details of the above purification process may vary with each unique recombinant HA protein. For example, the rHA may bind to the DEAE ion exchange column instead of flowing through. Should this occur, the rHA would be removed from the DEAE column with by washing the column with buffer containing higher concentration of LiCl, NaCl, or other salts.

To remove the DOC detergent and other buffer components, the eluate from the lectin column containing the purified rHA was dialyzed against phosphate buffered saline, pH 7.5 (PBS). The purified recombinant HA was at least 95% pure as determined by analysis on SDS polyacrylamide gels.

EXAMPLE 6

Analysis of rHA Protease Resistance

Mature HA assembles into trimeric structures which are resistant to a variety of proteases, including trypsin, that degrade HA monomers (Murphy and Webster, 1990). Resistance to trypsin treatment can therefore be used as an assay for functional trimer formation. The following procedure was used to study resistance of rHA to protease treatment.

Two aliquots of purified rHA (A/Beijing/353/89) at 60 $\mu$g/mL were incubated on ice for 30 minutes in 30 mM Tris-HCl, pH 8.4, 150 mM NaCl, in the presence and absence of 50 $\mu$g/mL TPCK-treated trypsin. The reaction was stopped by the addition of 57.4 mM phenyl methyl sulfonyl fluoride in isopropanol to a final concentration of 1 mM. Aliquots of each sample were denatured by boiling in 3% SDS under reducing conditions, electrophoresed on 11.5% polyacrylamide gels, and transferred to nitrocellulose filter using standard Western blotting procedures. The HA polypeptides were detected using guinea pig anti-HA serum prepared against purified rHA and a goat anti-guinea pig IgG alkaline phosphatase conjugate.

Untreated rHA migrates at the size of the HA precursor (HA0). Protease treatment results in two major bands that migrate at the sizes predicted for influenza hemagglutinin HA1 and HA2. The results show that trypsin cleaves the rHA protein once to produce two polypeptides that are the sizes predicted for HA1 and HA2. No further proteolytic processing occurs. These results demonstrate that rHA purified by the above process is resistant to degradation by protease. This property is consistent with purified rHA being in the form of trimers.

EXAMPLE 7

Immunogenicity of rHA Using Standardized Mouse Potency Assay

One approach to measure immunogenicity of an antigen is to determine the quantity necessary to induce a detectable antibody response in mice (mouse potency assay). A standardized mouse potency assay is used to measure the immunogenicity of rHA0 vaccine. Groups of 5–10 mice are immunized once with vaccine containing serial dilutions of rHA, i.e., 0.500 $\mu$g, 0.1 $\mu$g, 0.02 $\mu$g, and 0.004 $\mu$g purified rHA. Sera are collected 28 days post immunization and antibodies against the rHA antigen measured in a standard enzyme-linked immunological solid-phase assay (ELISA) in 96 well microtiter plates. A mouse has seroconverted if the OD450 at a 1:100 dilution of the 28 day antisera is greater than three standard deviations above the mean of the OD450 of mouse pre-immune sera. The effective dosage of vaccine needed to seroconvert 50% of the mice (ED50) is a measure of the immunogenicity of the antigen.

For example, four groups of 10 mice are immunized once with either 0.1 $\mu$g, 0.02 $\mu$g, 0.004 $\mu$g, or 0.0008 $\mu$g (5-fold dilutions) of rHA0 vaccine. Sera are collected 28 days post immunization and measured against each rHA0 antigen in the vaccine for seroconversion in an ELISA assay. The dosage needed to seroconvert 50% of the mice ($ED_{50}$) is calculated and a minimum $ED_{50}$ established for each rHA0 antigen.

Preliminary data shows that a single dose of 0.004 $\mu$g of rHA0 will seroconvert at least 50% of the mice.

EXAMPLE 8

Administration of rHA in Combination with an Adjuvant and Comparison with Available Influenza Vaccines The mouse potency of purified rHA from influenza A/Beijing/353/89 was tested with alum or without alum (neat) and compared to a commercial influenza vaccine, FLUZONE® (Connaught Laboratories, Inc. Swiftwater, Pa.) which contains the A/Beijing/353/89 strain of influenza. Vaccine was administered in a dosage of 0.5 $\mu$g, 0.1 $\mu$g, 0.02 $\mu$g, and 0.04 $\mu$g. The mice were boosted at day 28 with the doses of purified rHA described above. On day 42 sera were collected and titered in an ELISA assay for IgG anti-HA antibodies.

Figure 3:
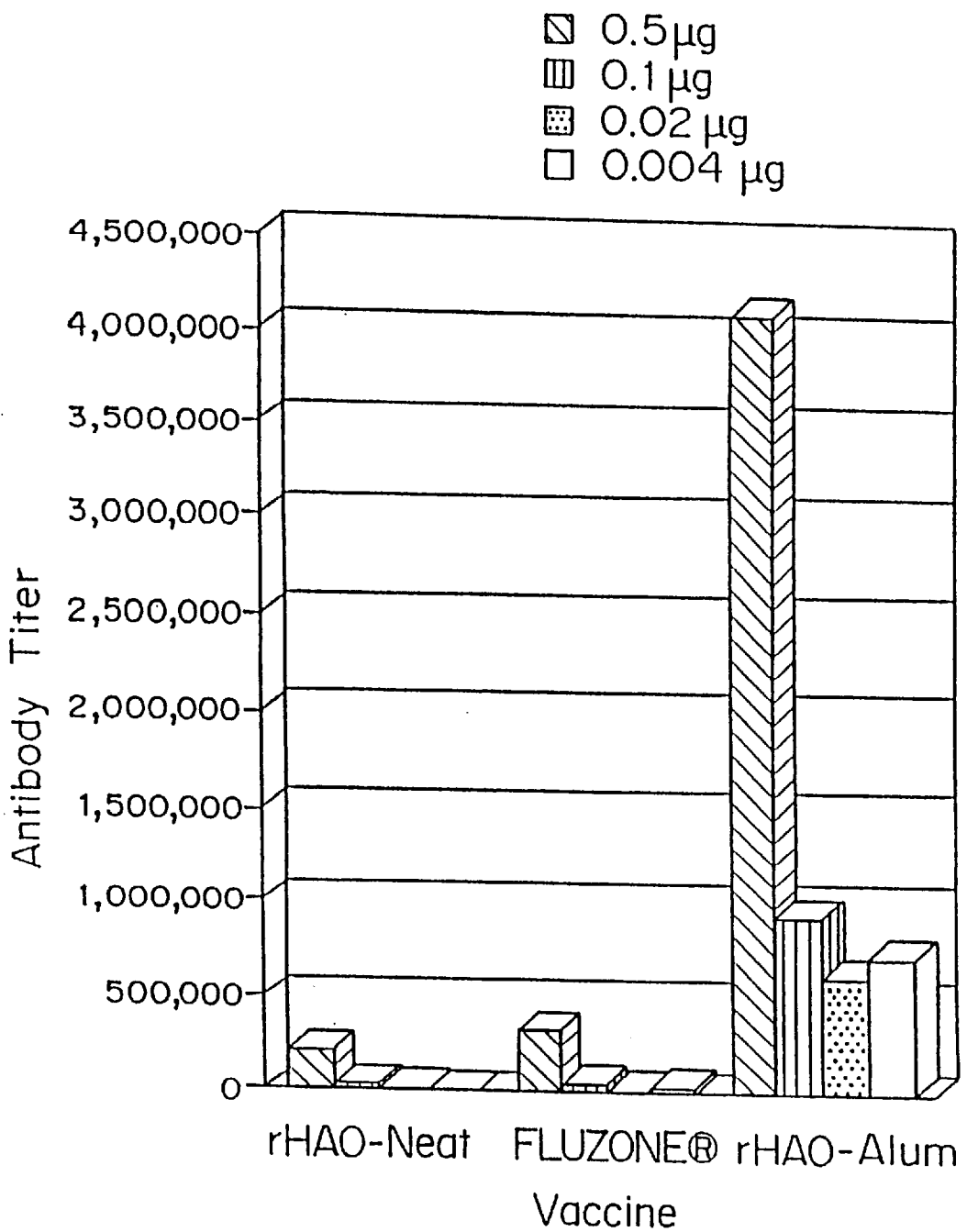
FIG. 3 is a graph of the anti-HA immune response in mice, day 42, n=5, graphing antibody titer for rHA0-neat; Fluzone® vaccine, and rHA0-alum, at dosages of 0.5 µg (dark bars), 0.1 µg (shaded bars), 0.02 µg (dotted bars), and 0.004 µg (open bars).
Figure 4A:
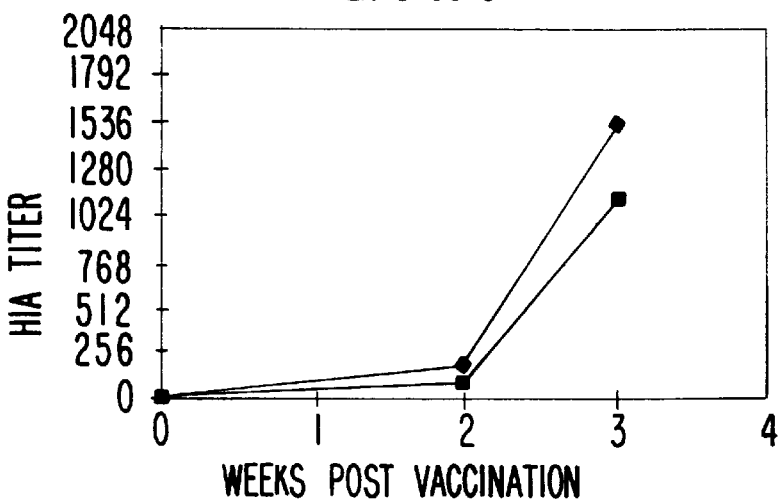
FIGS. 4a, 4b, and 4c are graphs of the anti-HA immune response in mice immunized with rHA or licensed trivalent vaccine, 1994–1995 formula, weeks post vaccination versus HIA titer, for HAI A/Texas/36/91 (FIG. 4a), HAI A/Shangdong/9/93 (FIG. 4b), and HAI B/Panama/45/90 (FIG. 4c), rHA (diamonds) and FLUVIRON® attenuated vaccine cultured in eggs (squares).
Figure 4B:
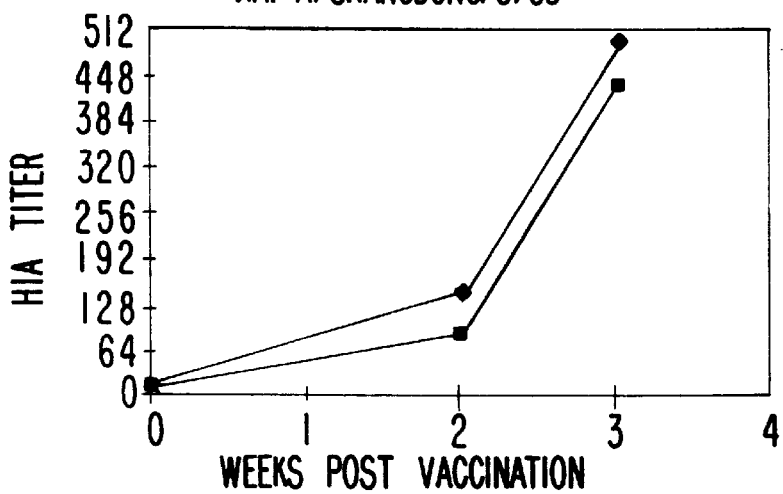
Figure 4C:
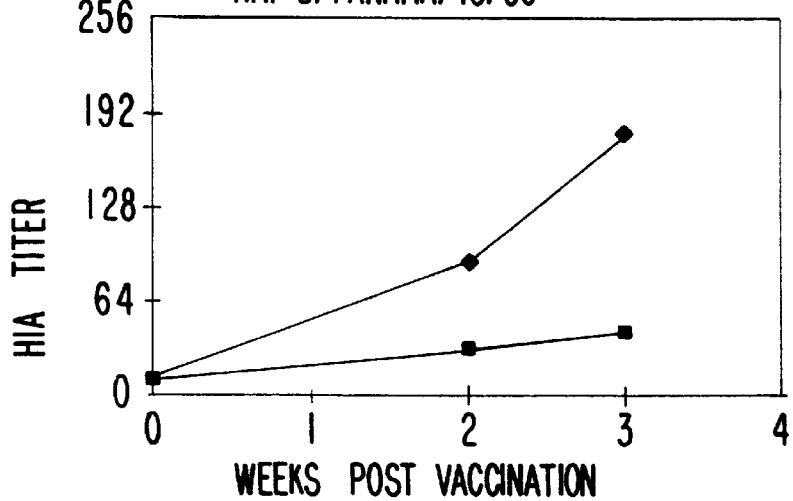

The results are shown in FIG. 3. In the absence of adjuvant, only a dosage of 0.5 $\mu$g induced production of significant antibody titer (200,000). In the presence of adjuvant, dosages of as little as 0.004 $\mu$g of rHA0 produced significant antibody. The animals immunized with rHA (neat) produced approximately the same levels of anti-HA antibodies as the commercial vaccine. Alum increased the immunogenicity of rHA, and anti-HA titers were generated that were 10-fold or higher than without adjuvant.

In summary, comparison of the immunogenicity of purified rHA0s with an influenza whole virion vaccine, (FLUZONE®, Connaught Laboratories, Inc., Swiftwater, Pa.), demonstrates that rHA0 elicits a similar immune response in mice over a period of 42 days. Adsorption of the rHA0 to alum significantly increases the immunogenicity of the purified rHA0 in mice, as measured by the assay described in Example 7. The combination with alum elicits IgG hemagglutinin antibodies that are higher than the Fluzone® influenza vaccines.

EXAMPLE 9

Hemagglutination Inhibition Studies

Hemagglutination inhibition (HAI) antibodies bind to three of four known epitopes on hemagglutinin and block the ability of influenza to agglutinate red blood cells (Wilson et al, "Structure of the hemagglutinin membrane glycoprotein of influenza virus at 3A° resolution". *Nature,*

289:366–378 (1981)). These antigenic determinants are clustered around the sialic acid receptor binding site on hemagglutinin trimers. Antibodies against these sites will neutralize virus infectivity (Weis, et al., "Structure of the influenza virus hemagglutinin complexed with its receptor, sialic acid", *Nature* 333:426–431 (1988)). The titer and specificity of HAI antibodies are an important measure of the potential for an influenza vaccine to protect against infection with like and related strains of influenza.

Studies were conducted in mice comparing the ability of purified rHA0 from A/Beijing/353/89 and FLUZONE® (Connaught Laboratories, Inc., Swiftwater, Pa.) to elicit HAI antibodies. Groups of 5 mice were injected on days 0 and 28 with 0.5 μg, 0.1 μg, 0.02 μg, or 0.004 μg of rHA0 or three times these quantities of FLUZONE® hemagglutinin so that equal levels of recombinant or viral A/Beijing/353/89 hemagglutinin were administered. For example, mice in the highest dose group were immunized with 1.5 μg of FLUZONE® hemagglutinin (0.5 μg of hemagglutinin from each strain) and 0.5 μg rHA0. The presence of additional hemagglutinin antigen in FLUZONE® from two other influenza strains may result in some cross-reactive antibodies.

Anti-hemagglutinin antibodies (hemagglutinin IgG) were measured in a standard dilutional ELISA against purified rHA0. HAI antibodies were measured against 4 hemagglutinin units of the following antigens: whole influenza A/Beijing/353/89 virus (A/Bei), purified rHA0 A/Beijing/353/89 antigen, and FLUZONE®. The HAI titer is the reciprocal of the highest dilution of antisera which inhibits the agglutination of chicken red blood cells by 50%.

Table 3 summarizes serum hemagglutinin IgG and HAI titers in the mice at day 42. High levels of anti-hemagglutinin antibodies were produced with the recombinant rHA0 vaccine. These were about ten fold higher titers than FLUZONE®. Most significant is that the rHA0 vaccine produced good titers of antibodies that block agglutination of red blood cells by the A/Beijing/353/89 virus and rHA0 antigens. Thus, the rHA0 vaccine produced HAI antibodies that recognized equally well the immunogen and the influenza A/Beijing virus. The lower HAI titers against FLUZONE® may be due to the inability of the antisera to block agglutination by the other two strains of hemagglutinin in the FLUZONE® vaccine. In contrast, FLUZONE® immunized mice produce high HAI antibodies when measured only against itself. The HAI titers against influenza A/Beijing/353/89 virus and the rHA0 antigen were considerably reduced. Similar patterns were observed in the mice in the lower dose groups.

These data also suggest that there are genetic differences between the influenza A/Beijing/353/89 strain in FLUZONE® and this same strain of influenza obtained from the FDA and passaged once in eggs prior to using the HAI assay. The fact that antibodies produced in response to the recombinant HA0 cloned from influenza A/Beijing/353/89 blocks agglutination of red blood cells by this strain of influenza as well as itself is good evidence that there were no genetic changes during the cloning process that effected the sialic acid receptor binding site on the purified rHA0 antigen.

EXAMPLE 10

Formulation and Clinical Efficacy of a 1993/1994 Influenza Vaccine

A series of human clinical trials was conducted to characterize the safety and immunogenicity in humans of an experimental influenza vaccine containing recombinant HA and to obtain preliminary data regarding the protective efficacy of such a vaccine against natural infection during an epidemic season. The results demonstrate that vaccines containing the recombinant influenza hemagglutinin (rHA0), produced in accordance with the methods described herein surprisingly caused fewer local adverse reactions and provided an equivalent or superior protective immune response when compared to a commercially available, licensed attenuated flu vaccine produced in eggs.

Materials and Methods

Vaccines.

The recombinant HA vaccines used in this study contained full length uncleaved HA (HA0) glycoprotein from the influenza A/Beijing/32/92 (H3N2) virus. Recombinant HA0 (rHA0) was produced in cultures of Lepidopteran (insect) cells following exposure to a baculovirus vector containing CDNA inserts encoding the HA gene. The expressed protein was purified under non-denaturing conditions to >95%, as measured by quantitative scanning densitometry of the bulk antigen electrophoresed on sodium dodecyl sulfate-polyacrylamide gels. The identity of the peptide was confirmed by amino acid analysis, N-terminal sequencing and Western blot analysis with anti-influenza A/Beijing/32/92 sera. The rHA0 vaccines contained a specified amount of the synthetic HA antigen either dissolved in a phosphate-buffered saline solution or adsorbed to aluminum phosphate (alum) adjuvant in the form of a gel suspension. The licensed trivalent subvirion vaccine used in this study contained 15 μg/dose of each the HAs from influenza A/Texas/36/91 (N1N1), A/Beijing/32/92 (H3N2) and B/Panama,45/90 viruses (FLUZONE™ attenuated flu vaccine produced in eggs, Connaught Laboratories, Swiftwater, Pa.).

TABLE 3

HAI Titers against rHA0 and FLUZONE ®

| | rHA0 A/Bei (day 42) | | | | FLUZONE ® (day 42) | | | |
|---|---|---|---|---|---|---|---|---|
| | HA IgG | HAI | | | HA IgG | HAI | | |
| Mouse # | rHA0 | A/Bei | rHA0 | FLUZONE | rHA0 | A/Bei | rHA0 | FLUZONE |
| 1 | 4,096,000 | 1,920 | 960 | 15 | 256,000 | <10 | <10 | 600 |
| 2 | 4,096,000 | 480 | 480 | 15 | 512,000 | 120 | 120 | 600 |
| 3 | 8,192,000 | 1,920 | 960 | 15 | 256,000 | 60 | 60 | 300 |
| 4 | 4,096,000 | 960 | 960 | 30 | 128,000 | 30 | 30 | 400 |
| 5 | 4,096,000 | 1,920 | 960 | 60 | 512,000 | 80 | 80 | 400 |
| MEAN | 4,915,000 | 1,440 | 864 | 27 | 332,800 | 58 | 58 | 460 |

Clinical Studies.

Identical study protocols were approved by the Institutional Review Boards of Saint Louis University and the University of Rochester. Healthy adults aged 18 to 45 years were enrolled at both institutions. Subjects were randomly assigned to receive one of the following five vaccine preparations in a double-blinded manner: (1) 15 μg rHA0, (2) μg rHA0 plus alum, (3) 90 μg rHA0, (4) licensed trivalent inactivated influenza vaccine, or (5) saline placebo. Vaccines were administered by intramuscular injection in a volume of 0.5 ml. To allow for an initial assessment of the safety of the three vaccine preparations containing rHA0, the first 25 subjects to be vaccinated were randomized (i.e., 5 persons per study arm) independently of the other subjects and closely monitored by phone contact for 48 hours post-vaccination before proceeding with the remaining vaccinations. All subjects were instructed to fill out a daily report card of adverse reactions, including both local and systemic symptoms, during the first 6 days post-vaccination. Symptoms were self-graded as mild, moderate or severe in nature. Oral temperatures were taken and recorded by participants if they felt feverish. If present, localized swelling or erythema at the injection site was graded according to whether the area was less than or greater than the size of a quarter in diameter, respectively. All vaccinations were performed during the last week of November and first week of December, 1993. Serum specimens were obtained from each subject at the time of vaccination, 3 weeks post-vaccination, and once again in late March or April 1994 at least 2 to 3 weeks after influenza viruses were no longer circulating in the local communities. Volunteers at each institution were instructed to contact the study center if they experienced an influenza-like illness during the winter influenza epidemic season. An influenza-like illness was defined as the presence of any respiratory symptom(s) of two days or greater duration accompanied by fever and/or systemic symptoms of myalgias or chills. Subjects who reported influenza-like symptoms had nasal and pharyngeal swabs obtained for virus culture and identification. Clinical specimens were given coded identification numbers and processed in a blinded fashion.

Serology.

For each type of serologic assay, all specimens from both institutions were tested in one batch by a single laboratory. Hemagglutination inhibition (HAI) antibodies to influenza A/Beijing/32/93 (H3N2) virus antigen were measured in sera by a standard microtiter assay, following removal of nonspecific inhibitor with receptor destroying enzyme and of cold agglutinins by hemadsorption at 4° C. The titer was defined as the highest serum dilution that completely prevented hemagglutination by 4 antigen units of virus, using 1:4 as the starting dilution. Serum HA-specific immunoglobulin G (IgG) antibodies were measured by enzyme-linked immunosorbent assay (ELISA), using purified rHA0 from influenza A/Beijing/32/92 (H3N2) as the coating antigen. The sequence of reagents from solid phase outward consisted of (1) purified rHA0 antigen, (2) serum specimen, (3) alkaline phosphatase-conjugated goat anti-human IgG, and (4) p-nitrophenyl phosphate disodium substrate. The ELISA titer was expressed as the highest dilution at which the optical density of the antigen-containing well was at least twice that of the corresponding control well without antigen. Neutralizing antibodies were measured using the microneutralization assay previously described by Treanor, J. J., and Betts, R. F., *J. Infect. Dis.* 168:455–459 (1993). In brief, serial dilutions of heat-inactivated sera were mixed with approximately 100 TCID$_{50}$ of influenza A/Beijing/32/92 (H3N2) virus and incubated at 37° C. for 1 hr. The virus-sera mixture was then adsorbed to confluent monolayers of Madin-Darby canine kidney (MDCK) cells in 96-well plates for 1 hr at room temperature. The plates were washed to remove residual inoculum, refed serum-free Dulbecco's MEM with 2 μg/ml trypsin, and incubated in 5% $CO_2$ at 33° C. for 72 hr. Cells were then fixed with methanol, and viral replication was assessed using a panel of murine monoclonal antibodies specific for the matrix and nucleoproteins of influenza A virus (Centers for Disease Control, Atlanta, Ga.), followed by alkaline phosphatase-conjugated anti-mouse IgG. The end-point titer of the sera was defined as the highest dilution resulting in greater than 50% reduction in signal compared with nonneutralized control wells.

Virology.

Viral cultures of nasopharyngeal swab specimens were performed at each institution by standard techniques. Specimens were inoculated in either MDCK or rhesus monkey kidney cells and incubated at 33° C. for 14 days. Hemadsorption of cell monolayers was tested with 0.4% guinea pig erythrocytes. Influenza viruses were identified in hemadsorption positive cultures by HAI using H3-specific antisera (Centers for Disease Control).

Statistical Analyses.

Reciprocal HAI, ELISA IgG and neutralizing antibody titers were logarithmically transformed for statistical analysis. A significant response to vaccination was defined as a fourfold or greater rise in antibody titer between the prevaccination and 3-week post-vaccination serum specimens. Laboratory evidence of influenza A (H3N2) virus infection was defined as the isolation of virus from nasopharyngeal secretions and/or a four-fold or greater increase in serum HAI antibody titer between the 3-week post-vaccination (preseason) specimen collected in December and the corresponding postseason specimen collected the following spring. Differences between vaccine groups were analyzed using Fisher's exact test to compare the proportions of subjects with adverse reactions, significant antibody responses or laboratory-confirmed influenza illness or infection, and analysis of variance (ANOVA) to compare post-vaccination mean reciprocal $\log_2$ antibody titers. The modified Bonferroni's inequality and Tukey-Kramer tests were applied where appropriate to account for multiple possible comparisons.

Results

Reactogenicity.

The rHA0 vaccines used in this study were safe and well-tolerated. The frequency of adverse reactions did not appear to be influenced by changing the dose of rHA0 antigen from 15 μg to 90 μg, but may have been slightly increased by the addition of alum. Localized erythema, pain and tenderness at the injection site were each reported significantly more frequently by recipients of licensed subvirion vaccine than by recipients of either 15 μg or 90 μg rHA0 in saline. With the exception of one individual who experienced moderately severe pain, tenderness and stiffness in the arm following immunization with licensed vaccine, all symptoms were graded as mild in nature and were generally 1–2 days in duration. Localized erythema and/or induration, when present, was invariably less than the area of a quarter in size.

Immunogenicity.

Baseline titers of serum HAI antibody to influenza A/Beijing/32/92 (H3N2) virus were less than or equal to 1:8 in 64 (50%) of the 127 subjects enrolled. Most subjects in each of the four vaccine groups had HA-specific serologic responses measured by HAI and ELISA (Table 4). Post-vaccination titers of serum HAI antibody were greater than or equal to 1:32 in all vaccine recipients with the exceptions of two persons given 15 μg rHA0 and one given the licensed vaccine. Vaccination was likewise associated with the production of neutralizing antibody in the majority of volunteers. Mean rises in antibody titers and seroconversion rates tended to be slightly lower following immunization with 15 μg rHA0 than with licensed vaccine, although these differences were not statistically significant. Antibody response to rHA0 were not enhanced by the addition of alum. Subjects immunized with 90 μg rHA0 achieved post-vaccination mean HAI and ELISA IgG antibody titers that were two- to five-fold higher than in any of the other three vaccine groups (differences were statistically significant when comparing serum HAI titers).

Protective Efficacy.

During the period of surveillance, there were a total of 28 influenza-like illnesses reported by 26 subjects. Four of these individuals (three of whom had received placebo and one of whom had been immunized with 15 μg rHA0) had influenza A (H3N2) virus isolated from nasopharyngeal cultures. Significant increases in HAI antibody titer to influenza A/Beijing/32/92 (H3N2) between preseason and postseason serum specimens were also present in three of the four culture-confirmed cases, but not in any other individuals who reported illness. The lone rHA0 recipient who subsequently developed laboratory-confirmed influenza illness had the positive culture obtained 31 days after immunization, and had seroconverted from a prevaccination HAI titer of less than 1:4 to a post-vaccination (preseason) titer of 1:32. Two additional placebo recipients and one volunteer immunized with licensed vaccine had serologic evidence of infection with influenza A (H3N2) virus during the epidemic season in the absence of clinical illness. Compared to all vaccinated subjects (or to all subjects who received any rHA0 vaccine) as one group, a significantly larger proportion of placebo recipients had laboratory-confirmed influenza A (H3N2) illness ($p<0.05$) or infection ($p<0.005$).

The above findings indicate that influenza vaccines containing purified rHA0 antigen, prepared as described in the above-identified patent application, are well-tolerated and capable of eliciting protective immune responses in human subjects. Even at a dose of 90 μg, the rHA0 evaluated in this study was no more reactogenic than saline placebo, and caused significantly fewer local adverse reactions than did a licensed trivalent subvirion vaccine containing half as much (i.e., 45 μg) total HA antigen.

Neutralizing, HA-specific antibody responses to the 15 μg rHA0 preparation were comparable to those elicited by subvirion vaccine, and were significantly improved by raising the dose of rHA0 to 90 μg.

Overall rates of infection and illness resulting from natural exposure to the circulating epidemic strain of influenza A (H3N2) virus were significantly lower among vaccinated subjects than among placebo recipients. The data suggest that protective immunity conferred by rHA0, particularly when administered at high doses, is comparable or superior to that induced by currently available vaccines.

TABLE 4

Serum antibody responses in young adult subjects following immunization with vaccines containing purified recombinant hemagglutinin (rHAO) from influenza A/Beijing 32/92 (H3N2), licensed trivalent trivalent subviron containing 15 μg HA from A/Beijing/32/92 (H3N2), or saline placebo.

| Vaccine | HAI antibody | | | | ELISA IgG HA antibody | | | Neutralizing antibody Microneutralization | | |
|---|---|---|---|---|---|---|---|---|---|---|
| (Number | HAI titer | | % with ≧ | % with | ELISA titer | | % with ≧ | titer | | % with ≧ |
| in group | Pre | Post | 4 × rise | post ≧ 1:32 | Pre | Post | 4 × rise | Pre | Post | 4 × rise |
| rHAO 15 μg (26) | 3.7 ± 0.3 | 9.0 ± 0.6* | 85 | 92 | 8.7 ± 0.3 | 12.0 ± 0.3 | 88 | 5.7 ± 0.3 | 10.0 ± 0.4 | 85 |
| rHAO 15 μg plus alum (26) | 4.3 ± 0.5 | 8.6 ± 0.4* | 88 | 100 | 9.4 ± 0.4 | 11.5 ± 0.4 | 76 | 6.4 ± 0.4 | 9.3 ± 0.2 | 76 |
| rHAO 90 μg (26) | 3.3 ± 0.4 | 11.1 ± 0.3 | 100 | 100 | 8.5 ± 0.4 | 13.1 ± 0.4 | 100 | 5.7 ± 0.3 | 10.2 ± 0.4 | 96 |
| Licensed subviron (26) | 3.7 ± 0.4 | 9.3 ± 0.5+ | 100 | 96 | 8.1 ± 0.4 | 12.0 ± 0.4 | 92 | 5.8 ± 0.3 | 9.9 ± 0.4 | 96 |
| Placebo (24) | 3.7 ± 0.5 | 3.8 ± 0.5# | 0 | 38 | 9.1 ± 0.3 | 9.1 ± 0.3 | 0 | 5.3 ± 0.4 | 5.4 ± 0.4 | 8 |

HAI, hemagglutination inhibition;
HA, hemagglutinin;
ELISA, enzyme-linked immunosorbent assay.
Postvaccination serum specimens were obtained three weeks after immunization.
Antibody titers are expressed as means reciprocal $\log_2$ ± SEM.
Statistical comparisons are made between the mean postvaccination HAI titer of the designated group and that of the 90 μg rHAO vaccine group by analysis of variance with Dunnett's test for multiple comparisons.
*, $P < 0.01$;
+, $P < 0.05$;
, $P < 0.01$

EXAMPLE 11

Method for Making an Improved HAO Cloning Vector

An improved cloning vector for expression of mature HA wherein the gene encoding the HA was located immediately downstream of the sequence encoding the chitinase signal peptide was designed.

Linear pMGS27 with Single-stranded Tails was Created

In the pMGS12 plasmid, HA was cloned into Sma1 or Kpn1 sites immediately downstream from the chitinase signal peptide. The nucleotide and corresponding amino acid sequences shown are set forth respectively in SEQ ID NO. 22 and SEQ ID NO. 23.

```
         chitinase signal peptide                    Sma1      Kpn1
5'-TGG  TTG  GTC  GCC  GTT  TCT  AAC  GCG  ATT  CCC  GGG  GGT  ACC
   TRP  LEU  VAL  ALA  VAL  SER  ASN  ALA  ILE  PRO  GLY  GLY  THR
```

This region was changed by oligo directed mutagenesis to create pMGS27 The nucleotide sequence shown is set forth in SEQ ID NO. 24, (changed bases were underlined):

```
5'-TGG  TTA  GTC  GCC  GTG  TCCTGCAGGCCAGAGAGGCCTT  GGT  ACC
                                  Pst1
```

Plasmid pMGS27 was linearized with Pst1 cut (the nucleotide sequence shown in the top row is set forth at positions 6 through 36 of SEQ ID NO. 24, the nucleotide sequence shown in the bottom row is the complement sequence):

```
 A GTC GCC GTG TCC TGCA 5'      GGCCAGAGAGGCC T
 T CAG CGG CAC AGG 5'         ACGTCCGGTCTCTCCGG A
``` then treating the linear pMGS27 with T4 DNA polymerase plus dATP to create single stranded tails as shown below (the nucleotide sequence preceeded with the 5' symbol shown in the top row is set forth at positions 23 through 36 of SEQ ID NO. 24, the nucleotide sequence preceeding the 5' symbol shown in the bottom row is set forth at positions 6 through 18 of the complement sequence of SEQ ID NO. 24):

```
 A                      5' GGCCAGAGAGGCC T
 T CAG CGG CAC AGG 5'                    A
```

Target HA Gene Was Cloned Into pMGS27

Step 1. PCR primers were synthesized.

Forward oligo (SEQ ID NO. 25):

5' GTC GCC GTG TCC AAC GCG (5' end 20 bases of the mature HA)

Reverse oligo (complement sequence of SEQ ID NO. 26):

(3' end 20 bases of the mature HA) ATT AA CCGGTCTCTCCGG 5'

PCR of the HA Gene

PCR of the target HA gene with the two oligos was used to obtain (SEQ ID NO. 25—mature HA—SEQ ID NO. 26 and complement sequence are shown):

```
5' GTC  GCC  GTG  TCC  ACC  GCG  (mature HA) TAA  TT
   GGCCAGAGAGGCC
      CAG  CGG  CAC  AGG  TTG  CGC  (mature HA) ATT  AA
   CCGGTCTCTCCGG
```

Anneal Target HA Gene Into pMGS27 and Transform *E. coli*

Linear pMGS27 and the T4 DNA polymerase treated PCR fragment of the HA gene were mixed. The two molecules anneal to each other, to form a circular plasmid which is ready to be used for transforming *E. coli*. The diagram includes SEQ ID NOS. 25 and 26, residues 23 through 36 of SEQ ID NO. 24 and complement residues 6 through 18 of SEQ ID NO. 24.

```
GTC  GCC  GTG  TCC  AAC  GCG  (mature HA) TAA  TT
                              TTG  CGC  (mature HA) ATT  AA
CCGGTCTCTCCGG
```

+

```
 A                              GGCCAGAGAGGCC T
 T CAG CGG CAC AGG                            A
``` to

GTC  GCC  GTG  TCC  AAC  GCG  (mature HA) TAA
TTGGCCAGAGAGGCCT
chitinase signal peptide                            stop As shown above, there is no extra amino acid in between the signal peptide and the mature HA.

EXAMPLE 12

Preparation and Efficacy of a Trivalent Types A and B 1995–1996 Influenza Virus Vaccine Influenza virus vaccine, purified recombinant hemagglutinin, trivalent, types A and B (A/Texas/36/92\1 (H1N1), A/Johanesburg/33/94 (H3N2), and B/Harbin/7/94) is a non-infectious subunit derived from purified, recombinant influenza hemagglutinin antigens (HA). The HA genes were cloned from the Center for Disease Control/Food and Drug Administration recommended strains of influenza A and B viruses as described above and the identity of each cloned gene determined by DNA sequence analysis. Baculovirus expression vectors containing the cloned HA genes from influenza virus strains A/Texas/36/91 (H1N1), A/Johanesburg/33/94 (H3N2), B/Harbin/7/94 were used to produce the recombinant HA antigens in cultured insect cells. The recombinant HA proteins are full length, uncleaved hemagglutinins (rHAO) with a molecular weight of approximately 69,000. The rHAO were produced in a *Spodoptera frugiperda* (Lepidopteran) cell line maintained in a serum-free culture medium. The trivalent vaccines is composed of purified (greater than 95% pure, more probably greater than 99% pure) rHAO from the two influenza A strains and one B strain mixed in equal proportions. The vaccine is supplied for clinical use as purified types A and B rHAO proteins in phosphate buffered saline solution without added preservative.

Animal studies with monovalent, bivalent and trivalent rHAO vaccines have demonstrated that they are free of significant toxicity. There are no detectable toxic or adventitious agents in the vaccine. General safety and immunogenicity studies of A/Beijing/32/92 and A/Texas/36/91 rHAO were conducted in mice and guinea pigs. No adverse reactions were noted. In mice, a single immunization with 15 micrograms of rHAO antigens without adjuvant induces in two to three weeks high levels of anti-HA IgG antibodies, hemagglutinin inhibition (HAI) antibodies and neutralizing antibodies.

In one study, groups of ten mice were immunized with 15 micrograms of purified rHAO A/Beijing/32/92 (H3N2) made in cells adapted to media containing 10% fetal bovine serum or rHAO made in insect cells adapted to media containing 10% fetal bovine serum or rHAO made in insect cells adapted to a serum-free medium (rHAO-SF). Two and three weeks post injection the mice were bled and serum samples prepared. Each sera were measured for anti-HA IgG and HAI antibodies. Both rHAO and rHAO-SF antigens elicit similar titers of anti-HA and HAI antibodies. Both rHAO and rHAO-SF antigens elicit similar titers of anti-HA and HAI antibodies. Two weeks following the single immunization, most of the mice have significant titers of HAI antibodies and by week three 8/10 mice in each group had HAI titers of 32 or greater. These and other biochemical and immunological studies demonstrate that rHAO produced in serum-free insect cell culture is indistinguishable from rHAO manufactured under serum-containing fermentation conditions.

A study was conducted to compare the 1994–1995 formulation of the trivalent rHAO influenza vaccine with a licensed purified virus surface antigen vaccine, Fluvirin® (an attenuated influenza viral vaccine produced by culturing in eggs). Each vaccine contained 15 micrograms rHAO or viral HA per 0.5 ml from A/Texas/36/91 (H1N1), A/Shangdong/9/93 (H3N2), and B/Panama/45/90 influenza strains. Both the recombinant rHAO and Fluvirin® vaccines are in phosphate buffered saline. At zero, two and three weeks post injection, groups of ten mice were bled and serum prepared. The serum samples were measured for anti-HA IgG antibodies inhibiting antibodies against egg-grown influenza virus, and for neutralizing antibodies against egg-grown influenza viruses from each virus strain.

As demonstrated by FIGS. 4*a*, 4*b* and 4*c*, both the recombinant rHAO and licensed influenza vaccines induce high levels of serum IgG antibodies against hemagglutinins from each of the three influenza strains in the vaccines. Four to nearly ten fold higher IgG antibody titers were induced by the rHAO vaccine as compared to the licensed vaccine. Antibodies were also produced which inhibited hemagglutinin of chick red blood cells with both influenza A and the B strain viruses, as shown in Table 5. HAI titers were equivalent or higher against each of the three influenza virus strains in mice receiving the trivalent rHAO vaccine as compared to the licensed vaccine. The vaccines also induced high levels of neutralizing antibodies against the specific influenza A and B virus strains as measured in a standard microtiter virus neutralization assay. The geometric neutralizing antibody titers were approximately two fold higher in mice immunized with rHAO than with the licensed purified virus surface antigen vaccine, Fluvirin®. These results demonstrate that a trivalent formulation of rHAO vaccine based on the 1994–1995 type A and B influenza strains is equivalent or superior to a licensed subunit influenza vaccine at inducing functional HAI and neutralizing serum antibodies against all three strains of influenza in the vaccine.

TABLE 5

Comparison of trivalent rHAO vaccine with Fluvirin ®.

| Virus strain used as antigen | Trivalent rHAO Influenza vaccine GMT (n = 10 mice) week 0 | week 3 | Fluvirin ® GMT (n = 10 mice) week 0 | week 3 |
|---|---|---|---|---|
| | anti-HA IgG | | anti-HA IgG | |
| A/Texas/36/91 (H1N1) | <1000 | 103,000 | <1000 | 11,200 |
| A/Shangdong/32/92 (H3N2) | <1000 | 162,400 | <1000 | 41,000 |
| B/Panama/45/90 | <1000 | 164,800 | <1000 | 26,000 |
| | HAI | | HAI | |
| A/Texas/36/91 (H1N1) | <8 | 1,522 | <8 | 1,088 |
| A/Shangdong/32/92 (H3N2) | <8 | 494 | <8 | 435 |
| B/Panama/45/90 | <8 | 174 | <8 | 42 |
| | Neutralizing Ab | | Neutralizing Ab | |
| A/Texas/36/91 (H1N1) | <100 | 5,800 | <100 | 2,720 |
| A/Shangdong/32/92 (H3N2) | <100 | 840 | <100 | 360 |
| B/Panama/45/90 | <100 | 1,300 | <100 | 700 |

Modifications and variations of the methods and compositions described herein for use in preparing and using a recombinant influenza vaccine will be obvious to those skilled in the art.

We claim:

1. Substantially pure, recombinant, mature, glycosylated influenza hemagglutinin protein produced by a baculovirus expression system in cultured insect cells, wherein said hemagglutinin protein is purified to 95% or greater and said protein is immunogenic, and induces a protective immune response when used as a vaccine; and, said hemagglutinin protein further comprising a second protein which is fused to the hemagglutinin.

2. The mature, glycosylated hemagglutinin protein of claim 1, wherein the second protein is selected from the group consisting of a hepatitis B viral protein, a HIV protein, a carcinoembryonic antigen, and a neuraminidase.

3. The mature, glycosylated hemagglutinin protein of claim 1 further comprising a baculovirus signal peptide coupled directly to the hemagglutinin protein without intervening amino acids.

4. A vaccine comprising the mature, glycosylated hemagglutinin protein of claim 3 and a pharmaceutically acceptable carrier.

5. The vaccine of claim 4 further comprising an adjuvant.

6. The vaccine of claim 4, wherein the pharmaceutically acceptable carrier is a polymeric delivery system.

7. The mature, glycosylated hemagglutinin protein of claim 1, wherein the mature, glycosylated hemagglutinin protein is from an influenza virus selected from the group consisting of an influenza A strain and an influenza B strain.

8. The mature, glycosylated hemagglutinin protein of claim 7, wherein the virus infects humans.

9. A vaccine comprising the mature, glycosylated hemagglutinin protein of claim 1 and a pharmaceutically acceptable carrier.

10. the vaccine of claim 9, wherein in the mature, glycosylated hemagglutinin protein, wherein the second protein is neuraminidase.

11. The vaccine of claim 1 further comprising an adjuvant.

12. The mature, glycosylated hemagglutinin protein of claim 1, wherein the second protein is neuraminidase.

13. A method for vaccinating an animal against influenza comprising administering to the animal an effective amount of the mature, glycosylated hemagglutinin protein as claimed in claim 3 or claim 1.

14. The method of claim 13 further comprising administering the mature, glycosylated hemagglutinin protein in a polymeric delivery system.

15. The method of claim 13, wherein the mature, glycosylated hemagglutinin protein is from an influenza virus selected from the group consisting of an influenza strain and an influenza B strain.

16. The method of claim 13, wherein the animal is selected from the group consisting of a mammal and an avian species.

17. The method of claim 13, wherein the animal is a human.

18. A method for making the mature, glycosylated hemagglutinin protein of claim 1, said method comprising infecting cultured insect cells with a vector containing the following sequences in 5'→3' order: a polyhedron promoter from a baculovirus, an ATG translational start codon, a baculovirus signal peptide, the coding sequence for hemagglutinin from a strain of influenza selected from the group consisting of an influenza A strain and an influenza B strains, coding sequence for the second protein, a translational termination codon, and a polyhedron RNA polyadenylation signal, and culturing the cells in a nutrient media.

19. A recombinant influenza hemagglutinin protein expressed in a baculovirus expression system cultured in insect cells prepared by the method of claim 18 and purified to 95% or greater.

20. A method for vaccinating an animal against influenza comprising administering to the animal an effective amount of a recombinant influenza hemagglutinin protein expressed in a baculovirus expression system in cultured insect cells wherein the influenza hemaggluttinin protein is prepared by the method of claim 18.

21. The method of claim 18, wherein the mature, glycosylated hemagglutinin protein is isolated by separating membrane-bound proteins including the mature, glycosylated hemagglutinin protein from non-membrane proteins at alkaline pH, washing the membrane bound proteins to elute the mature, glycosylated hemagglutinin protein, separating the eluted mature, glycosylated hemagglutinin protein by an anion exchange resin with a change in pH, and separating the anion exchange passaged mature, glycosylated hemagglutinin protein by a cation exchange resin with a change in salt concentration.

22. The method of claim 13, wherein in the mature, glycosylated hemagglutinin protein, wherein the second protein is neuraminidase.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO (iv) ANTI-SENSE: NO (vi) ORIGINAL SOURCE:
                (A) ORGANISM: Influenza virus (x) PUBLICATION INFORMATION:
                (A) AUTHORS: Davis, et al.
                (B) TITLE:Construction and Characterization of a
                        Bacterial Clone Containing the Hemagglutinin Gene
                        of the WSN Strain (HON1) of Influenza Virus
                (C) JOURNAL: Gene
                (D) VOLUME: 10
                (F) PAGES: 205-218
                (G) DATE: 1980

(xi) SEQUENCE DESCRIPTION: SEQ ID NO:1:

AGCAAAAGCA GG                                                                                                                   12

(2) INFORMATION FOR SEQ ID NO:2:

(i) SEQUENCE CHARACTERISTICS:
                (A) LENGTH: 39 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:2:

GGGGGTACCC CCGGGAGCAA AAGCAGGGGA AAATAAAAA                                                                                       39

(2) INFORMATION FOR SEQ ID NO:3:

(i) SEQUENCE CHARACTERISTICS:
                (A) LENGTH: 35 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:3:

CCCGGTACCT CAKATKCATA TTCTGCACTG CAAAG                                                                                           35

(2) INFORMATION FOR SEQ ID NO:4:

(i) SEQUENCE CHARACTERISTICS:
                (A) LENGTH: 39 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:4:

GGGGGTACCC CCGGGGACAC AATATGTATA GGCTACCAT                                                                                       39

(2) INFORMATION FOR SEQ ID NO:5:

(i) SEQUENCE CHARACTERISTICS:
                (A) LENGTH: 39 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:5:

GGGGGATCCG GTACCAGCAA AAGCAGGGGA TAATTCTAT                                                                                       39

( 2 ) INFORMATION FOR SEQ ID NO:6:

( i ) SEQUENCE CHARACTERISTICS:
        ( A ) LENGTH: 1793 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Influenza virus
        ( C ) INDIVIDUAL ISOLATE: A/Bejing/32/92 rHA ( i x ) FEATURE:
        ( A ) NAME/KEY: polyhedrin mRNA leader (partial)
        ( B ) LOCATION: 1 to 18

( i x ) FEATURE:
        ( A ) NAME/KEY: coding region for AcNPV 61K protein signal
            sequence
        ( B ) LOCATION: 19 to 72

( i x ) FEATURE:
        ( A ) NAME/KEY: SmaI restriction site
        ( B ) LOCATION: 76 to 81

( i x ) FEATURE:
        ( A ) NAME/KEY: coding region for mature rHA
        ( B ) LOCATION: 73 to 1728

( i x ) FEATURE:
        ( A ) NAME/KEY: KpnI restriction site
        ( B ) LOCATION: 1771 to 1777

( i x ) FEATURE:
        ( A ) NAME/KEY: BglII restriction site
        ( B ) LOCATION: 1776 to 1782

( i x ) FEATURE:
        ( A ) NAME/KEY: unversal translation termination signal
        ( B ) LOCATION: 1783 to 1793

( x i ) SEQUENCE DESCRIPTION: SEQ ID NO:6:

```
TAAAAAACC  TATAAATAAT  GCCCTTGTAC  AAATTGTTAA  ACGTTTTGTG  GTTGGTCGCC      60

GTTTCTAACG  CGATTCCCGG  GGACTTTCCA  GGAAATGACA  ACAGCACAGC  AACGCTGTGC     120

CTGGACATC   ATGCAGTGCC  AAACGGAACG  CTAGTGAAAA  CAATCACGAA  TGATCAAATT     180

GAAGTGACTA  ATGCTACTGA  GCTGGTTCAG  AGTTCCTCAA  CAGGTAGAAT  ATGCGACAGT     240

CCTCACCGAA  TCCTTGATGG  AAAAAACTGC  ACACTGATAG  ATGCTCTATT  GGGAGACCCT     300

CATTGTGATG  GCTTCCAAAA  TAAGGAATGG  GACCTTTTTG  TTGAACGCAG  CAAAGCTTAC     360

AGCAACTGTT  ACCCTTATGA  TGTACCGGAT  TATGCCTCCC  TTAGGTCACT  AGTTGCCTCA     420

TCAGGCACCC  TGGAGTTTAT  CAATGAAGAC  TTCAATTGGA  CTGGAGTCGC  TCAGGATGGG     480

GGAAGCTATG  CTTGCAAAAG  GGGATCTGTT  AACAGTTTCT  TAGTAGATT   GAATTGGTTG     540

CACAAATCAG  AATACAAATA  TCCAGCGCTG  AACGTGACTA  TGCCAAACAA  TGGCAAATTT     600

GACAAATTGT  ACATTTGGGG  GGTTCACCAC  CCGAGCACGG  ACAGAGACCA  AACCAGCCTA     660

TATGTTCGAG  CATCAGGGAG  AGTCACAGTC  TCTACCAAAA  GAAGCCAACA  AACTGTAACC     720

CCGAATATCG  GGTCTAGACC  CTGGGTAAGG  GGTCAGTCCA  GTAGAATAAG  CATCTATTGG     780

ACAATAGTAA  AACCGGGAGA  CATACTTTTG  ATTAATAGCA  CAGGGAATCT  AATTGCTCCT     840

CGGGGTTACT  TCAAAATACG  AAATGGGAAA  AGCTCAATAA  TGAGGTCAGA  TGCACCCATT     900
```

-continued

```
GGCACCTGCA GTTCTGAATG CATCACTCCA AATGGAAGCA TTCCCAATGA CAAACCTTTT       960
CAAAATGTAA ACAGGATCAC ATATGGGGCC TGCCCCAGAT ATGTTAAGCA AAACACTCTG      1020
AAATTGGCAA CAGGGATGCG GAATGTACCA GAGAAACAAA CTAGAGGCAT ATTCGGCGCA      1080
ATCGCAGGTT TCATAGAAAA TGGTTGGGAG GGAATGGTAG ACGGTTGGTA CGGTTTCAGG      1140
CATCAAAATT CTGAGGGCAC AGGACAAGCA GCAGATCTTA AAAGCACTCA AGCAGCAATC      1200
GACCAAATCA ACGGGAAACT GAATAGGTTA ATCGAGAAAA CGAACGAGAA ATTCCATCAA      1260
ATCGAAAAAG AATTCTCAGA AGTAGAAGGG AGAATTCAGG ACCTCGAGAA ATATGTTGAA      1320
GACACTAAAA TAGATCTCTG GTCTTACAAC GCGGAGCTTC TTGTTGCCCT GGAGAACCAA      1380
CATACAATTG ATCTAACTGA CTCAGAAATG AACAAACTGT TTGAAAAAAC AAGGAAGCAA      1440
CTGAGGGAAA ATGCTGAGGA CATGGGCAAT GGTTGCTTCA AAATATACCA CAAATGTGAC      1500
AATGCCTGCA TAGGGTCAAT CAGAAATGGA ACTTATGACC ATGATGTATA CAGAGACGAA      1560
GCATTAAACA ACCGGTTCCA GATCAAAGGT GTTGAGCTGA AGTCAGGATA CAAAGATTGG      1620
ATCCTATGGA TTTCCTTTGC CATATCATGC TTTTTGCTTT GTGTTGTTTT GCTGGGGTTC      1680
ATCATGTGGG CCTGCCAAAA AGGCAACATT AGGTGCAACA TTTGCATTTG AGTGTATTAA      1740
TTAAAAACAC CCTTGTTTCT AGGATGATTC GGTACCAGAT CTTAATTAAT TAA             1793
```

(2) INFORMATION FOR SEQ ID NO:7:

(i) SEQUENCE CHARACTERISTICS:
        (A) LENGTH: 570 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Influenza virus
        (C) INDIVIDUAL ISOLATE: A/Bejing/32/92 rHA (ix) FEATURE:
        (A) NAME/KEY: AcNPV 61K protein signal sequence
        (B) LOCATION: 1 to 18

(ix) FEATURE:
        (A) NAME/KEY: mature rHA
        (B) LOCATION: 19 to 552

(xi) SEQUENCE DESCRIPTION: SEQ ID NO:7:

```
Met Pro Leu Tyr Lys Leu Leu Asn Val Leu Trp Leu Val Ala Val Ser
 1               5                  10                  15

Asn Ala Ile Pro Gly Asp Phe Pro Gly Asn Asp Asn Ser Thr Ala Thr
             20                  25                  30

Leu Cys Leu Gly His His Ala Val Pro Asn Gly Thr Leu Val Lys Thr
             35                  40                  45

Ile Thr Asn Asp Gln Ile Glu Val Thr Asn Ala Thr Glu Leu Val Gln
         50                  55                  60

Ser Ser Ser Thr Gly Arg Ile Cys Asp Ser Pro His Arg Ile Leu Asp
65                  70                  75                  80

Gly Lys Asn Cys Thr Leu Ile Asp Ala Leu Leu Gly Asp Pro His Cys
                 85                  90                  95

Asp Gly Phe Gln Asn Lys Glu Trp Asp Leu Phe Val Glu Arg Ser Lys
```

-continued

|     |     |     |     |     |     |     |     |     |     |     |     |     |     |
|-----|-----|-----|-----|-----|-----|-----|-----|-----|-----|-----|-----|-----|-----|
|     |     | 100 |     |     |     | 105 |     |     |     | 110 |     |     |     |
| Ala | Tyr | Ser | Asn | Cys | Tyr | Pro | Tyr | Asp | Val | Pro | Asp | Ala | Ser | Leu |
|     |     | 115 |     |     |     | 120 |     |     |     | 125 |     |     |     |
| Arg | Ser | Leu | Val | Ala | Ser | Ser | Gly | Thr | Leu | Glu | Phe | Ile | Asn | Glu | Asp |
|     | 130 |     |     |     | 135 |     |     |     | 140 |     |     |     |
| Phe | Asn | Trp | Thr | Gly | Val | Ala | Gln | Asp | Gly | Gly | Ser | Tyr | Ala | Cys | Lys |
| 145 |     |     |     | 150 |     |     |     | 155 |     |     |     | 160 |
| Arg | Gly | Ser | Val | Asn | Ser | Phe | Phe | Ser | Arg | Leu | Asn | Trp | Leu | His | Lys |
|     |     |     |     | 165 |     |     |     | 170 |     |     |     | 175 |
| Ser | Glu | Tyr | Lys | Tyr | Pro | Ala | Leu | Asn | Val | Thr | Met | Pro | Asn | Asn | Gly |
|     |     |     | 180 |     |     |     | 185 |     |     |     | 190 |
| Lys | Phe | Asp | Lys | Leu | Tyr | Ile | Trp | Gly | Val | His | His | Pro | Ser | Thr | Asp |
|     |     | 195 |     |     |     | 200 |     |     |     | 205 |     |     |     |
| Arg | Asp | Gln | Thr | Ser | Leu | Tyr | Val | Arg | Ala | Ser | Gly | Arg | Val | Thr | Val |
|     | 210 |     |     |     | 215 |     |     |     | 220 |     |     |     |
| Ser | Thr | Lys | Arg | Ser | Gln | Gln | Thr | Val | Thr | Pro | Asn | Ile | Gly | Ser | Arg |
| 225 |     |     |     | 230 |     |     |     | 235 |     |     |     | 240 |
| Pro | Trp | Val | Arg | Gly | Gln | Ser | Ser | Arg | Ile | Ser | Ile | Tyr | Trp | Thr | Ile |
|     |     |     |     | 245 |     |     |     | 250 |     |     |     | 255 |
| Val | Lys | Pro | Gly | Asp | Ile | Leu | Leu | Ile | Asn | Ser | Thr | Gly | Asn | Leu | Ile |
|     |     |     | 260 |     |     |     | 265 |     |     |     | 270 |
| Ala | Pro | Arg | Gly | Tyr | Phe | Lys | Ile | Arg | Asn | Gly | Lys | Ser | Ser | Ile | Met |
|     |     | 275 |     |     |     | 280 |     |     |     | 285 |     |     |     |
| Arg | Ser | Asp | Ala | Pro | Ile | Gly | Thr | Cys | Ser | Ser | Glu | Cys | Ile | Thr | Pro |
|     | 290 |     |     |     | 295 |     |     |     | 300 |     |     |     |
| Asn | Gly | Ser | Ile | Pro | Asn | Asp | Lys | Pro | Phe | Gln | Asn | Val | Asn | Arg | Ile |
| 305 |     |     |     | 310 |     |     |     | 315 |     |     |     | 320 |
| Thr | Tyr | Gly | Ala | Cys | Pro | Arg | Tyr | Val | Lys | Gln | Asn | Thr | Leu | Lys | Leu |
|     |     |     |     | 325 |     |     |     | 330 |     |     |     | 335 |
| Ala | Thr | Gly | Met | Arg | Asn | Val | Pro | Glu | Lys | Gln | Thr | Arg | Gly | Ile | Phe |
|     |     |     | 340 |     |     |     | 345 |     |     |     | 350 |
| Gly | Ala | Ile | Ala | Gly | Phe | Ile | Glu | Asn | Gly | Trp | Glu | Gly | Met | Val | Asp |
|     |     | 355 |     |     |     | 360 |     |     |     | 365 |     |     |     |
| Gly | Trp | Tyr | Gly | Phe | Arg | His | Gln | Asn | Ser | Glu | Gly | Thr | Gly | Gln | Ala |
|     | 370 |     |     |     | 375 |     |     |     | 380 |     |     |     |
| Ala | Asp | Leu | Lys | Ser | Thr | Gln | Ala | Ala | Ile | Asp | Gln | Ile | Asn | Gly | Lys |
| 385 |     |     |     | 390 |     |     |     | 395 |     |     |     | 400 |
| Leu | Asn | Arg | Leu | Ile | Glu | Lys | Thr | Asn | Glu | Lys | Phe | His | Gln | Ile | Glu |
|     |     |     |     | 405 |     |     |     | 410 |     |     |     | 415 |
| Lys | Glu | Phe | Ser | Glu | Val | Glu | Gly | Arg | Ile | Gln | Asp | Leu | Glu | Lys | Tyr |
|     |     |     | 420 |     |     |     | 425 |     |     |     | 430 |
| Val | Glu | Asp | Thr | Lys | Ile | Asp | Leu | Trp | Ser | Tyr | Asn | Ala | Glu | Leu | Leu |
|     |     | 435 |     |     |     | 440 |     |     |     | 445 |     |     |     |
| Val | Ala | Leu | Glu | Asn | Gln | His | Thr | Ile | Asp | Leu | Thr | Asp | Ser | Glu | Met |
|     | 450 |     |     |     | 455 |     |     |     | 460 |     |     |     |
| Asn | Lys | Leu | Phe | Glu | Lys | Thr | Arg | Lys | Gln | Leu | Arg | Glu | Asn | Ala | Glu |
| 465 |     |     |     | 470 |     |     |     | 475 |     |     |     | 480 |
| Asp | Met | Gly | Asn | Gly | Cys | Phe | Lys | Ile | Tyr | His | Lys | Cys | Asp | Asn | Ala |
|     |     |     |     | 485 |     |     |     | 490 |     |     |     | 495 |
| Cys | Ile | Gly | Ser | Ile | Arg | Asn | Gly | Thr | Tyr | Asp | His | Asp | Val | Tyr | Arg |
|     |     |     | 500 |     |     |     | 505 |     |     |     | 510 |
| Asp | Glu | Ala | Leu | Asn | Asn | Arg | Phe | Gln | Ile | Lys | Gly | Val | Glu | Leu | Lys |
|     |     | 515 |     |     |     | 520 |     |     |     | 525 |     |     |     |

| Ser | Gly | Tyr | Lys | Asp | Trp | Ile | Leu | Trp | Ile | Ser | Phe | Ala | Ile | Ser | Cys |
|-----|-----|-----|-----|-----|-----|-----|-----|-----|-----|-----|-----|-----|-----|-----|-----|
|     | 530 |     |     |     |     | 535 |     |     |     |     | 540 |     |     |     |     |

| Phe | Leu | Leu | Cys | Val | Val | Leu | Leu | Gly | Phe | Ile | Met | Trp | Ala | Cys | Gln |
|-----|-----|-----|-----|-----|-----|-----|-----|-----|-----|-----|-----|-----|-----|-----|-----|
| 545 |     |     |     | 550 |     |     |     |     | 555 |     |     |     |     |     | 560 |

| Lys | Gly | Asn | Ile | Arg | Cys | Asn | Ile | Cys | Ile |
|-----|-----|-----|-----|-----|-----|-----|-----|-----|-----|
|     |     |     |     | 565 |     |     |     |     | 570 |

( 2 ) INFORMATION FOR SEQ ID NO:8:

( i ) SEQUENCE CHARACTERISTICS:
        ( A ) LENGTH: 1766 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Influenza virus
        ( C ) INDIVIDUAL ISOLATE: A/Texas/36/91 rHA ( i x ) FEATURE:
        ( A ) NAME/KEY: polyhedrin mRNA leader (partial)
        ( B ) LOCATION: 1 to 18

( i x ) FEATURE:
        ( A ) NAME/KEY: coding region for AcNPV 61K protein signal
            peptide
        ( B ) LOCATION: 19 to 72

( i x ) FEATURE:
        ( A ) NAME/KEY: SmaI restriction site
        ( B ) LOCATION: 76 to 81

( i x ) FEATURE:
        ( A ) NAME/KEY: KpnI restriction site
        ( B ) LOCATION: 82 to 87

( i x ) FEATURE:
        ( A ) NAME/KEY: SmaI restriction site
        ( B ) LOCATION: 88 to 93

( i x ) FEATURE:
        ( A ) NAME/KEY: coding region for mature rHA
        ( B ) LOCATION: 73 to 1734

( i x ) FEATURE:
        ( A ) NAME/KEY: KpnI restriction site
        ( B ) LOCATION: 1744 to 1749

( i x ) FEATURE:
        ( A ) NAME/KEY: BglII restriction site
        ( B ) LOCATION: 1750 to 1755

( i x ) FEATURE:
        ( A ) NAME/KEY: unversal translation termination signal
        ( B ) LOCATION: 1756 to 1766

( x i ) SEQUENCE DESCRIPTION: SEQ ID NO:8:

```
TAAAAAACC  TATAAATAAT  GCCCTTGTAC  AAATTGTTAA  ACGTTTTGTG  GTTGGTCGCC      60

GTTTCTAACG  CGATTCCCGG  GGGTACCCCC  GGGGACACAA  TATGTATAGG  CTACCATGCG     120

AACAACTCAA  CCGACACTGT  TGACACAGTA  CTTGAGAAGA  ACGTGACAGT  GACACACTCT     180

GTCAACCTAC  TTGAGGACAG  TCACAACGGA  AAACTATGTC  GACTAAAGGG  AATAGCCCCA     240

CTACAATTGG  GTAATTGCAG  CGTTGCCGGA  TGGATCTTAG  GAAACCCAAA  ATGCGAATCA     300

CTGTTTTCTA  AGGAATCATG  GTCCTACATT  GCAGAAACAC  CAAACCCTGA  GAATGGAACA     360

TGTTACCCAG  GGTATTTCGC  CGACTATGAG  GAACTGAGGG  AGCAATTGAG  TTCAGTATCA     420
```

-continued

```
TCATTCGAGA   GATTCGAAAT   ATTCCCCAAA   GAAAGCTCAT   GGCCCAACCA   CACCGTAACC    480
AAAGGAGTAA   CGAGATCATG   CTCCCATAAT   GGGAAAAGCA   GTTTTTACAG   AAATTTGCTA    540
TGGCTGACGG   AGAAGAATGG   CTTGTACCCA   AATCTGAGCA   AGTCCTATGT   AAACAACAAA    600
GAGAAAGAAG   TCCTTGTACT   ATGGGGTGTT   CATCACCCGT   CTAACATAAG   GGACCAAAGG    660
GCCATCTATC   ATACAGAAAA   TGCTTATGTC   TCTGTAGTGT   CTTCACATTA   TAGCAGAAGA    720
TTCACCCCAG   AAATAGCAAA   AAGACCCAAA   GTAAGAGATC   AAGAAGGAAG   AATTAACTAC    780
TACTGGACTC   TGCTGGAACC   CGGGGACACA   ATAATATTTG   AGGCAAATGG   AAATCTAATA    840
GCGCCATGGT   ATGCTTTCGC   ACTGAGTAGA   GGCTTTGGGT   CAGGAATCAT   CACCTCAAAC    900
GCATCAATGG   ATGAATGTGA   CGCGAAGTGT   CAAACACCCC   AGGGAGCTAT   AAACAGTAGT    960
CTTCCTTTCC   AGAATGTACA   CCCAGTCACA   ATAGGAGAGT   GTCCAAAGTA   TGTCAGGAGT   1020
ACAAAATTAA   GGATGGTTAC   AGGACTAAGG   AACATCCCAT   CCATTCAATC   CAGAGGTTTG   1080
TTTGGAGCCA   TTGCCGGTTT   CATTGAAGGG   GGGTGGACTG   GAATGATAGA   TGGATGGTAT   1140
GGTTATCATC   ATCAGAATGA   ACAAGGATCT   GGCTATGCTG   CGGACCAAAA   AAGCACACAA   1200
AATGCCATTA   ACGGGATTAC   AAACAAGGTG   AATTCTGTAA   TCGAGAAAAT   GAACACTCAA   1260
TTCACAGCTG   TGGGCAAAGA   ATTCAACAAA   TTAGAAAGAA   GGATGGAAAA   CTTAAATAAA   1320
AAAGTTGATG   ATGGATTTCT   GGACATTTGG   ACATATAATG   CAGAATTGTT   GGTTCTACTG   1380
GAAAATGGAA   GGACTTTGGA   TTTTCATGAC   TCAAATGTGA   AGAATCTGTA   TGAGAAAGTA   1440
AAAAGCCAAT   TGAAGAATAA   TGCCAAAGAA   ATAGGGAACG   GGTGTTTTGA   ATTCTATCAC   1500
AAGTGTAACA   ATGAATGCAT   GGAAAGTGTG   AAAAATGGAA   CTTATGACTA   TCCAAAATAT   1560
TCCGAAGAAT   CAAAGTTAAA   CAGGGGAAAA   ATTGATGGAG   TGAAATTGGA   ATCAATGGGA   1620
GTCTATCAGA   TTCTGGCGAT   CTACTCAACT   GTCGCCAGTT   CACTGGTGCT   TTTGGTCTCC   1680
CTGGGGGCAA   TCAGCTTCTG   GATGTGTTCT   AATGGGTCTT   TGCAGTGCAG   AATATGAATC   1740
TGAGGTACCA   GATCTTAATT   AATTAA                                               1766
```

( 2 ) INFORMATION FOR SEQ ID NO:9:

( i ) SEQUENCE CHARACTERISTICS:
        ( A ) LENGTH: 572 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Influenza virus
        ( C ) INDIVIDUAL ISOLATE: A/Texas/36/91 rHA ( i x ) FEATURE:
        ( A ) NAME/KEY: AcNPV 61K protein signal sequence
        ( B ) LOCATION: 1 to 18

( i x ) FEATURE:
        ( A ) NAME/KEY: mature rHA
        ( B ) LOCATION: 19 to 554

( x i ) SEQUENCE DESCRIPTION: SEQ ID NO:9:

```
Met   Pro   Leu   Tyr   Lys   Leu   Leu   Asn   Val   Leu   Trp   Leu   Val   Ala   Val   Ser
 1                 5                             10                            15
```

```
Asn Ala Ile Pro Gly Gly Thr Pro Gly Asp Thr Ile Cys Ile Gly Tyr
             20                  25                      30

His Ala Asn Asn Ser Thr Asp Thr Val Asp Thr Val Leu Glu Lys Asn
         35              40              45

Val Thr Val Thr His Ser Val Asn Leu Leu Glu Asp Ser His Asn Gly
     50              55              60

Lys Leu Cys Arg Leu Lys Gly Ile Ala Pro Leu Gln Leu Gly Asn Cys
 65              70              75                              80

Ser Val Ala Gly Trp Ile Leu Gly Asn Pro Lys Cys Glu Ser Leu Phe
             85              90                      95

Ser Lys Glu Ser Trp Ser Tyr Ile Ala Glu Thr Pro Asn Pro Glu Asn
             100             105             110

Gly Thr Cys Tyr Pro Gly Tyr Phe Ala Asp Tyr Glu Glu Leu Arg Glu
         115             120             125

Gln Leu Ser Ser Val Ser Ser Phe Glu Arg Phe Glu Ile Phe Pro Lys
     130             135             140

Glu Ser Ser Trp Pro Asn His Thr Val Thr Lys Gly Val Thr Arg Ser
145             150             155                          160

Cys Ser His Asn Gly Lys Ser Ser Phe Tyr Arg Asn Leu Leu Trp Leu
             165             170                          175

Thr Glu Lys Asn Gly Leu Tyr Pro Asn Leu Ser Lys Ser Tyr Val Asn
             180             185                      190

Asn Lys Glu Lys Glu Val Leu Val Leu Trp Gly Val His His Pro Ser
         195             200             205

Asn Ile Arg Asp Gln Arg Ala Ile Tyr His Thr Glu Asn Ala Tyr Val
     210             215             220

Ser Val Val Ser Ser His Tyr Ser Arg Arg Phe Thr Pro Glu Ile Ala
225             230             235                          240

Lys Arg Pro Lys Val Arg Asp Gln Glu Gly Arg Ile Asn Tyr Tyr Trp
             245             250             255

Thr Leu Leu Glu Pro Gly Asp Thr Ile Ile Phe Glu Ala Asn Gly Asn
             260             265             270

Leu Ile Ala Pro Trp Tyr Ala Phe Ala Leu Ser Arg Gly Phe Gly Ser
         275             280             285

Gly Ile Ile Thr Ser Asn Ala Ser Met Asp Glu Cys Asp Ala Lys Cys
     290             295             300

Gln Thr Pro Gln Gly Ala Ile Asn Ser Ser Leu Pro Phe Gln Asn Val
305             310             315                          320

His Pro Val Thr Ile Gly Glu Cys Pro Lys Tyr Val Arg Ser Thr Lys
             325             330             335

Leu Arg Met Val Thr Gly Leu Arg Asn Ile Pro Ser Ile Gln Ser Arg
             340             345             350

Gly Leu Phe Gly Ala Ile Ala Gly Phe Ile Glu Gly Gly Trp Thr Gly
         355             360             365

Met Ile Asp Gly Trp Tyr Gly Tyr His His Gln Asn Glu Gln Gly Ser
     370             375             380

Gly Tyr Ala Ala Asp Gln Lys Ser Thr Gln Asn Ala Ile Asn Gly Ile
385             390             395                          400

Thr Asn Lys Val Asn Ser Val Ile Glu Lys Met Asn Thr Gln Phe Thr
             405             410             415

Ala Val Gly Lys Glu Phe Asn Lys Leu Glu Arg Arg Met Glu Asn Leu
             420             425             430

Asn Lys Lys Val Asp Asp Gly Phe Leu Asp Ile Trp Thr Tyr Asn Ala
```

|     |     |     | 435 |     |     |     | 440 |     |     |     | 445 |     |     |     |
| --- | --- | --- | --- | --- | --- | --- | --- | --- | --- | --- | --- | --- | --- | --- |
| Glu | Leu | Leu | Val | Leu | Leu | Glu | Asn | Gly | Arg | Thr | Leu | Asp | Phe | His | Asp |
|     | 450 |     |     |     |     | 455 |     |     |     |     | 460 |     |     |     |
| Ser | Asn | Val | Lys | Asn | Leu | Tyr | Glu | Lys | Val | Lys | Ser | Gln | Leu | Lys | Asn |
| 465 |     |     |     |     | 470 |     |     |     |     | 475 |     |     |     |     | 480 |
| Asn | Ala | Lys | Glu | Ile | Gly | Asn | Gly | Cys | Phe | Glu | Phe | Tyr | His | Lys | Cys |
|     |     |     |     | 485 |     |     |     |     | 490 |     |     |     |     | 495 |     |
| Asn | Asn | Glu | Cys | Met | Glu | Ser | Val | Lys | Asn | Gly | Thr | Tyr | Asp | Tyr | Pro |
|     |     |     | 500 |     |     |     |     | 505 |     |     |     |     | 510 |     |     |
| Lys | Tyr | Ser | Glu | Glu | Ser | Lys | Leu | Asn | Arg | Gly | Lys | Ile | Asp | Gly | Val |
|     |     | 515 |     |     |     |     | 520 |     |     |     |     | 525 |     |     |     |
| Lys | Leu | Glu | Ser | Met | Gly | Val | Tyr | Gln | Ile | Leu | Ala | Ile | Tyr | Ser | Thr |
|     | 530 |     |     |     |     | 535 |     |     |     |     | 540 |     |     |     |     |
| Val | Ala | Ser | Ser | Leu | Val | Leu | Leu | Val | Ser | Leu | Gly | Ala | Ile | Ser | Phe |
| 545 |     |     |     |     | 550 |     |     |     |     | 555 |     |     |     |     | 560 |
| Trp | Met | Cys | Ser | Asn | Gly | Ser | Leu | Gln | Cys | Arg | Ile |     |     |     |     |
|     |     |     |     | 565 |     |     |     |     | 570 |     |     |     |     |     |     |

( 2 ) INFORMATION FOR SEQ ID NO:10:

( i ) SEQUENCE CHARACTERISTICS:
        ( A ) LENGTH: 1799 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
        ( A ) ORGANISM: Influenza virus
        ( C ) INDIVIDUAL ISOLATE: B/Panama/45/90 rHA ( i x ) FEATURE:
        ( A ) NAME/KEY: polyhedrin mRNA leader (partial)
        ( B ) LOCATION: 1 to 18

( i x ) FEATURE:
        ( A ) NAME/KEY: coding region for HA signal peptide
            sequence
        ( B ) LOCATION: 19 to 69

( i x ) FEATURE:
        ( A ) NAME/KEY: SmaI restriction site
        ( B ) LOCATION: 22 to 27

( i x ) FEATURE:
        ( A ) NAME/KEY: coding region for mature rHA
        ( B ) LOCATION: 70 to 1773

( i x ) FEATURE:
        ( A ) NAME/KEY: KpnI restriction site
        ( B ) LOCATION: 1777 to 1782

( i x ) FEATURE:
        ( A ) NAME/KEY: BglII restriction site
        ( B ) LOCATION: 1783 to 1788

( i x ) FEATURE:
        ( A ) NAME/KEY: unversal translation termination signal
        ( B ) LOCATION: 1789 to 1799

( x i ) SEQUENCE DESCRIPTION: SEQ ID NO:10:

| TAAAAAACC | TATAAATAAT | GCCCGGGAAG | GCAATAATTG | TACTACTCAT | GGTAGTAACA | 60 |
| --- | --- | --- | --- | --- | --- | --- |
| TCCAACGCAG | ATCGAATCTG | CACTGGGATA | ACATCTTCAA | ACTCACCTCA | TGTGGTCAAA | 120 |

-continued

| | | | | | | |
|---|---|---|---|---|---|---|
| ACAGCTACTC | AAGGGGAAGT | CAATGTGACT | GGTGTGATAC | CACTGACAAC | AACACCAACA | 180 |
| AAATCTCATT | TTGCAAATCT | AAAAGGAACA | AAGACCAGAG | GGAAACTATG | CCCAAACTGT | 240 |
| CTCAACTGCA | CAGATCTGGA | TGTGGCCTTG | GGCAGACCAA | TGTGTGTGGG | GACCACACCT | 300 |
| TCGGCAAAAG | CTTCAATACT | CCACGAAGTC | AGACCTGTTA | CATCCGGGTG | CTTTCCTATA | 360 |
| ATGCACGACA | GAACAAAAAT | CAGACAGCTA | CCCAATCTTC | TCAGAGGATA | TGAAAATATC | 420 |
| AGATTATCAA | CCCAAAACGT | TATCAACGCA | GAAAGAGCAC | CAGGAGGACC | CTACAGACTT | 480 |
| GGAACCTCAG | GATCTTGCCC | TAACGTTACC | AGTAGAGACG | GATTCTTCGC | AACAATGGCT | 540 |
| TGGGCTGTCC | CAAGGGACAA | CAAAACAGCA | ACGAATCCAC | TAACAGTAGA | AGTACCATAC | 600 |
| ATTTGTACCA | AAGGAGAAGA | CCAAATTACT | GTTTGGGGGT | TCCATTCTGA | TAACAAAATC | 660 |
| CAAATGAAAA | ACCTCTATGG | AGACTCAAAT | CCTCAAAAGT | TCACCTCATC | TGCCAATGGA | 720 |
| GTAACCACAC | ATTATGTTTC | TCAGATTGGT | GGCTTCCCAA | ATCAAACAGA | AGACGGAGGG | 780 |
| CTACCACAAA | GCGGCAGAAT | TGTTGTTGAT | TACATGGTGC | AAAAACCTGG | GAAAACAGGA | 840 |
| ACAATTGTCT | ATCAAAGAGG | TGTTTTGTTG | CCTCAAAAGG | TGTGGTGCGC | AAGTGGCAGG | 900 |
| AGCAAGGTAA | TAAAAGGGTC | CTTGCCTTTA | ATTGGTGAAG | CAGATTGCCT | TCACGAAAAA | 960 |
| TACGGTGGAT | TAAACAAAAG | CAAGCCTTAC | TACACAGGAG | AACATGCAAA | AGCCATAGGA | 1020 |
| AATTGCCCAA | TATGGGTGAA | AACACCTTTG | AAGCTTGCCA | ATGGAACCAA | ATATAGACCT | 1080 |
| CCTGCAAAAC | TATTAAAGGA | AAGGGGTTTC | TTCGGAGCTA | TTGCTGGTTT | CTTAGAAGGA | 1140 |
| GGATGGGAAG | GAATGATTGC | AGGTTGGCAC | GGATACACAT | CTCATGGAGC | ACATGGAGTG | 1200 |
| GCAGTGGCAG | CAGACCTTAA | GAGTACGCAA | GAAGCCATAA | ACAAGATAAC | AAAAAATCTC | 1260 |
| AATTCTTTGA | GTGAGCTAGA | AGTAAAGAAT | CTTCAAAGAC | TAAGTGGTGC | CATGGATGAA | 1320 |
| CTCCACAACG | AAATACTCGA | GCTGGATGAG | AAAGTGGATG | ATCTCAGAGC | TGACACAATA | 1380 |
| AGCTCGCAAA | TAGAGCTTGC | AGTCTTGCTT | TCCAACGAAG | GAATAATAAA | CAGTGAAGAT | 1440 |
| GAGCATCTAT | TGGCACTTGA | GAGAAAACTA | AGAAAATGC | TGGGTCCCTC | TGCTGTAGAC | 1500 |
| ATAGGGAATG | GATGCTTCGA | AACCAAACAC | AAGTGCAACC | AGACCTGCTT | AGACAGGATA | 1560 |
| GCTGCTGGCA | CCTTTAATGC | AGGAGAATTT | TCTCTTCCCA | CTTTTGATTC | ACTGAATATT | 1620 |
| ACTGCTGCAT | CTTTAAATGA | TGATGGATTG | GATAATCATA | CTATACTGCT | CTACTACTCA | 1680 |
| ACTGCTGCTT | CTAGTTTGGC | TGTAACATTG | ATGATAGCTA | TTTTTATTGT | TTATATGGTC | 1740 |
| TCCAGAGACA | ATGTTTCTTG | TTCCATCTGT | CTGTGAGGTA | CCAGATCTTA | ATTAATTAA | 1799 |

( 2 ) INFORMATION FOR SEQ ID NO:11:

( i ) SEQUENCE CHARACTERISTICS:
        ( A ) LENGTH: 585 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Influenza virus
        ( C ) INDIVIDUAL ISOLATE: B/Panama/45/90 rHA ( i x ) FEATURE:
        ( A ) NAME/KEY: HA signal peptide
        ( B ) LOCATION: 1 to 17

( i x ) FEATURE:
   ( A ) NAME/KEY: mature rHA
   ( B ) LOCATION: 18 to 568

( x i ) SEQUENCE DESCRIPTION: SEQ ID NO:11:

| Met | Pro | Gly | Lys | Ala | Ile | Ile | Val | Leu | Leu | Met | Val | Val | Thr | Ser | Asn |
|---|---|---|---|---|---|---|---|---|---|---|---|---|---|---|---|
| 1 | | | | 5 | | | | | 10 | | | | | 15 | |
| Ala | Asp | Arg | Ile | Cys | Thr | Gly | Ile | Thr | Ser | Ser | Asn | Ser | Pro | His | Val |
| | | | 20 | | | | | 25 | | | | | 30 | | |
| Val | Lys | Thr | Ala | Thr | Gln | Gly | Glu | Val | Asn | Val | Thr | Gly | Val | Ile | Pro |
| | | 35 | | | | | 40 | | | | | 45 | | | |
| Leu | Thr | Thr | Thr | Pro | Thr | Lys | Ser | His | Phe | Ala | Asn | Leu | Lys | Gly | Thr |
| | | 50 | | | | 55 | | | | | 60 | | | | |
| Lys | Thr | Arg | Gly | Lys | Leu | Cys | Pro | Asn | Cys | Leu | Asn | Cys | Thr | Asp | Leu |
| 65 | | | | | 70 | | | | 75 | | | | | | 80 |
| Asp | Val | Ala | Leu | Gly | Arg | Pro | Met | Cys | Val | Gly | Thr | Thr | Pro | Ser | Ala |
| | | | | 85 | | | | | 90 | | | | | 95 | |
| Lys | Ala | Ser | Ile | Leu | His | Glu | Val | Arg | Pro | Val | Thr | Ser | Gly | Cys | Phe |
| | | | 100 | | | | | 105 | | | | | 110 | | |
| Pro | Ile | Met | His | Asp | Arg | Thr | Lys | Ile | Arg | Gln | Leu | Pro | Asn | Leu | Leu |
| | | 115 | | | | | 120 | | | | | 125 | | | |
| Arg | Gly | Tyr | Glu | Asn | Ile | Arg | Leu | Ser | Thr | Gln | Asn | Val | Ile | Asn | Ala |
| | 130 | | | | | 135 | | | | | 140 | | | | |
| Glu | Arg | Ala | Pro | Gly | Gly | Pro | Tyr | Arg | Leu | Gly | Thr | Ser | Gly | Ser | Cys |
| 145 | | | | | 150 | | | | | 155 | | | | | 160 |
| Pro | Asn | Val | Thr | Ser | Arg | Asp | Gly | Phe | Phe | Ala | Thr | Met | Ala | Trp | Ala |
| | | | | 165 | | | | | 170 | | | | | 175 | |
| Val | Pro | Arg | Asp | Asn | Lys | Thr | Ala | Thr | Asn | Pro | Leu | Thr | Val | Glu | Val |
| | | | 180 | | | | | 185 | | | | | 190 | | |
| Pro | Tyr | Ile | Cys | Thr | Lys | Gly | Glu | Asp | Gln | Ile | Thr | Val | Trp | Gly | Phe |
| | | 195 | | | | | 200 | | | | | 205 | | | |
| His | Ser | Asp | Asn | Lys | Ile | Gln | Met | Lys | Asn | Leu | Tyr | Gly | Asp | Ser | Asn |
| | 210 | | | | | 215 | | | | | 220 | | | | |
| Pro | Gln | Lys | Phe | Thr | Ser | Ser | Ala | Asn | Gly | Val | Thr | Thr | His | Tyr | Val |
| 225 | | | | | 230 | | | | | 235 | | | | | 240 |
| Ser | Gln | Ile | Gly | Gly | Phe | Pro | Asn | Gln | Thr | Glu | Asp | Gly | Gly | Leu | Pro |
| | | | | 245 | | | | | 250 | | | | | 255 | |
| Gln | Ser | Gly | Arg | Ile | Val | Val | Asp | Tyr | Met | Val | Gln | Lys | Pro | Gly | Lys |
| | | | 260 | | | | | 265 | | | | | 270 | | |
| Thr | Gly | Thr | Ile | Val | Tyr | Gln | Arg | Gly | Val | Leu | Leu | Pro | Gln | Lys | Val |
| | | 275 | | | | | 280 | | | | | 285 | | | |
| Trp | Cys | Ala | Ser | Gly | Arg | Ser | Lys | Val | Ile | Lys | Gly | Ser | Leu | Pro | Leu |
| | 290 | | | | | 295 | | | | | 300 | | | | |
| Ile | Gly | Glu | Ala | Asp | Cys | Leu | His | Glu | Lys | Tyr | Gly | Gly | Leu | Asn | Lys |
| 305 | | | | | 310 | | | | | 315 | | | | | 320 |
| Ser | Lys | Pro | Tyr | Tyr | Thr | Gly | Glu | His | Ala | Lys | Ala | Ile | Gly | Asn | Cys |
| | | | | 325 | | | | | 330 | | | | | 335 | |
| Pro | Ile | Trp | Val | Lys | Thr | Pro | Leu | Lys | Leu | Ala | Asn | Gly | Thr | Lys | Tyr |
| | | | 340 | | | | | 345 | | | | | 350 | | |
| Arg | Pro | Pro | Ala | Lys | Leu | Leu | Lys | Glu | Arg | Gly | Phe | Phe | Gly | Ala | Ile |
| | | 355 | | | | | 360 | | | | | 365 | | | |
| Ala | Gly | Phe | Leu | Glu | Gly | Gly | Trp | Glu | Gly | Met | Ile | Ala | Gly | Trp | His |
| | 370 | | | | | 375 | | | | | 380 | | | | |
| Gly | Tyr | Thr | Ser | His | Gly | Ala | His | Gly | Val | Ala | Val | Ala | Ala | Asp | Leu |

-continued

| | | 385 | | | | 390 | | | | 395 | | | | 400 | |
|---|---|---|---|---|---|---|---|---|---|---|---|---|---|---|---|
|Lys|Ser|Thr|Gln|Glu|Ala|Ile|Asn|Lys|Ile|Thr|Lys|Asn|Leu|Asn|Ser|
| | | | |405| | | |410| | | |415| | | |
|Leu|Ser|Glu|Leu|Glu|Val|Lys|Asn|Leu|Gln|Arg|Leu|Ser|Gly|Ala|Met|
| | | |420| | | |425| | | |430| | | | |
|Asp|Glu|Leu|His|Asn|Glu|Ile|Leu|Glu|Leu|Asp|Glu|Lys|Val|Asp|Asp|
| | |435| | | |440| | | |445| | | | | |
|Leu|Arg|Ala|Asp|Thr|Ile|Ser|Ser|Gln|Ile|Glu|Leu|Ala|Val|Leu|Leu|
| |450| | | |455| | | |460| | | | | | |
|Ser|Asn|Glu|Gly|Ile|Ile|Asn|Ser|Glu|Asp|Glu|His|Leu|Leu|Ala|Leu|
|465| | | |470| | | |475| | | | |480| | |
|Glu|Arg|Lys|Leu|Lys|Lys|Met|Leu|Gly|Pro|Ser|Ala|Val|Asp|Ile|Gly|
| | | |485| | | |490| | | | |495| | | |
|Asn|Gly|Cys|Phe|Glu|Thr|Lys|His|Lys|Cys|Asn|Gln|Thr|Cys|Leu|Asp|
| | |500| | | |505| | | | |510| | | | |
|Arg|Ile|Ala|Ala|Gly|Thr|Phe|Asn|Ala|Gly|Glu|Phe|Ser|Leu|Pro|Thr|
| |515| | | |520| | | | |525| | | | | |
|Phe|Asp|Ser|Leu|Asn|Ile|Thr|Ala|Ala|Ser|Leu|Asn|Asp|Asp|Gly|Leu|
|530| | | | |535| | | |540| | | | | | |
|Asp|Asn|His|Thr|Ile|Leu|Leu|Tyr|Tyr|Ser|Thr|Ala|Ala|Ser|Ser|Leu|
|545| | | |550| | | |555| | | | | |560| |
|Ala|Val|Thr|Leu|Met|Ile|Ala|Ile|Phe|Ile|Val|Tyr|Met|Val|Ser|Arg|
| | | |565| | | |570| | | | |575| | | |
|Asp|Asn|Val|Ser|Cys|Ser|Ile|Cys|Leu| | | | | | | |
| | |580| | | |585| | | | | | | | | |

( 2 ) INFORMATION FOR SEQ ID NO:12:

( i ) SEQUENCE CHARACTERISTICS:
        ( A ) LENGTH: 1811 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Influenza virus
        ( C ) INDIVIDUAL ISOLATE: B/Netherlands/13/94 rHA ( i x ) FEATURE:
        ( A ) NAME/KEY: polyhedrin mRNA leader (partial)
        ( B ) LOCATION: 1 to 18

( i x ) FEATURE:
        ( A ) NAME/KEY: coding region for AcNPV 61K protein signal
            sequence
        ( B ) LOCATION: 19 to 72

( i x ) FEATURE:
        ( A ) NAME/KEY: SmaI restriction site
        ( B ) LOCATION: 76 to 81

( i x ) FEATURE:
        ( A ) NAME/KEY: coding region for mature rHA
        ( B ) LOCATION: 73 to 1785

( i x ) FEATURE:
        ( A ) NAME/KEY: KpnI restriction site
        ( B ) LOCATION: 1789 to 1794

( i x ) FEATURE:
        ( A ) NAME/KEY: BglII restriction site (B) LOCATION: 1795 to 1800

(ix) FEATURE:
(A) NAME/KEY: unversal translation termination signal
(B) LOCATION: 1801 to 1811

(xi) SEQUENCE DESCRIPTION: SEQ ID NO:12:

| | | | | | | |
|---|---|---|---|---|---|---|
| TAAAAAAACC | TATAAATAAT | GCCCTTGTAC | AAATTGTTAA | ACGTTTTGTG | GTTGGTCGCC | 60 |
| GTTTCTAACG | CGATTCCCGG | GGATCGAATC | TGCACTGGGA | TAACATCTTC | AAAATCACCT | 120 |
| CATGTAGTCA | AAACAGCTAC | TCAAGGGGAG | GTCAATGTGA | CTGGTGTGAT | ACCACTGACG | 180 |
| ACAACACCAA | CAAAATCTCA | TTTTGCAAAT | CTCAAAGGAA | CAAAGACCAG | AGGGAAACTA | 240 |
| TGCCCAAACT | GTCTCAACTG | CACAGATCTG | GATGTGGCCT | TGGGCAGACC | AATGTGTGTG | 300 |
| GGGATCACAC | CTTCGGCAAA | AGCTTCAATA | CTCCACGAAG | TCAGACCTGT | TACATCCGGG | 360 |
| TGCTTTCCTA | TAATGCATGA | CAGAACAAAA | ATCAGACAGC | TACCCAATCT | TCTCAGAGGA | 420 |
| TATGAAAACA | TCAGACTATC | AACCCAAAAC | GTTATCAACG | CAGAAAAGGC | ACCAGGAGGA | 480 |
| CCCTACAGAC | TTGGAACCTC | AGGATCTTGC | CCTAACGTTA | CCAGTAGAAC | CGGATTCTTC | 540 |
| GCAACAATGG | CTTGGGCTGT | CCCAAGGGAC | AACAAAACAG | CAACGAATCC | ACTAACAGTA | 600 |
| GAAGTACCAT | ACATTTGTAC | GAAAGGAGAA | GACCAAATTA | CTGTTTGGGG | GTTCCATTCT | 660 |
| GATAACAAAA | CCCAAATGAA | AAACCTCTAT | GGAGACTCAA | ATCCTCAAAA | GTTCACCTCA | 720 |
| TCTGCCAATG | GAGTAACCAC | ACATTATGTT | TCTCAGATTG | GTGGCTTCCC | AGATCAAACA | 780 |
| GAAGACGGAG | GACTACCACA | AAGCGGCAGA | ATTGTTGTTG | ATTACATGGT | GCAAAAACCT | 840 |
| GGGAAAACAG | GAACAATTGT | CTATCAAAGA | GGTATTTTGT | TGCCTCAAAA | GGTGTGGTGC | 900 |
| GCAAGTGGCA | GGAGCAAGGT | AATAAAAGGG | TCCTTGCCTT | TAATTGGTGA | AGCAGATTGC | 960 |
| CTTCACGAAA | AATACGGTGG | ATTAAACAAA | AGCAAGCCTT | ACTACACAGG | AGAACATGCA | 1020 |
| AAAGCCATAG | GAAATTGCCC | AATATGGGTG | AAAACACCTT | TGAAGCTTGC | CAATGGAACC | 1080 |
| AGATATAGAC | CTCCTGCAAA | ACTATTAAAG | GAAAGGGGTT | TCTTCGGAGC | TATTGCTGGT | 1140 |
| TTCTTAGAAG | GAGGATGGGA | AGGAATGATT | GCAGGTTGGC | ACGGATACAC | ATCTCACGGG | 1200 |
| GCACATGGAG | TGGCAGTGGC | AGCAGACCTT | AAGAGTACGC | AAGAAGCCAT | AAACAAGATA | 1260 |
| ACAAAAAATC | TCAATTCTTT | GAGTGAGCTA | GAAGTAAAGA | ACCTTCAAAG | ACTAAGTGGT | 1320 |
| GCCATGGATG | AACTCCACAA | CGAAATACTC | GAGCTGGATG | AGAAAGTGGA | TGATCTCAGA | 1380 |
| GCTGACACAA | TAAGCTCGCA | AATAGAGCTT | GCAGTCTTAC | TTTCCAACGA | AGGAATAATA | 1440 |
| AACAGTGAAG | ATGAGCATCT | ATTGGCACTT | GAGAGAAAAC | TAAAGAAAAT | GCTGGGTCCC | 1500 |
| TCTGCTGTAG | ACATAGGGAA | TGGATGCTTC | GAAACAAAAC | ACAAGTGCAA | CCAGACCTGC | 1560 |
| TTAGACAGGA | TAGCTGCTGG | CACCTTTAAT | GCAGGAGAAT | TTTCTCTTCC | CACTTTTGAT | 1620 |
| TCACTGAATA | TTACTGCTGC | ATCTTTAAAT | GATGATGGAT | TGGATAATCA | TACTATACTG | 1680 |
| CTCTACTACT | CAACTGCTGC | TTCTAGTTTG | GCTGTAACAT | TGATGATAGC | TATTTTTATT | 1740 |
| GTTTATATGG | TCTCCAGAGA | CAATGTTTCT | TGTTCCATCT | GTCTGTGAGG | TACCAGATCT | 1800 |
| TAATTAATTA | A | | | | | 1811 |

(2) INFORMATION FOR SEQ ID NO:13:

(i) SEQUENCE CHARACTERISTICS:
(A) LENGTH: 589 amino acids
(B) TYPE: amino acid
(C) STRANDEDNESS: single
(D) TOPOLOGY: linear (ii) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Influenza virus
    ( C ) INDIVIDUAL ISOLATE: B/Netherlands/13/94 rHA ( i x ) FEATURE:
    ( A ) NAME/KEY: AcNPV 61K protein signal sequence
    ( B ) LOCATION: 1 to 18

( i x ) FEATURE:
    ( A ) NAME/KEY: mature rHA
    ( B ) LOCATION: 19 to 571

( x i ) SEQUENCE DESCRIPTION: SEQ ID NO:13:

```
Met Pro Leu Tyr Lys Leu Leu Asn Val Leu Trp Leu Val Ala Val Ser
  1               5                  10                  15

Asn Ala Ile Pro Gly Asp Arg Ile Cys Thr Gly Ile Thr Ser Ser Lys
             20                  25                  30

Ser Pro His Val Val Lys Thr Ala Thr Gln Gly Glu Val Asn Val Thr
         35                  40                  45

Gly Val Ile Pro Leu Thr Thr Thr Pro Thr Lys Ser His Phe Ala Asn
     50                  55                  60

Leu Lys Gly Thr Lys Thr Arg Gly Lys Leu Cys Pro Asn Cys Leu Asn
 65                  70                  75                  80

Cys Thr Asp Leu Asp Val Ala Leu Gly Arg Pro Met Cys Val Gly Ile
                 85                  90                  95

Thr Pro Ser Ala Lys Ala Ser Ile Leu His Glu Val Arg Pro Val Thr
            100                 105                 110

Ser Gly Cys Phe Pro Ile Met His Asp Arg Thr Lys Ile Arg Gln Leu
        115                 120                 125

Pro Asn Leu Leu Arg Gly Tyr Glu Asn Ile Arg Leu Ser Thr Gln Asn
    130                 135                 140

Val Ile Asn Ala Glu Lys Ala Pro Gly Gly Pro Tyr Arg Leu Gly Thr
145                 150                 155                 160

Ser Gly Ser Cys Pro Asn Val Thr Ser Arg Thr Gly Phe Phe Ala Thr
                165                 170                 175

Met Ala Trp Ala Val Pro Arg Asp Asn Lys Thr Ala Thr Asn Pro Leu
            180                 185                 190

Thr Val Glu Val Pro Tyr Ile Cys Thr Lys Gly Glu Asp Gln Ile Thr
        195                 200                 205

Val Trp Gly Phe His Ser Asp Asn Lys Thr Gln Met Lys Asn Leu Tyr
    210                 215                 220

Gly Asp Ser Asn Pro Gln Lys Phe Thr Ser Ser Ala Asn Gly Val Thr
225                 230                 235                 240

Thr His Tyr Val Ser Gln Ile Gly Gly Phe Pro Asp Gln Thr Glu Asp
                245                 250                 255

Gly Gly Leu Pro Gln Ser Gly Arg Ile Val Val Asp Tyr Met Val Gln
            260                 265                 270

Lys Pro Gly Lys Thr Gly Thr Ile Val Tyr Gln Arg Gly Ile Leu Leu
        275                 280                 285

Pro Gln Lys Val Trp Cys Ala Ser Gly Arg Ser Lys Val Ile Lys Gly
    290                 295                 300

Ser Leu Pro Leu Ile Gly Glu Ala Asp Cys Leu His Glu Lys Tyr Gly
305                 310                 315                 320
```

| Gly | Leu | Asn | Lys | Ser<br>325 | Lys | Pro | Tyr | Tyr | Thr<br>330 | Gly | Glu | His | Ala | Lys<br>335 | Ala |
|---|---|---|---|---|---|---|---|---|---|---|---|---|---|---|---|
| Ile | Gly | Asn | Cys<br>340 | Pro | Ile | Trp | Val | Lys<br>345 | Thr | Pro | Leu | Lys | Leu<br>350 | Ala | Asn |
| Gly | Thr | Arg<br>355 | Tyr | Arg | Pro | Pro | Ala<br>360 | Lys | Leu | Leu | Lys | Glu<br>365 | Arg | Gly | Phe |
| Phe | Gly<br>370 | Ala | Ile | Ala | Gly | Phe<br>375 | Leu | Glu | Gly | Gly | Trp<br>380 | Glu | Gly | Met | Ile |
| Ala<br>385 | Gly | Trp | His | Gly | Tyr<br>390 | Thr | Ser | His | Gly | Ala<br>395 | His | Gly | Val | Ala | Val<br>400 |
| Ala | Ala | Asp | Leu | Lys<br>405 | Ser | Thr | Gln | Glu | Ala<br>410 | Ile | Asn | Lys | Ile | Thr<br>415 | Lys |
| Asn | Leu | Asn | Ser<br>420 | Leu | Ser | Glu | Leu | Glu<br>425 | Val | Lys | Asn | Leu | Gln<br>430 | Arg | Leu |
| Ser | Gly | Ala<br>435 | Met | Asp | Glu | Leu | His<br>440 | Asn | Glu | Ile | Leu | Glu<br>445 | Leu | Asp | Glu |
| Lys | Val<br>450 | Asp | Asp | Leu | Arg | Ala<br>455 | Asp | Thr | Ile | Ser | Ser<br>460 | Gln | Ile | Glu | Leu |
| Ala<br>465 | Val | Leu | Leu | Ser | Asn<br>470 | Glu | Gly | Ile | Ile | Asn<br>475 | Ser | Glu | Asp | Glu | His<br>480 |
| Leu | Leu | Ala | Leu | Glu<br>485 | Arg | Lys | Leu | Lys | Lys<br>490 | Met | Leu | Gly | Pro | Ser<br>495 | Ala |
| Val | Asp | Ile | Gly<br>500 | Asn | Gly | Cys | Phe | Glu<br>505 | Thr | Lys | His | Lys | Cys<br>510 | Asn | Gln |
| Thr | Cys | Leu<br>515 | Asp | Arg | Ile | Ala | Ala<br>520 | Gly | Thr | Phe | Asn | Ala<br>525 | Gly | Glu | Phe |
| Ser | Leu<br>530 | Pro | Thr | Phe | Asp | Ser<br>535 | Leu | Asn | Ile | Thr | Ala<br>540 | Ala | Ser | Leu | Asn |
| Asp<br>545 | Asp | Gly | Leu | Asp | Asn<br>550 | His | Thr | Ile | Leu | Leu<br>555 | Tyr | Tyr | Ser | Thr | Ala<br>560 |
| Ala | Ser | Ser | Leu | Ala<br>565 | Val | Thr | Leu | Met | Ile<br>570 | Ala | Ile | Phe | Ile | Val<br>575 | Tyr |
| Met | Val | Ser | Arg<br>580 | Asp | Asn | Val | Ser | Cys<br>585 | Ser | Ile | Cys | Leu | | | |

( 2 ) INFORMATION FOR SEQ ID NO:14:

( i ) SEQUENCE CHARACTERISTICS:
        ( A ) LENGTH: 1757 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Influenza virus
        ( C ) INDIVIDUAL ISOLATE: A/Shandong/9/93 rHA ( i x ) FEATURE:
        ( A ) NAME/KEY: polyhedrin mRNA leader (partial)
        ( B ) LOCATION: 1 to 18

( i x ) FEATURE:
        ( A ) NAME/KEY: coding region for AcNPV 61K protein signal
            sequence
        ( B ) LOCATION: 19 to 72

( i x ) FEATURE:
    ( A ) NAME/KEY: SmaI restriction site
    ( B ) LOCATION: 76 to 81

( i x ) FEATURE:
    ( A ) NAME/KEY: coding region for mature rHA
    ( B ) LOCATION: 73 to 1728

( i x ) FEATURE:
    ( A ) NAME/KEY: KpnI restriction site
    ( B ) LOCATION: 1735 to 1740

( i x ) FEATURE:
    ( A ) NAME/KEY: BglII restriction site
    ( B ) LOCATION: 1741 to 1746

( i x ) FEATURE:
    ( A ) NAME/KEY: unversal translation termination signal
    ( B ) LOCATION: 1747 to 1757

( x i ) SEQUENCE DESCRIPTION: SEQ ID NO:14:

```
TAAAAAACC  TATAAATAAT  GCCCTTGTAC  AAATTGTTAA  ACGTTTTGTG  GTTGGTCGCC    60
GTTTCTAACG  CGATTCCCGG  GCAAGACCTT  CCAGGAAATG  ACAACAGCAC  AGCAACGCTG   120
TGCCTGGGAC  ATCATGCAGT  GCCAAACGGA  ACGCTAGTGA  AAACAATCAC  GAATGATCAA   180
ATTGAAGTGA  CTAATGCTAC  TGAGTTGGTT  CAGAGTTCCT  CAACAGGTAG  AATATGCGGC   240
AGTCCTCACC  GAATCCTTGA  TGGAAAAAAC  TGCACACTGA  TAGATGCTCT  ATTGGGAGAC   300
CCTCATTGTG  ATGGCTTCCA  AAATAAGGAA  TGGGACCTTT  TTGTTGAACG  CAGCAAAGCT   360
TACAGCAACT  GTTACCCTTA  TGATGTGCCG  GATTATGCCT  CCCTTAGGTC  ACTAGTTGCC   420
TCATCAGGCA  CCCTGGAGTT  TATCAATGAA  GACTTCAATT  GGACTGGAGT  CGCTCAGGAT   480
GGGGGAAGCT  ATGCTTGCAA  AAGAGGATCT  GTTAACAGTT  TCTTTAGTAG  ATTGAATTGG   540
TTGCACAAAT  TAGAATACAA  ATATCCAGCG  CTGAACGTGA  CTATGCCAAA  CAATGGCAAA   600
TTTGACAAAT  TGTACATTTG  GGGGGTTCAC  CACCCGAGCA  CGGACAGTGA  CCAAACCAGC   660
CTATATGTTC  GAGCATCAGG  GAGAGTCACA  GTCTCTACCA  AAAGAAGCCA  ACAAACTGTA   720
ACCCCGAATA  TCGGGTCTAG  ACCCTGGGTA  AGGGGTCAGT  CCAGTAGAAT  AAGCATCTAT   780
TGGACAATAG  TAAAACCGGG  AGACATACTT  TTGATTGATA  GCACAGGGAA  TCTAATTGCT   840
CCTCGGGGTT  ACTTCAAAAT  ACGAAATGGG  AAAAGCTCAA  TAATGAGGTC  AGATGCACCC   900
ATTGGCAACT  GCAGTTCTGA  ATGCATCACT  CCAAATGGAA  GCATTCCCAA  TGACAAACCT   960
TTTCAAAATG  TAAACAGAAT  CACATATGGG  GCCTGCCCCA  GATATGTTAA  GCAAAACACT  1020
CTGAAATTGG  CAACAGGGAT  GCGGAATGTA  CCAGAGAAAC  AAACTAGAGG  CATATTCGGC  1080
GCAATCGCAG  GTTTCATAGA  AAATGGTTGG  GAGGGAATGG  TAGACGGTTG  GTACGGTTTC  1140
AGGCATCAAA  ATTCTGAGGG  CACAGGACAA  GCAGCAGATC  TTAAAAGCAC  TCAAGCAGCA  1200
ATCGACCAAA  TCAACGGGAA  ACTGAATAGG  TTAATCGAGA  AAACGAACGA  GAAATTCCAT  1260
CAAATCGAAA  AAGAATTCTC  AGAAGTAGAA  GGGAGAATTC  AGGACCTCGA  GAAATATGTT  1320
GAAGACACTA  AAATAGATCT  CTGGTCTTAC  AACGCGGAGC  TTCTTGTTGC  CCTGGAGAAC  1380
CAACATACAA  TTGATCTAAC  TGACTCAGAA  ATGAACAAAC  TGTTTGAAAA  AACAAGGAAG  1440
CAACTGAGGG  AAAATGCTGA  GGACATGGGC  AATGGTTGCT  TCAAAATATA  CCACAAATGT  1500
GACAATGCCT  GCATAGGGTC  AATCAGAAAT  GGAACTTATG  ACCATGATGT  ATACAGAGAC  1560
GAAGCATTAA  ACAACCGGTT  CCAGATCAAA  GGTGTTGAGC  TGAAGTCAGG  ATACAAAGAT  1620
TGGATCCTAT  GGATTTCCTT  TGCCATATCA  TGCTTTTTGC  TTTGTGTTGT  TTTGCTGGGG  1680
TTCATCATGT  GGGCCTGCCA  AAAAGGCAAC  ATTAGGTGCA  ACATTTGCAT  TTGAGGTACC  1740
```

AGATCTTAAT TAATTAA                                                                 1757

(2) INFORMATION FOR SEQ ID NO:15:

(i) SEQUENCE CHARACTERISTICS:
        (A) LENGTH: 571 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Influenza virus
        (C) INDIVIDUAL ISOLATE: A/Shandong/9/93 rHA (ix) FEATURE:
        (A) NAME/KEY: AcNPV 61K protein signal sequence
        (B) LOCATION: 1 to 18

(ix) FEATURE:
        (A) NAME/KEY: mature rHA
        (B) LOCATION: 19 to 553

(xi) SEQUENCE DESCRIPTION: SEQ ID NO:15:

```
Met Pro Leu Tyr Lys Leu Leu Asn Val Leu Trp Leu Val Ala Val Ser
 1               5                  10                  15

Asn Ala Ile Pro Gly Gln Asp Leu Pro Gly Asn Asp Asn Ser Thr Ala
                20                  25                  30

Thr Leu Cys Leu Gly His His Ala Val Pro Asn Gly Thr Leu Val Lys
             35                  40                  45

Thr Ile Thr Asn Asp Gln Ile Glu Val Thr Asn Ala Thr Glu Leu Val
 50                  55                  60

Gln Ser Ser Ser Thr Gly Arg Ile Cys Gly Ser Pro His Arg Ile Leu
 65                  70                  75                  80

Asp Gly Lys Asn Cys Thr Leu Ile Asp Ala Leu Leu Gly Asp Pro His
                 85                  90                  95

Cys Asp Gly Phe Gln Asn Lys Glu Trp Asp Leu Phe Val Glu Arg Ser
                100                 105                 110

Lys Ala Tyr Ser Asn Cys Tyr Pro Tyr Asp Val Pro Asp Tyr Ala Ser
             115                 120                 125

Leu Arg Ser Leu Val Ala Ser Ser Gly Thr Leu Glu Phe Ile Asn Glu
     130                 135                 140

Asp Phe Asn Trp Thr Gly Val Ala Gln Asp Gly Gly Ser Tyr Ala Cys
145                 150                 155                 160

Lys Arg Gly Ser Val Asn Ser Phe Phe Ser Arg Leu Asn Trp Leu His
                165                 170                 175

Lys Leu Glu Tyr Lys Tyr Pro Ala Leu Asn Val Thr Met Pro Asn Asn
             180                 185                 190

Gly Lys Phe Asp Lys Leu Tyr Ile Trp Gly Val His His Pro Ser Thr
             195                 200                 205

Asp Ser Asp Gln Thr Ser Leu Tyr Val Arg Ala Ser Gly Arg Val Thr
     210                 215                 220

Val Ser Thr Lys Arg Ser Gln Gln Thr Val Thr Pro Asn Ile Gly Ser
225                 230                 235                 240

Arg Pro Trp Val Arg Gly Gln Ser Ser Arg Ile Ser Ile Tyr Trp Thr
                245                 250                 255
```

Ile Val Lys Pro Gly Asp Ile Leu Leu Ile Asp Ser Thr Gly Asn Leu
            260             265             270

Ile Ala Pro Arg Gly Tyr Phe Lys Ile Arg Asn Gly Lys Ser Ser Ile
            275             280             285

Met Arg Ser Asp Ala Pro Ile Gly Asn Cys Ser Ser Glu Cys Ile Thr
            290             295             300

Pro Asn Gly Ser Ile Pro Asn Asp Lys Pro Phe Gln Asn Val Asn Arg
305             310             315             320

Ile Thr Tyr Gly Ala Cys Pro Arg Tyr Val Lys Gln Asn Thr Leu Lys
            325             330             335

Leu Ala Thr Gly Met Arg Asn Val Pro Glu Lys Gln Thr Arg Gly Ile
            340             345             350

Phe Gly Ala Ile Ala Gly Phe Ile Glu Asn Gly Trp Glu Gly Met Val
            355             360             365

Asp Gly Trp Tyr Gly Phe Arg His Gln Asn Ser Glu Gly Thr Gly Gln
            370             375             380

Ala Ala Asp Leu Lys Ser Thr Gln Ala Ala Ile Asp Gln Ile Asn Gly
385             390             395             400

Lys Leu Asn Arg Leu Ile Glu Lys Thr Asn Glu Lys Phe His Gln Ile
            405             410             415

Glu Lys Glu Phe Ser Glu Val Glu Gly Arg Ile Gln Asp Leu Glu Lys
            420             425             430

Tyr Val Glu Asp Thr Lys Ile Asp Leu Trp Ser Tyr Asn Ala Glu Leu
            435             440             445

Leu Val Ala Leu Glu Asn Gln His Thr Ile Asp Leu Thr Asp Ser Glu
            450             455             460

Met Asn Lys Leu Phe Glu Lys Thr Arg Lys Gln Leu Arg Glu Asn Ala
465             470             475             480

Glu Asp Met Gly Asn Gly Cys Phe Lys Ile Tyr His Lys Cys Asp Asn
            485             490             495

Ala Cys Ile Gly Ser Ile Arg Asn Gly Thr Tyr Asp His Asp Val Tyr
            500             505             510

Arg Asp Glu Ala Leu Asn Asn Arg Phe Gln Ile Lys Gly Val Glu Leu
            515             520             525

Lys Ser Gly Tyr Lys Asp Trp Ile Leu Trp Ile Ser Phe Ala Ile Ser
            530             535             540

Cys Phe Leu Leu Cys Val Val Leu Leu Gly Phe Ile Met Trp Ala Cys
545             550             555             560

Gln Lys Gly Asn Ile Arg Cys Asn Ile Cys Ile
            565             570

( 2 ) INFORMATION FOR SEQ ID NO:16:

( i ) SEQUENCE CHARACTERISTICS:
        ( A ) LENGTH: 1814 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Influenza virus
        ( C ) INDIVIDUAL ISOLATE: B/Shanhai/4/94 rHA ( i x ) FEATURE:
    ( A ) NAME/KEY: polyhedrin mRNA leader (partial)
    ( B ) LOCATION: 1 to 18

( i x ) FEATURE:
    ( A ) NAME/KEY: coding region for AcNPV 61K protein signal
        sequence
    ( B ) LOCATION: 19 to 72

( i x ) FEATURE:
    ( A ) NAME/KEY: SmaI restriction site
    ( B ) LOCATION: 76 to 81

( i x ) FEATURE:
    ( A ) NAME/KEY: KpnI restriction site
    ( B ) LOCATION: 82 to 87

( i x ) FEATURE:
    ( A ) NAME/KEY: coding region for mature rHA
    ( B ) LOCATION: 73 to 1794

( i x ) FEATURE:
    ( A ) NAME/KEY: unversal translation termination signal
    ( B ) LOCATION: 1804 to 1814

( x i ) SEQUENCE DESCRIPTION: SEQ ID NO:16:

```
TAAAAAAACC  TATAAATAAT  GCCCTTGTAC  AAATTGTTAA  ACGTTTTGTG  GTTGGTCGCC    60
GTTTCTAACG  CGATTCCCGG  GGGTACCGAT  CGAATCTGCA  CTGGGATAAC  ATCTTCAAAC   120
TCACCTCATG  TGGTCAAAAC  AGCTACTCAA  GGGGAGGTCA  ATGTGACTGG  TGTGATACCA   180
CTGACAACAA  CACCAACAAA  ATCTCATTTT  GCAAATCTCA  AAGGAACAAA  GACCAGAGGG   240
AAACTATGCC  CAAACTGTCT  CAACTGCACA  GATCTGGATG  TGGCCTTGGG  CAGACCAATG   300
TGTGTGGGGA  CCACACCTTC  GGCAAAAGCT  TCAATACTCC  ACGAAGTCAG  ACCTGTTACA   360
TCCGGGTGCT  TTCCTATAAT  GCACGACAGA  ACAAAAATCA  GACAGCTACC  CAATCTTCTC   420
AGAGGATATG  AAAATATCAG  ATTATCAACC  CAAAACGTTA  TCAACGCAGA  AAAGGCACCA   480
GGAGGACCCT  ACAGACTTGG  AACCTCAGGA  TCTTGCCCTA  ACGCTACCAG  TAGAAGCGGA   540
TTTTTCGCAA  CAATGGCTTG  GGCTGTCCCA  AGGGACAACA  ACAAAACAGC  AACGAATCCA   600
CTAACAGTAG  AAGTACCATA  CATTTGCACA  AAAGGAGAAG  ACCAAATTAC  TGTTTGGGGG   660
TTCCATTCTG  ATAACAAACC  CCAAATGAAA  AACCTCTATG  GAGACTCAAA  TCCTCAAAAG   720
TTCACCTCAT  CTGCTAATGG  AGTAACCACA  CATTATGTTT  CTCAGATTGG  CGGCTTCCCA   780
GATCAAACAG  AAGACGGAGG  GCTACCACAA  AGCGGCAGAA  TTGTTGTTGA  TTACATGGTG   840
CAAAAACCTG  GAAGACAGG   AACAATTGTC  TATCAGAGAG  GTGTTTTGTT  GCCTCAAAAG   900
GTGTGGTGCG  CTAGTGGCAG  GAGCAAAGTA  ATAAAGGGT   CCTTGCCTTT  AATTGGTGAA   960
GCAGATTGCC  TTCACGAAAA  ATACGGTGGA  TTAAACAAAA  GCAAGCCTTA  CTACACAGGA  1020
GAACATGCAA  AAGCCATAGG  AAATTGCCCA  ATATGGGTGA  AAACACCTTT  GAAGCTTGCC  1080
AATGGAACCA  AATATAGACC  TCCTGCAAAA  CTATTAAAGG  AAAGGGGTTT  CTTCGGAGCT  1140
ATTGCTGGTT  TCTTAGAAGG  AGGATGGGAA  GGAATGATTG  CAGGTTGGCA  CGGATACACA  1200
TCTCACGGAG  CACATGGAGT  GGCAGTGGCA  GCAGACCTTA  AGAGTACGCA  AGAAGCCATA  1260
AACAAGATAA  CAAAAAATCT  CAATTCTTTG  AGTGAGCTAG  AAGTAAAGAA  TCTTCAAAGG  1320
CTAAGTGGTG  CCATGGATGA  ACTCCACAAC  GAAATACTCG  AGCTGGATGA  GAAAGTGGAT  1380
GATCTCAGAG  CTGACACAAT  AAGCTCGCAA  ATAGAACTTG  CAGTCTTGCT  TTCCAACGAA  1440
GGAATAATAA  ACAGTGAAGA  TGAGCATCTA  TTGGCACTTG  AGAGAAAACT  AAAGAAAATG  1500
CTGGGTCCCT  CTGCTGTAGA  CATAGGAAAT  GGATGCTTCG  AAACCAAACA  CAAGTGCAAC  1560
CAGACCTGCT  TAGACAGGAT  AGCTGCTGGC  ACCTTTAATG  CGGGAGAATT  TTCTCTTCCC  1620
```

```
ACTTTTGATT CACTGAATAT TACTGCTGCA TCTTTAAATG ATGATGGATT GGATAACCAT    1680

ACTATACTGC TCTACTACTC AACTGCTGCT TCTAGTTTGG CGGTAACATT GATGATAGCT    1740

ATTTTTATTG TTTATATGGT CTCCAGAGAC AATGTTTCTT GCTCCATCTG TCTGTGAGGA    1800

TCTTAATTAA TTAA                                                      1814
```

( 2 ) INFORMATION FOR SEQ ID NO:17:

( i ) SEQUENCE CHARACTERISTICS:
( A ) LENGTH: 592 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Influenza virus
( C ) INDIVIDUAL ISOLATE: B/Shanhai/4/94 rHA ( i x ) FEATURE:
( A ) NAME/KEY: AcNPV 61K protein signal peptide
( B ) LOCATION: 1 to 18

( i x ) FEATURE:
( A ) NAME/KEY: mature rHA
( B ) LOCATION: 19 to 574

( x i ) SEQUENCE DESCRIPTION: SEQ ID NO:17:

```
Met Pro Leu Tyr Lys Leu Leu Asn Val Leu Trp Leu Val Ala Val Ser
  1               5                  10                  15

Asn Ala Ile Pro Gly Gly Thr Asp Arg Ile Cys Thr Gly Ile Thr Ser
             20                  25                  30

Ser Asn Ser Pro His Val Val Lys Thr Ala Thr Gln Gly Glu Val Asn
         35                  40                  45

Val Thr Gly Val Ile Pro Leu Thr Thr Thr Pro Thr Lys Ser His Phe
     50                  55                  60

Ala Asn Leu Lys Gly Thr Lys Thr Arg Gly Lys Leu Cys Pro Asn Cys
 65                  70                  75                  80

Leu Asn Cys Thr Asp Leu Asp Val Ala Leu Gly Arg Pro Met Cys Val
                 85                  90                  95

Gly Thr Thr Pro Ser Ala Lys Ala Ser Ile Leu His Glu Val Arg Pro
            100                 105                 110

Val Thr Ser Gly Cys Phe Pro Ile Met His Asp Arg Thr Lys Ile Arg
        115                 120                 125

Gln Leu Pro Asn Leu Leu Arg Gly Tyr Glu Asn Ile Arg Leu Ser Thr
    130                 135                 140

Gln Asn Val Ile Asn Ala Glu Lys Ala Pro Gly Gly Pro Tyr Arg Leu
145                 150                 155                 160

Gly Thr Ser Gly Ser Cys Pro Asn Ala Thr Ser Arg Ser Gly Phe Phe
                165                 170                 175

Ala Thr Met Ala Trp Ala Val Pro Arg Asp Asn Asn Lys Thr Ala Thr
            180                 185                 190

Asn Pro Leu Thr Val Glu Val Pro Tyr Ile Cys Thr Lys Gly Glu Asp
        195                 200                 205

Gln Ile Thr Val Trp Gly Phe His Ser Asp Asn Lys Pro Gln Met Lys
```

|     |     |     |     | 210 |     |     |     |     | 215 |     |     |     |     | 220 |     |
|---|---|---|---|---|---|---|---|---|---|---|---|---|---|---|---|

Asn Leu Tyr Gly Asp Ser Asn Pro Gln Lys Phe Thr Ser Ser Ala Asn
225                     230                 235                 240

Gly Val Thr Thr His Tyr Val Ser Gln Ile Gly Gly Phe Pro Asp Gln
            245                 250                 255

Thr Glu Asp Gly Gly Leu Pro Gln Ser Gly Arg Ile Val Val Asp Tyr
            260             265                 270

Met Val Gln Lys Pro Gly Lys Thr Gly Thr Ile Val Tyr Gln Arg Gly
        275             280                 285

Val Leu Leu Pro Gln Lys Val Trp Cys Ala Ser Gly Arg Ser Lys Val
    290             295             300

Ile Lys Gly Ser Leu Pro Leu Ile Gly Glu Ala Asp Cys Leu His Glu
305             310             315                 320

Lys Tyr Gly Gly Leu Asn Lys Ser Lys Pro Tyr Tyr Thr Gly Glu His
            325             330             335

Ala Lys Ala Ile Gly Asn Cys Pro Ile Trp Val Lys Thr Pro Leu Lys
            340             345             350

Leu Ala Asn Gly Thr Lys Tyr Arg Pro Pro Ala Lys Leu Leu Lys Glu
        355             360             365

Arg Gly Phe Phe Gly Ala Ile Ala Gly Phe Leu Glu Gly Gly Trp Glu
    370             375             380

Gly Met Ile Ala Gly Trp His Gly Tyr Thr Ser His Gly Ala His Gly
385             390             395                 400

Val Ala Val Ala Ala Asp Leu Lys Ser Thr Gln Glu Ala Ile Asn Lys
            405                 410             415

Ile Thr Lys Asn Leu Asn Ser Leu Ser Glu Leu Glu Val Lys Asn Leu
            420             425             430

Gln Arg Leu Ser Gly Ala Met Asp Glu Leu His Asn Glu Ile Leu Glu
        435             440             445

Leu Asp Glu Lys Val Asp Asp Leu Arg Ala Asp Thr Ile Ser Ser Gln
    450             455             460

Ile Glu Leu Ala Val Leu Leu Ser Asn Glu Gly Ile Ile Asn Ser Glu
465             470             475                 480

Asp Glu His Leu Leu Ala Leu Glu Arg Lys Leu Lys Lys Met Leu Gly
            485             490             495

Pro Ser Ala Val Asp Ile Gly Asn Gly Cys Phe Glu Thr Lys His Lys
            500             505             510

Cys Asn Gln Thr Cys Leu Asp Arg Ile Ala Ala Gly Thr Phe Asn Ala
        515             520             525

Gly Glu Phe Ser Leu Pro Thr Phe Asp Ser Leu Asn Ile Thr Ala Ala
    530             535             540

Ser Leu Asn Asp Asp Gly Leu Asp Asn His Thr Ile Leu Leu Tyr Tyr
545             550             555             560

Ser Thr Ala Ala Ser Ser Leu Ala Val Thr Leu Met Ile Ala Ile Phe
            565             570             575

Ile Val Tyr Met Val Ser Arg Asp Asn Val Ser Cys Ser Ile Cys Leu
            580             585             590

( 2 ) INFORMATION FOR SEQ ID NO:18:

( i ) SEQUENCE CHARACTERISTICS:
        ( A ) LENGTH: 1802 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Influenza virus
    ( C ) INDIVIDUAL ISOLATE: B/Harbin/7/94 rHA ( i x ) FEATURE:
    ( A ) NAME/KEY: polyhedrin mRNA leader (partial)
    ( B ) LOCATION: 1 to 18

( i x ) FEATURE:
    ( A ) NAME/KEY: coding region for HA signal peptide sequence
    ( B ) LOCATION: 19 to 69

( i x ) FEATURE:
    ( A ) NAME/KEY: SmaI restriction site
    ( B ) LOCATION: 22 to 27

( i x ) FEATURE:
    ( A ) NAME/KEY: coding region for mature rHA
    ( B ) LOCATION: 70 to 1776

( i x ) FEATURE:
    ( A ) NAME/KEY: KpnI restriction site
    ( B ) LOCATION: 1780 to 1785

( i x ) FEATURE:
    ( A ) NAME/KEY: BglII restriction site
    ( B ) LOCATION: 1786 to 1791

( i x ) FEATURE:
    ( A ) NAME/KEY: unversal translation termination signal
    ( B ) LOCATION: 1792 to 1802

( x i ) SEQUENCE DESCRIPTION: SEQ ID NO:18:

TAAAAAAACC TATAAATAAT GCCCGGGAAG GCAATAATTG TACTACTCAT GGTAGTAACA 60

TCCAACGCAG ATCGAATCTG CACTGGGATA ACATCTTCAA ACTCACCTCA TGTGGTCAAA 120

ACAGCTACTC AAGGGGAAGT CAATGTGACT GGTGTGATAC CACTGACAAC AACACCAACA 180

AAATCTCATT TTGCAAATCT AAAAGGAACA AAGACCAGAG GGAAACTATG CCCAAACTGT 240

CTCAACTGCA CAGATCTGGA TGTGGCCTTG GGCAGACCAA TGTGTGTGGG GACCACACCT 300

TCGGCAAAAG CTTCAATACT CCACGAAGTC AGACCTGTTA CATCCGGGTG CTTTCCTATA 360

ATGCACGACA GAACAAAAAT CAGACAGCTA CCCAATCTTC TCAGAGGATA TGAAAATATC 420

AGATTATCAA CCCAAAACGT TATCAATGCA GAAAAAGCAC CAGGAGGACC CTACAGACTT 480

GGAACCTCAG GATCTTGCCC TAACGCTACC AGTAGAAGCG GATTTTTTGC AACAATGGCT 540

TGGGCTGTCC CAAGGGACGA CAACAAAACA GCAACGAATC CACTAACAGT AGAAGTACCA 600

TACGTTTGTA CAGAAGGAGA AGACCAAATT ACTGTTTGGG GGTTCCATTC TGATAACAAA 660

GCCCAAATGA AAAACCTCTA TGGAGACTCA AATCCTCAAA AGTTCACCTC ATCTGCTAAT 720

GGAGTAACCA CACATTATGT TTCTCAGATT GGCGGCTTCC CAGATCAAAC AGAAGACGGA 780

GGGCTACCAC AAAGCGGCAG AATTGTTGTT GATTACATGG TGCAAAAACC TGGGAAAACA 840

GGAACAATTG TCTATCAAAG AGGTGTTTTG TTGCCTCAAA AGGTGTGGTG CGCGAGTGGC 900

AGGAGCAAAG TAATAAAAGG GTCCTTGCCT TTAATTGGTG AAGCAGATTG CCTTCACGAA 960

AAATACGGTG GATTAAACAA AAGCAAGCCT TACTACACAG GAGAACATGC AAAAGCCATA 1020

GGAAATTGCC CAATATGGGT GAAAACACCT TTGAAGCTTG CCAATGGAAC CAAATATAGA 1080

CCTCCTGCAA AACTATTAAA GGAAAGGGGT TTCTTCGGAG CTATTGCTGG TTTCTTAGAA 1140

GGAGGATGGG AAGGAATGAT TGCAGGTTGG CACGGATACA CATCTCACGG AGCACATGGA 1200

-continued

```
GTGGCAGTGG CAGCAGACCT TAAGAGTACG CAAGAAGCCA TAAACAAGAT AACAAAAAAT    1260

CTCAATTCTT TGAGTGAGCT AGAAGTAAAG AATCTTCAAA GACTAAGTGG TGCCATGGAT    1320

GAACTCCATA ACGAAATACT CGAGCTGGAT GAGAAAGTGG ATGATCTCAG AGCTGACACT    1380

ATAAGCTCGC AAATAGAACT TGCAGTCTTG CTTTCCAACG AAGGAATAAT AAACAGTGAA    1440

GATGAGCATC TATTGGCACT TGAGAGAAAA CTAAAGAAAA TGCTGGGTCC CTCTGCTGTA    1500

GACATAGGGA ATGGATGCTT CGAAACCAAA CACAAGTGCA ACCAGACCTG CTTAGACAGG    1560

ATAGCTGCTG GCACCTTTAA TGCAGGAGAA TTTTCTCTCC CCACTTTTGA TTCACTGAAT    1620

ATTACTGCTG CATCTTTAAA TGATGATGGA TTGGATAATC ATACTATACT GCTCTACTAC    1680

TCAACTGCTG CTTCTAGTTT GGCTGTAACA TTGATGATAG CTATTTTTAT TGTTTATATG    1740

GTCTCCAGAG ACAATGTTTC ATGCTCCATC TGTCTGTGAG GTACCAGATC TTAATTAATT    1800

AA                                                                  1802
```

( 2 ) INFORMATION FOR SEQ ID NO:19:

( i ) SEQUENCE CHARACTERISTICS:
        ( A ) LENGTH: 586 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Influenza virus
        ( C ) INDIVIDUAL ISOLATE: B/Harbin/7/94 rHA ( i x ) FEATURE:
        ( A ) NAME/KEY: HA signal peptide
        ( B ) LOCATION: 1 to 17

( i x ) FEATURE:
        ( A ) NAME/KEY: mature rHA
        ( B ) LOCATION: 18 to 569

( x i ) SEQUENCE DESCRIPTION: SEQ ID NO:19:

```
Met Pro Gly Lys Ala Ile Ile Val Leu Leu Met Val Val Thr Ser Asn
 1               5                  10                  15

Ala Asp Arg Ile Cys Thr Gly Ile Thr Ser Ser Asn Ser Pro His Val
            20                  25                  30

Val Lys Thr Ala Thr Gln Gly Glu Val Asn Val Thr Gly Val Ile Pro
        35                  40                  45

Leu Thr Thr Thr Pro Thr Lys Ser His Phe Ala Asn Leu Lys Gly Thr
    50                  55                  60

Lys Thr Arg Gly Lys Leu Cys Pro Asn Cys Leu Asn Cys Thr Asp Leu
65                  70                  75                  80

Asp Val Ala Leu Gly Arg Pro Met Cys Val Gly Thr Thr Pro Ser Ala
                85                  90                  95

Lys Ala Ser Ile Leu His Glu Val Arg Pro Val Thr Ser Gly Cys Phe
            100                 105                 110

Pro Ile Met His Asp Arg Thr Lys Ile Arg Gln Leu Pro Asn Leu Leu
        115                 120                 125

Arg Gly Tyr Glu Asn Ile Arg Leu Ser Thr Gln Asn Val Ile Asn Ala
    130                 135                 140
```

-continued

| | | | | | | | | | | | | | | | |
|---|---|---|---|---|---|---|---|---|---|---|---|---|---|---|---|
| Glu | Lys | Ala | Pro | Gly | Gly | Pro | Tyr | Arg | Leu | Gly | Thr | Ser | Gly | Ser | Cys |
| 145 | | | | 150 | | | | | 155 | | | | | | 160 |
| Pro | Asn | Ala | Thr | Ser | Arg | Ser | Gly | Phe | Phe | Ala | Thr | Met | Ala | Trp | Ala |
| | | | | 165 | | | | | 170 | | | | | 175 | |
| Val | Pro | Arg | Asp | Asp | Asn | Lys | Thr | Ala | Thr | Asn | Pro | Leu | Thr | Val | Glu |
| | | | 180 | | | | | 185 | | | | | 190 | | |
| Val | Pro | Tyr | Val | Cys | Thr | Glu | Gly | Glu | Asp | Gln | Ile | Thr | Val | Trp | Gly |
| | | 195 | | | | | 200 | | | | | 205 | | | |
| Phe | His | Ser | Asp | Asn | Lys | Ala | Gln | Met | Lys | Asn | Leu | Tyr | Gly | Asp | Ser |
| | 210 | | | | | 215 | | | | 220 | | | | | |
| Asn | Pro | Gln | Lys | Phe | Thr | Ser | Ala | Asn | Gly | Val | Thr | Thr | His | Tyr | |
| 225 | | | | | 230 | | | | 235 | | | | | 240 | |
| Val | Ser | Gln | Ile | Gly | Gly | Phe | Pro | Asp | Thr | Glu | Asp | Gly | Gly | Leu | |
| | | | | 245 | | | | 250 | | | | | 255 | | |
| Pro | Gln | Ser | Gly | Arg | Ile | Val | Val | Asp | Tyr | Met | Val | Gln | Lys | Pro | Gly |
| | | | 260 | | | | | 265 | | | | | 270 | | |
| Lys | Thr | Gly | Thr | Ile | Val | Tyr | Gln | Arg | Gly | Val | Leu | Leu | Pro | Gln | Lys |
| | | 275 | | | | | 280 | | | | | 285 | | | |
| Val | Trp | Cys | Ala | Ser | Gly | Arg | Ser | Lys | Val | Ile | Lys | Gly | Ser | Leu | Pro |
| | 290 | | | | | 295 | | | | | 300 | | | | |
| Leu | Ile | Gly | Glu | Ala | Asp | Cys | Leu | His | Glu | Lys | Tyr | Gly | Gly | Leu | Asn |
| 305 | | | | | 310 | | | | | 315 | | | | | 320 |
| Lys | Ser | Lys | Pro | Tyr | Tyr | Thr | Gly | Glu | His | Ala | Lys | Ala | Ile | Gly | Asn |
| | | | | 325 | | | | | 330 | | | | | 335 | |
| Cys | Pro | Ile | Trp | Val | Lys | Thr | Pro | Leu | Lys | Leu | Ala | Asn | Gly | Thr | Lys |
| | | | 340 | | | | | 345 | | | | | 350 | | |
| Tyr | Arg | Pro | Pro | Ala | Lys | Leu | Leu | Lys | Glu | Arg | Gly | Phe | Phe | Gly | Ala |
| | | 355 | | | | | 360 | | | | | 365 | | | |
| Ile | Ala | Gly | Phe | Leu | Glu | Gly | Gly | Trp | Glu | Gly | Met | Ile | Ala | Gly | Trp |
| | | 370 | | | | 375 | | | | | 380 | | | | |
| His | Gly | Tyr | Thr | Ser | His | Gly | Ala | His | Gly | Val | Ala | Val | Ala | Ala | Asp |
| 385 | | | | | 390 | | | | | 395 | | | | | 400 |
| Leu | Lys | Ser | Thr | Gln | Glu | Ala | Ile | Asn | Lys | Ile | Thr | Lys | Asn | Leu | Asn |
| | | | | 405 | | | | | 410 | | | | | 415 | |
| Ser | Leu | Ser | Glu | Leu | Glu | Val | Lys | Asn | Leu | Gln | Arg | Leu | Ser | Gly | Ala |
| | | | 420 | | | | | 425 | | | | | 430 | | |
| Met | Asp | Glu | Leu | His | Asn | Glu | Ile | Leu | Glu | Leu | Asp | Glu | Lys | Val | Asp |
| | | 435 | | | | | 440 | | | | | 445 | | | |
| Asp | Leu | Arg | Ala | Asp | Thr | Ile | Ser | Ser | Gln | Ile | Glu | Leu | Ala | Val | Leu |
| | 450 | | | | | 455 | | | | | 460 | | | | |
| Leu | Ser | Asn | Glu | Gly | Ile | Ile | Asn | Ser | Glu | Asp | Glu | His | Leu | Leu | Ala |
| 465 | | | | | 470 | | | | | 475 | | | | | 480 |
| Leu | Glu | Arg | Lys | Leu | Lys | Lys | Met | Leu | Gly | Pro | Ser | Ala | Val | Asp | Ile |
| | | | | 485 | | | | | 490 | | | | | 495 | |
| Gly | Asn | Gly | Cys | Phe | Glu | Thr | Lys | His | Lys | Cys | Asn | Gln | Thr | Cys | Leu |
| | | | 500 | | | | | 505 | | | | | 510 | | |
| Asp | Arg | Ile | Ala | Ala | Gly | Thr | Phe | Asn | Ala | Gly | Glu | Phe | Ser | Leu | Pro |
| | | 515 | | | | | 520 | | | | | 525 | | | |
| Thr | Phe | Asp | Ser | Leu | Asn | Ile | Thr | Ala | Ala | Ser | Leu | Asn | Asp | Asp | Gly |
| | 530 | | | | | 535 | | | | | 540 | | | | |
| Leu | Asp | Asn | His | Thr | Ile | Leu | Leu | Tyr | Tyr | Ser | Thr | Ala | Ala | Ser | Ser |
| 545 | | | | | 550 | | | | | 555 | | | | | 560 |
| Leu | Ala | Val | Thr | Leu | Met | Ile | Ala | Ile | Phe | Ile | Val | Tyr | Met | Val | Ser |

```
                         565                      570                      575
Arg  Asp  Asn  Val  Ser  Cys  Ser  Ile  Cys  Leu
               580                      585
```

( 2 ) INFORMATION FOR SEQ ID NO:20:

( i ) SEQUENCE CHARACTERISTICS:
        ( A ) LENGTH: 1757 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Influenza virus
        ( C ) INDIVIDUAL ISOLATE: A/Johannesburg/33/94 rHA ( i x ) FEATURE:
        ( A ) NAME/KEY: polyhedrin mRNA leader (partial)
        ( B ) LOCATION: 1 to 18

( i x ) FEATURE:
        ( A ) NAME/KEY: coding region for AcNPV 61K protein signal
             peptide
        ( B ) LOCATION: 19 to 72

( i x ) FEATURE:
        ( A ) NAME/KEY: SmaI restriction site
        ( B ) LOCATION: 76 to 81

( i x ) FEATURE:
        ( A ) NAME/KEY: coding region for mature rHA
        ( B ) LOCATION: 73 to 1731

( i x ) FEATURE:
        ( A ) NAME/KEY: KpnI restriction site
        ( B ) LOCATION: 1735 to 1740

( i x ) FEATURE:
        ( A ) NAME/KEY: BglII restriction site
        ( B ) LOCATION: 1741 to 1747

( i x ) FEATURE:
        ( A ) NAME/KEY: unversal translation termination signal
        ( B ) LOCATION: 1747 to 1757

( x i ) SEQUENCE DESCRIPTION: SEQ ID NO:20:

```
TAAAAAACC  TATAAATAAT  GCCCTTGTAC  AAATTGTTAA  ACGTTTTGTG  GTTGGTCGCC    60

GTTTCTAACG  CGATTCCCGG  GCAGGACCTT  CCAGGAAATG  ACAACAGCAC  AGCAACGCTG   120

TGCCTGGGAC  ACCATGCAGT  GCCAAACGGA  ACGCTAGTGA  AAACAATCAC  GAATGATCAA   180

ATTGAAGTGA  CTAATGCTAC  TGAGCTGGTT  CAGAGTTCCC  CAACAGGTAG  AATATGCGAC   240

AGTCCTCACC  GAATCCTTGA  TGGAAAGAAC  TGCACACTGA  TAGATGCTCT  ATTGGGAGAC   300

CCTCATTGTG  ATGGCTTCCA  AAATAAGGAA  TGGGACCTTT  TTGTTGAACG  CAGCAAAGCT   360

TACAGCAACT  GTTACCCTTA  TGATGTGCCG  GATTATGCCT  CCCTTAGGTC  ACTAGTTGCC   420

TCATCAGGCA  CCCTGGAGTT  TATCAACGAA  AACTTCAATT  GGACTGGAGT  CGCTCAGGAT   480

GGGAAAAGCT  ATGCTTGCAA  AAGGGGATCT  GTTAACAGTT  TCTTTAGTAG  ATTGAATTGG   540

TTGCACAAAT  TAGAATACAA  ATATCCAGCG  CTGAACGTGA  CTATGCCAAA  CAATGGCAAA   600

TTTGACAAAT  TGTACATTTG  GGGGGTTCAC  CACCCGAGCA  CGGACAGTGA  CCAAACCAGC   660

CTATATGTCC  GAGCATCAGG  GAGAGTCACA  GTCTCTACCA  AAAGAAGCCA  ACAAACTGTA   720

ATCCCGGATA  TCGGGTATAG  ACCATGGGTA  AGGGGTCAGT  CCAGTAGAAT  AGGCATCTAT   780
```

-continued

```
TGGACAATAG TAAAACCGGG AGACATACTT TTGATTAATA GCACAGGGAA TCTAATTGCT     840
CCTCGGGGTT ACTTCAAAAT ACGAAATGGG AAAAGCTCAA TAATGAGGTC AGATGCACCC     900
ATTGGCAACT GCAGTTCTGA ATGCATCACT CCAAATGGAA GCATTCCCAA TGACAAACCT     960
TTTCAAAATG TAAACAGGAT CACATATGGG GCCTGCCCCA GATATGTTAA GCAAAACACT    1020
CTGAAATTGG CAACAGGGAT GCGGAATGTA CCAGAGAAAC AAACTAGAGG CATATTCGGC    1080
GCAATCGCAG GTTTCATAGA AAATGGTTGG GAGGGAATGG TAGACGGTTG GTACGGTTTC    1140
AGGCATCAAA ATTCTGAGGG CACAGGACAA GCTGCAGATC TTAAAAGCAC TCAAGCAGCA    1200
ATCGACCAAA TCAACGGGAA ACTGAATAGG TTAGTCGAGA AAACGAACGA GAAATTCCAT    1260
CAAATCGAAA AAGAATTCTC AGAAGTAGAA GGGAGAATTC AGGACCTCGA GAAATATGTT    1320
GAAGACACTA AAATAGATCT CTGGTCTTAC AATGCGGAGC TTCTTGTTGC TCTGGAGAAC    1380
CAACATACAA TTGATCTAAC TGACTCAGAA ATGAACAAAC TGTTTGAAAG AACAAGGAAG    1440
CAACTGAGGG AAAATGCTGA GGACATGGGC AATGGTTGTT TCAAAATATA CCACAAATGT    1500
GACAATGCCT GCATAGGGTC AATCAGAAAT GGAACTTATG ACCATGATGT ATACAGAGAC    1560
GAAGCATTAA ACAACCGGTT CCAGATCAAA GGTGTTGAGC TGAAGTCAGG ATACAAAGAT    1620
TGGATTCTAT GGATTTCCTT TGCCATATCA TGCTTTTTGC TTTGTGTTGT TTTGCTTGGG    1680
TTCATCATGT GGGCCTGCCA AAAAGGCAAC ATTAGGTGCA ACATTTGCAT TTGAGGTACC    1740
AGATCTTAAT TAATTAA                                                   1757
```

( 2 ) INFORMATION FOR SEQ ID NO:21:

( i ) SEQUENCE CHARACTERISTICS:
( A ) LENGTH: 571 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Influenza virus
( C ) INDIVIDUAL ISOLATE: A/Johannesburg/33/94 rHA ( i x ) FEATURE:
( A ) NAME/KEY: AcNPV 61K protein signal sequence
( B ) LOCATION: 1 to 18

( i x ) FEATURE:
( A ) NAME/KEY: mature rHA
( B ) LOCATION: 19 to 569

( x i ) SEQUENCE DESCRIPTION: SEQ ID NO:21:

```
Met Pro Leu Tyr Lys Leu Leu Asn Val Leu Trp Leu Val Ala Val Ser
  1               5                  10                  15

Asn Ala Ile Pro Gly Gln Asp Leu Pro Gly Asn Asp Asn Ser Thr Ala
             20                  25                  30

Thr Leu Cys Leu Gly His His Ala Val Pro Asn Gly Thr Leu Val Lys
         35                  40                  45

Thr Ile Thr Asn Asp Gln Ile Glu Val Thr Asn Ala Thr Glu Leu Val
     50                  55                  60

Gln Ser Ser Pro Thr Gly Arg Ile Cys Asp Ser Pro His Arg Ile Leu
 65                  70                  75                  80
```

-continued

| | | | | | | | | | | | | | | |
|---|---|---|---|---|---|---|---|---|---|---|---|---|---|---|
|Asp|Gly|Lys|Asn|Cys|Thr|Leu|Ile|Asp|Ala|Leu|Leu|Gly|Asp|Pro|His|
| | | | |85| | | |90| | | | |95| |
|Cys|Asp|Gly|Phe|Gln|Asn|Lys|Glu|Trp|Asp|Leu|Phe|Val|Glu|Arg|Ser|
| | | |100| | | |105| | | |110| | | |
|Lys|Ala|Tyr|Ser|Asn|Cys|Tyr|Pro|Tyr|Asp|Val|Pro|Asp|Tyr|Ala|Ser|
| | | |115| | |120| | | |125| | | | |
|Leu|Arg|Ser|Leu|Val|Ala|Ser|Ser|Gly|Thr|Leu|Glu|Phe|Ile|Asn|Glu|
| |130| | | |135| | | | |140| | | | |
|Asn|Phe|Asn|Trp|Thr|Gly|Val|Ala|Gln|Asp|Gly|Lys|Ser|Tyr|Ala|Cys|
|145| | | | |150| | | |155| | | | |160|
|Lys|Arg|Gly|Ser|Val|Asn|Ser|Phe|Phe|Ser|Arg|Leu|Asn|Trp|Leu|His|
| | | |165| | | |170| | | | |175| | |
|Lys|Leu|Glu|Tyr|Lys|Tyr|Pro|Ala|Leu|Asn|Val|Thr|Met|Pro|Asn|Asn|
| | | |180| | | |185| | | | |190| | |
|Gly|Lys|Phe|Asp|Lys|Leu|Tyr|Ile|Trp|Gly|Val|His|His|Pro|Ser|Thr|
| | |195| | | |200| | | | |205| | | |
|Asp|Ser|Asp|Gln|Thr|Ser|Leu|Tyr|Val|Arg|Ala|Ser|Gly|Arg|Val|Thr|
| |210| | | |215| | | | |220| | | | |
|Val|Ser|Thr|Lys|Arg|Ser|Gln|Gln|Thr|Val|Ile|Pro|Asp|Ile|Gly|Tyr|
|225| | | |230| | | | |235| | | | |240|
|Arg|Pro|Trp|Val|Arg|Gly|Gln|Ser|Ser|Ile|Gly|Ile|Tyr|Trp|Thr|
| | | |245| | | |250| | | | |255| | |
|Ile|Val|Lys|Pro|Gly|Asp|Ile|Leu|Leu|Ile|Asn|Ser|Thr|Gly|Asn|Leu|
| | |260| | | |265| | | |270| | | | |
|Ile|Ala|Pro|Arg|Gly|Tyr|Phe|Lys|Ile|Arg|Asn|Gly|Lys|Ser|Ser|Ile|
| |275| | | |280| | | |285| | | | | |
|Met|Arg|Ser|Asp|Ala|Pro|Ile|Gly|Asn|Cys|Ser|Ser|Glu|Cys|Ile|Thr|
| |290| | | |295| | | |300| | | | | |
|Pro|Asn|Gly|Ser|Ile|Pro|Asn|Asp|Lys|Pro|Phe|Gln|Asn|Val|Asn|Arg|
|305| | | |310| | | |315| | | | |320| |
|Ile|Thr|Tyr|Gly|Ala|Cys|Pro|Arg|Tyr|Val|Lys|Gln|Asn|Thr|Leu|Lys|
| | | |325| | | |330| | | | |335| | |
|Leu|Ala|Thr|Gly|Met|Arg|Asn|Val|Pro|Glu|Lys|Gln|Thr|Arg|Gly|Ile|
| | |340| | | |345| | | |350| | | | |
|Phe|Gly|Ala|Ile|Ala|Gly|Phe|Ile|Glu|Asn|Gly|Trp|Glu|Gly|Met|Val|
| |355| | | |360| | | |365| | | | | |
|Asp|Gly|Trp|Tyr|Gly|Phe|Arg|His|Gln|Asn|Ser|Glu|Gly|Thr|Gly|Gln|
| |370| | | |375| | | |380| | | | | |
|Ala|Ala|Asp|Leu|Lys|Ser|Thr|Gln|Ala|Ala|Ile|Asp|Gln|Ile|Asn|Gly|
|385| | | |390| | | |395| | | | |400| |
|Lys|Leu|Asn|Arg|Leu|Val|Glu|Lys|Thr|Asn|Glu|Lys|Phe|His|Gln|Ile|
| | | |405| | | |410| | | | |415| | |
|Glu|Lys|Glu|Phe|Ser|Glu|Val|Glu|Gly|Arg|Ile|Gln|Asp|Leu|Glu|Lys|
| | |420| | | |425| | | |430| | | | |
|Tyr|Val|Glu|Asp|Thr|Lys|Ile|Asp|Leu|Trp|Ser|Tyr|Asn|Ala|Glu|Leu|
| |435| | | |440| | | |445| | | | | |
|Leu|Val|Ala|Leu|Glu|Asn|Gln|His|Thr|Ile|Asp|Leu|Thr|Asp|Ser|Glu|
|450| | | |455| | | |460| | | | | | |
|Met|Asn|Lys|Leu|Phe|Glu|Arg|Thr|Arg|Lys|Gln|Leu|Arg|Glu|Asn|Ala|
|465| | | |470| | | |475| | | | |480| |
|Glu|Asp|Met|Gly|Asn|Gly|Cys|Phe|Lys|Ile|Tyr|His|Lys|Cys|Asp|Asn|
| | |485| | | |490| | | |495| | | | |
|Ala|Cys|Ile|Gly|Ser|Ile|Arg|Asn|Gly|Thr|Tyr|Asp|His|Asp|Val|Tyr|

|     |     |     |     |     |     |     |     |     |     |     |     |     |     |
| --- | --- | --- | --- | --- | --- | --- | --- | --- | --- | --- | --- | --- | --- |
|     |     |     | 500 |     |     |     |     | 505 |     |     |     | 510 |     |
| Arg | Asp | Glu | Ala | Leu | Asn | Asn | Arg | Phe | Gln | Ile | Lys | Gly | Val | Glu | Leu |
|     |     | 515 |     |     |     |     | 520 |     |     |     | 525 |     |     |
| Lys | Ser | Gly | Tyr | Lys | Asp | Trp | Ile | Leu | Trp | Ile | Ser | Phe | Ala | Ile | Ser |
|     |     | 530 |     |     |     | 535 |     |     |     | 540 |     |     |     |
| Cys | Phe | Leu | Leu | Cys | Val | Val | Leu | Leu | Gly | Phe | Ile | Met | Trp | Ala | Cys |
| 545 |     |     |     | 550 |     |     |     |     | 555 |     |     |     |     | 560 |
| Gln | Lys | Gly | Asn | Ile | Arg | Cys | Asn | Ile | Cys | Ile |
|     |     |     |     | 565 |     |     |     | 570 |     |     |

( 2 ) INFORMATION FOR SEQ ID NO:22:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

TGGTTGGTCG CCGTTTCTAA CGCGATTCCC GGGGGTACC 39

( 2 ) INFORMATION FOR SEQ ID NO:23:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

| Trp | Leu | Val | Ala | Val | Ser | Asn | Ala | Ile | Pro | Gly | Gly | Thr |
| --- | --- | --- | --- | --- | --- | --- | --- | --- | --- | --- | --- | --- |
| 1 |     |     |     | 5 |     |     |     |     | 10 |     |     |     |

( 2 ) INFORMATION FOR SEQ ID NO:24:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

TGGTTAGTCG CCGTGTCCTG CAGGCCAGAG AGGCCTTGGT ACC 43

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

GTCGCCGTGT CCAACGCG 18

( 2 ) INFORMATION FOR SEQ ID NO:26:

( i ) SEQUENCE CHARACTERISTICS:
        ( A ) LENGTH: 18 base pairs ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

TAATTGGCCA GAGAGGCC                                                                                      18

( 2 ) INFORMATION FOR SEQ ID NO:27:

( i ) SEQUENCE CHARACTERISTICS:
        ( A ) LENGTH: 38 bases
        ( B ) TYPE: nucleic acid
        ( C ) STRANDEDNESS: single
        ( D ) TOPOLOGY: linear ( x i ) SEQUENCE DESCRIPTION: SEQ ID NO:27:

GGGGGTACCC CCGGGGACTT TCCAGGAAAT GACAACAG                                                                38

( 2 ) INFORMATION FOR SEQ ID NO:28:

( i ) SEQUENCE CHARACTERISTICS:
        ( A ) LENGTH: 44 bases
        ( B ) TYPE: nucleic acid
        ( C ) STRANDEDNESS: single
        ( D ) TOPOLOGY: linear ( x i ) SEQUENCE DESCRIPTION: SEQ ID NO:28:

CCCGGTACCG AATCATCCTA GAAACAAGGG TGTTTTTAAT TAAT                                                         44

( 2 ) INFORMATION FOR SEQ ID NO:29:

( i ) SEQUENCE CHARACTERISTICS:
        ( A ) LENGTH: 47 bases
        ( B ) TYPE: nucleic acid
        ( C ) STRANDEDNESS: single
        ( D ) TOPOLOGY: linear ( x i ) SEQUENCE DESCRIPTION: SEQ ID NO:29:

GGGGAATTCG GTACCCCCGG GAAGGCAATA ATTGTACTAC TCATGGT                                                      47

( 2 ) INFORMATION FOR SEQ ID NO:30:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( x i ) SEQUENCE DESCRIPTION: SEQ ID NO:30:

GGTACCCCCG GGGATCGAAT CTGCACTGGG ATAACA                                                                  36

( 2 ) INFORMATION FOR SEQ ID NO:31:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( x i ) SEQUENCE DESCRIPTION: SEQ ID NO:31:

GGGGAATTCG GATCCGGTAC CTCACAGACA GATGGARCAA GAAACATTGT                                                   50